United States Patent [19]

Bouchaudon et al.

[11] 4,401,658

[45] Aug. 30, 1983

[54] TRI-, TETRA, AND PENTA-PEPTIDES, THEIR PREPARATION AND COMPOSITIONS CONTAINING THEM

[75] Inventors: Jean Bouchaudon, Morsang-sur-Orge; Gilles Dutruc-Rosset, Paris; Daniel Farge, Thiais; Claude James, Paris, all of France

[73] Assignee: Rhone-Poulenc Sante, Courbevoie, France

[21] Appl. No.: 331,593

[22] Filed: Dec. 17, 1981

[30] Foreign Application Priority Data

Dec. 19, 1980 [FR] France ............... 80 27020

[51] Int. Cl.³ .................... C07C 103/52; A61K 37/02
[52] U.S. Cl. .................... 424/177; 260/112.5 R
[58] Field of Search ............ 260/112.5 R; 424/177

[56] References Cited

U.S. PATENT DOCUMENTS 4,261,979 4/1981 Jolles et al. ............... 260/112.5 R
4,311,640 1/1982 Kuroda et al. ................. 424/177

*Primary Examiner*—Delbert R. Phillips
*Assistant Examiner*—F. T. Moezie
*Attorney, Agent, or Firm*—Stevens, Davis, Miller & Mosher

[57] ABSTRACT

The invention provides tri-, tetra- or penta-peptides of the general formula:

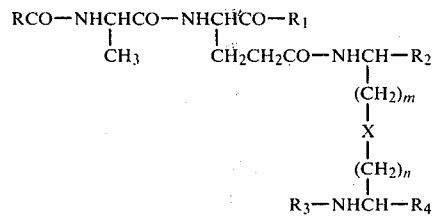

in which RCO is a fatty acid residue, $R_1$ is hydroxyl, amino, alkoxy or benzyloxy, $R_2$ and $R_4$ (identical or different) represent hydrogen, carboxyl, alkoxycarbonyl or benzyloxycarbonyl or an optionally esterified N-carbonylglycyl or N-carbonyl-D-alanyl radical, it being impossible for $R_2$ and $R_4$ simultaneously to represent hydrogen, $R_3$ is hydrogen, or represents a glycyl or D-alanyl residue (in which case, only one of the radicals $R_2$ and $R_4$ can represent an N-carbonylglycyl or N-carbonyl-D-alanyl radical), X is a sulphur atom or methylene, and m and n = 1 or 2, it being understood that if X is methylene, m and n are different from 1, their salts, their preparation and compositions containing them: the compounds are useful as vaccine adjuvants or as non-specific stimulants of anti-infectious or anti-tumoral activity.

10 Claims, No Drawings

TRI-, TETRA, AND PENTA-PEPTIDES, THEIR PREPARATION AND COMPOSITIONS CONTAINING THEM

The present invention relates to new tri-, tetra- or penta-peptides, their salts, if appropriate, their preparation and compositions containing them.

The present invention provides tri-, tetra- or penta-peptides of the general formula:

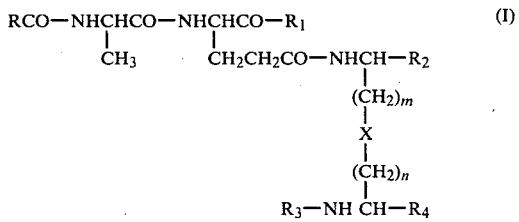

wherein RCO— represents a fatty acid residue in which R represents an alkyl radical containing 1 to 44 carbon atoms (which is optionally substituted by a hydroxyl, phenyl or cyclohexyl radical), an alkenyl radical containing 2 to 29 carbon atoms, which can contain more than one double bond, or a mycolic acid residue such as encountered in the structure of the bacterial wall of mycobacteria, Nocardia or Corynebacteria, $R_1$ represents a hydroxyl or amino radical, an alkoxy radical containing 1 to 4 carbon atoms or a benzyloxy radical, the symbols $R_2$ and $R_4$, which are identical or different, represent a hydrogen atom, a carboxyl or carbamoyl radical, an alkoxycarbonyl radical of which the alkyl part contains 1 to 4 carbon atoms, a benzyloxycarbonyl radical or an N-carbonylglycyl (-CONHCH$_2$COOH) or

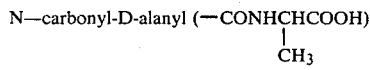

radical optionally esterified by an alkyl radical containing 1 to 4 carbon atoms or a benzyl radical, it being understood that $R_2$ and $R_4$ cannot simultaneously represent a hydrogen atom, $R_3$ represents a hydrogen atom or a glycyl or D-alanyl residue, it being understood that if $R_2$ and $R_4$, which are identical or different, each represent an N-carbonylglycyl radical or an N-carbonyl D-alanyl radical, $R_3$ represents a hydrogen atom, X represents a sulphur atom or a methylene radical, and m and n, which are identical or different, each represent an integer equal to 1 or 2, it being understood that if X represents a methylene radical, m and n cannot simultaneously be equal to 1, and it being understood that the alanine bonded to the glutamic acid is in the L form, the glutamic acid is in the D form, the lanthionine, if X represents a sulphur atom and m and n are equal to 1, the cystathionine, if X represents a sulphur atom and m and n are different, the homolanthionine, if X represents a sulphur atom and m and n are equal to 2, and the 2,7-diaminosuberic acid, if X represents a methylene radical and one of the symbols m or n is equal to 1 and the other is equal to 2, are in the D,D, L,L, D,D/L,L (racemic) or D,L (meso) form or in the form of L/meso or D/meso mixtures, and the thialysine, if one of the symbols $R_2$ or $R_4$ represents a hydrogen atom, X represents a sulphur atom and m and n are equal to 1, is in the L, D or D,L form, and salts thereof.

According to the present invention, the new peptides of the general formula (I) can be obtained in accordance with the methods generally used in peptide chemistry. The various reactions are carried out after the blocking, by suitable protective groups, of the amine or acid groups which must not participate in the reaction, and are followed, if appropriate, by the unblocking of these groups.

According to the present invention, the new products of the general formula (I) can be obtained by reacting a dipeptide of the general formula:

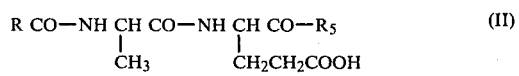

in which R is defined as above and $R_5$ represents an amino radical, an alkoxy radical containing 1 to 4 carbon atoms or a benzyloxy radical, with a product of the general formula:

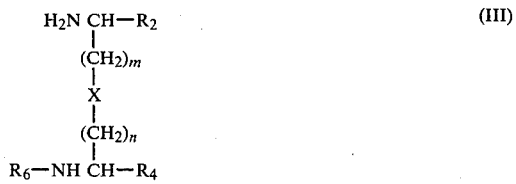

in which $R_2$, $R_4$, X, m and n are defined as above and $R_6$ represents a protective group of the amine group or a glycyl or D-alanyl radical of which the amine group is substituted by a protective group of the amine group, and then replacing the protective group represented or carried by $R_6$ by a hydrogen atom and, if desired, replacing the radical $R_5$, if it represents an alkoxy radical containing 1 to 4 carbon atoms or a benzyloxy radical, by a hydroxyl radical, and replacing the alkoxycarbonyl radicals containing 2 to 5 carbon atoms or benzyloxycarbonyl radicals, represented or carried by $R_2$ and/or $R_4$, by carboxyl radicals.

If the symbols $R_2$ and $R_4$ are different from a carboxyl radical or do not contain a carboxyl radical, the dipeptide of the general formula (II) is generally condensed in the presence of a condensation agent such as dicyclohexylcarbodiimide, the reaction being carried out in an organic solvent such as methylene chloride or dimethylformamide, at a temperature between −10° and 30° C.

In general, it is necessary to activate the free acid group of the dipeptide of the general formula (II) before it is reacted with the product of the general formula (III). Preferably, the activated derivative of the dipeptide of the general formula (II) is a mixed anhydride prepared in situ by reaction with an alkyl halogenoformate such as isobutyl chloroformate. The activated derivative is condensed in an organic solvent such as dioxane, tetrahydrofuran, chloroform, toluene or dimethylformamide, or in an aqueous-organic medium, in the presence of a base (an inorganic base such as sodium hydroxide, or an organic base such as triethylamine), at a temperature between −10° and +30° C.

The replacement of the protective group of the amine group, represented or carried by $R_6$, by a hydrogen atom, the replacement of the radical $R_5$ by a hydroxyl radical and the replacement of the radicals represented or carried by $R_2$ and/or $R_4$ by carboxyl radicals can be carried out in accordance with the known methods, depending on the nature of these groups. It is particularly advantageous to choose the radicals $R_2$, $R_4$, $R_5$ and $R_6$ so that their replacement can be carried out in a single step. By way of example, $R_6$ can represent or contain a t-butoxycarbonyl radical, $R_1$ can represent a t-butoxy radical and $R_2$ and/or $R_4$ can represent or contain a t-butoxycarbonyl radical, and under these conditions, the replacement of these radicals is carried out by acid hydrolysis. The hydrolysis can be carried out in acetic acid, in the presence of hydrochloric acid, at a temperature of the order of 20° C.

Again by way of example, if the protective group of an acid group is a benzyl radical and the protective group of the amine group is a benzyloxycarbonyl radical, the simultaneous removal of these protective groups can be carried out by means of hydrobromic acid in trifluoroacetic acid, or by using sodium in liquid ammonia. However, it can be necessary to remove one or more of the protective groups without affecting the others. In this case, the protective groups will be chosen e.g. so that their replacement is carried out under different hydrolysis conditions. Thus, the protective group of an acid group can be a t-butyl radical, which can be removed by reaction with hydrochloric acid in acetic acid, and the protective group of the amine group can be a benzyloxycarbonyl radical, which can be removed by reaction with hydrobromic acid in acetic acid.

According to the present invention, the new peptides of the general formula (I) can also be obtained by reacting an L-alanine derivative of the general formula:

in which R is defined as above, with a di-, tri- or tetra-peptide of the general formula:

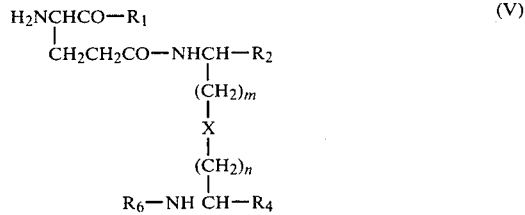

in which $R_1$, $R_2$, $R_4$, $R_6$, X, m and n are defined as above, and then replacing the protective group represented or carried by $R_6$ by a hydrogen atom and, if desired, replacing the radical $R_1$, if it represents an alkoxy radical containing 1 to 4 carbon atoms or a benzyloxy radical, by a hydroxyl radical, and replacing the alkoxycarbonyl radicals containing 2 to 5 carbon atoms or benzyloxycarbonyl radicals, represented or carried by $R_2$ and/or $R_4$, by carboxyl radicals, under the conditions described above for the reaction of a product of the general formula (II) with a product of the general formula (III).

According to the present invention, the new peptides of the general formula (I) can also be obtained by reacting an acid of the general formula:

in which R is defined as above, with a tri-, tetra- or penta-peptide of the general formula:

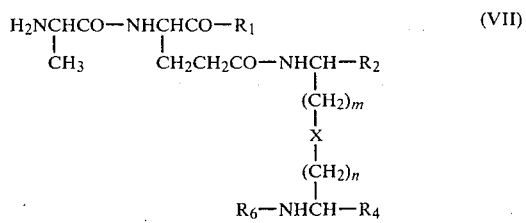

in which $R_1$, $R_2$, $R_4$, $R_6$, X, m and n are defined as above, and then replacing the protective group represented or carried by $R_6$ by a hydrogen atom and, if desired, replacing the radical $R_1$, if it represents an alkoxy radical containing 1 to 4 carbon atoms or a benzyloxy radical, by a hydroxyl radical, and replacing the alkoxycarbonyl radicals containing 2 to 5 carbon atoms or benzyloxycarbonyl radicals, represented or carried by $R_2$ and/or $R_4$, by carboxyl radicals, the reaction being carried out under the conditions given above for the condensation of the dipeptide of the general formula (II) with the product of the general formula (III). It is also possible to use the acid of the general formula (VI) in the form of an acid halide, preferably the chloride, the reaction being carried out in an organic solvent such as diethyl ether or methylene chloride, in the presence of a base (an inorganic base such as sodium hydroxide, or an organic base such as triethylamine), at a temperature between 0° and 30° C.

According to the present invention, the new peptides of the general formula (I) in which the symbols $R_2$ and/or $R_4$ represent an N-carbonylglycyl or N-carbonyl-D-alanyl radical optionally esterified by an alkyl radical containing 1 to 4 carbon atoms or a benzyl radical can also be obtained by reacting a free or esterified aminoacid of the general formula

in which $R_7$ represents a hydrogen atom or a methyl radical, the aminoacid being in the D form when $R_7$ represents methyl, and $R_8$ represents a hydroxyl radical, an alkoxy radical containing 1 to 4 carbon atoms or a benzyloxy radical, with a peptide of the general formula:

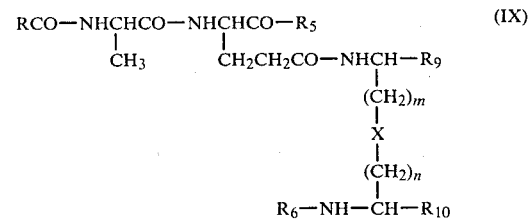

in which R, $R_5$, $R_6$, X, m and n are defined as above, one of the symbols $R_9$ or $R_{10}$ represents a carboxyl radical and the other represents a hydrogen atom, a carboxyl or carbamoyl radical, an alkoxycarbonyl radical containing 2 to 5 carbon atoms, a benzyloxycarbonyl radical or an N-carbonylglycyl or N-carbonyl-D-alanyl radical esterified by an alkyl radical containing 1 to 4 carbon atoms or by a benzyl radical, it being understood that if $R_9$ and $R_{10}$ each represent a carboxyl radical, $R_6$ represents a protective group of the amine group, and then, if appropriate, replacing the radicals $R_5$ and/or $R_8$, if they represent an alkoxy radical containing 1 to 4 carbon atoms or a benzyloxy radical, by a hydroxyl radical, and/or replacing the alkoxycarbonyl radicals containing 2 to 5 carbon atoms or benzyloxycarbonyl radicals, represented or carried by $R_9$ or $R_{10}$, by a carboxyl radical, and replacing the protective group represented or carried by $R_6$ by a hydrogen atom, under the conditions described above for the reaction of a product of the general formula (II) with a product of the general formula (III).

To obtain a product of the general formula (I) in which $R_2$ and $R_4$ are identical and represent an optionally esterified N-carbonylglycyl or N-carbonyl-D-alanyl radical, it is possible to use a product of the general formula (IX) in which $R_9$ and $R_{10}$ each represent a carboxyl radical.

To obtain a product of the general formula (I) in which the symbols $R_2$ and $R_4$ are identical or different and represent an optionally esterified N-carbonylglycyl or N-carbonyl-D-alanyl radical, it is possible to use a product of the general formula (IX) in which one of the symbols $R_9$ or $R_{10}$ represents a carboxyl radical and the other represents an alkoxycarbonyl radical containing 2 to 5 carbon atoms or a benzyloxycarbonyl radical. Under these conditions, the product of the general formula (VIII) is reacted with the product of the general formula (IX) and then, after replacement of the alkoxycarbonyl or benzyloxycarbonyl radical represented by $R_9$ or $R_{10}$ by a carboxyl radical, the product of the general formula (VIII) which is identical to (or different from) the product of the general formula (VIII) used in the first condensation is reacted again.

According to the present invention, the new peptides of the general formula (I) in which $R_3$ represents a glycyl or D-alanyl radical can be obtained by reacting an aminoacid of the general formula:

in which $R_7$ is defined as above and $R_{11}$ represents a protective group of the amine group, with a tri- or tetra-peptide of the general formula:

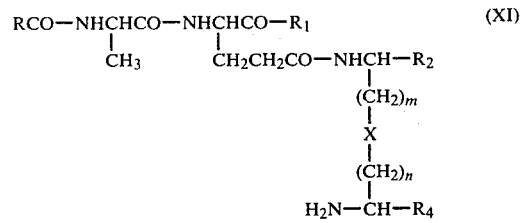

in which R, $R_1$, $R_2$, $R_4$, X, m and n are defined as above, it being excluded for $R_2$ and $R_4$ simultaneously to be an optionally esterified N-carbonyl-glycyl or N-carbonyl-D-alanyl radical, and then replacing $R_{11}$ by a hydrogen atom and, if desired, replacing $R_1$, if it represents a alkoxy radical containing 1 to 4 carbon atoms or a benzyloxy radical, by a hydroxyl radical, and replacing the alkoxycarbonyl radicals containing 2 to 5 carbon atoms or benzyloxycarbonyl radicals, represented or carried by $R_2$ and/or $R_4$, by carboxyl radicals, under the conditions described above for the reaction of a product of the general formula (II) with an acid of the general formula (III).

The dipeptide of the general formula (II) can be obtained by the reaction of an activated derivative of L-alanine, of the general formula:

in which $R_{12}$ represents a radical RCO— in which R is defined as above, or a protective group of the amine group, with a D-glutamic acid derivative of the general formula:

in which $R_5$ is defined as above and the carboxyl group is optionally protected, under the conditions described above for the reaction of a product of the general formula (II) with a product of the general formula (III), this being followed, if necessary, after replacement of the radical $R_{12}$, if it represents a protective group of the amine group, by a hydrogen atom, by reaction with an acid of the general formula (VI) and then by the replacement of the protected carboxyl group by a carboxyl radical.

The lanthionine derivatives, i.e. the products of the general formula (III) in which X represents a sulphur atom and m and n are equal to 1, can be prepared in the following manner:

(a) The lanthionine derivative of the general formula (III) in which $R_2$ and $R_4$ represent a carboxyl radical and $R_6$ represents a benzyloxycarbonyl radical can be prepared in accordance with the method of I. PHOTAKI et al., J. Chem. Soc. Perkin I, 2,599 (1979).

(b) The lanthionine derivative of the general formula (III) in which $R_2$ represents a carboxyl radical, $R_4$ represents a carbamoyl radical and $R_6$ represents a protective group of the amine group or a glycyl or D-alanyl radical of which the amine group is substituted by a protective group of the amine group, in the D,D or L,L form, can be prepared from the corresponding lanthionine, the preparation of which is described by J. GREENSTEIN and M. WINITZ, "Chemistry of the Amino Acids", John Wiley and Sons, 1961, page 2,675. To do this, the dibenzyl ester of dibenzyloxycarbonyllanthionine is prepared in accordance with the known methods and is mono-saponified in accordance with the method described by A. ARENDT et al., Roczniki Chemii Ann. Soc. Chim. Polonorum, 48, 1,305 (1974) [Chem. Abstracts, 82, 31497 g (1975)], and the monosaponified product is then converted, by reaction with ammoniacal methanol, to the monoamide of the general formula:

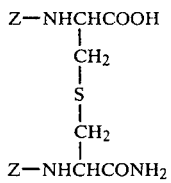
   (XIV)

(in which Z represents a benzyloxycarbonyl radical), which, after acid hydrolysis or hydrogenolysis, yields the monoamide of lanthionine.

By reacting a copper salt, such as cupric bromide or basic copper carbonate, with the monoamide of lanthionine, a complex is formed which can be represented by the formula:

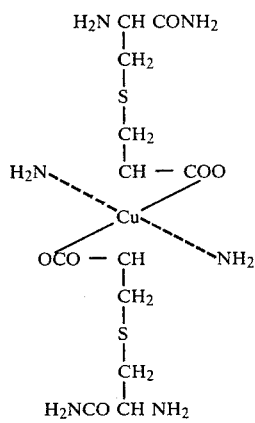
   (XV)

in which the amino radical in the α-position to the carbamoyl group can be acylated by means of an aminoacid of the general formula (X) or protected by reaction with an alkyl or benzyl halogenoformate. The complex formed in this way is dissociated by reaction with hydrogen sulphide in order to give the aminoacid or the dipeptide of the general formula (III) in which $R_2$ represents a carboxyl radical, $R_4$ represents a carbamoyl radical and $R_6$ is defined as above.

(c) The lanthionine derivative of the general formula (III) in which $R_2$ represents a carboxyl radical, $R_4$ represents a carbamoyl radical and $R_6$ represents a protective group of the amine group, in the meso form, the carbon atom which carries the carbamoyl group being in the D form, can be prepared from meso-lanthionine in accordance with the method described in Belgian Pat. No. 821,385 for preparing diaminopimelamic acid.

(d) The lanthionine derivative of the general formula (III) in which $R_2$ represents a carbamoyl radical, $R_4$ represents a carboxyl radical and $R_6$ represents a protective group of the amine group or a glycyl or D-alanyl residue of which the amine group is protected by a protective group of the amine group can be obtained by protecting the amine group in the α-position to the carbamoyl group of the product of the general formula (XV) by reaction with an alkyl or benzyl halogenoformate. The complex formed in this way is dissociated by reaction with hydrogen sulphide in order to give the lanthionine derivative of the general formula (III) in which $R_4$ represents a carbamoyl radical, $R_2$ represents a carboxyl radical and $R_6$ represents a protective group of the amine group. The amino radical in the α-position to the carboxyl group can be protected by a protective group or acylated by reaction with an activated derivative of an aminoacid of the general formula (X). After replacement of the radical $R_6$ by a hydrogen atom, by methods which do not affect the rest of the molecule, the lanthionine derivative of the general formula (III) is obtained in which $R_4$ represents a carboxyl radical, $R_2$ represents a carbamoyl radical and $R_6$ represents a protective group of the amine group or a glycyl or D-alanyl residue of which the amine group is substituted by a protective group of the amine group.

(e) The lanthionine derivative of the general formula (III) in which $R_4$ represents a carbamoyl radical, $R_2$ represents an alkoxycarbonyl radical containing 2 to 5 carbon atoms, a benzyloxycarbonyl radical or an N-carbonylglycyl or N-carbonyl-D-alanyl radical optionally esterified by an alkyl radical containing 1 to 4 carbon atoms or a benzyl radical, and $R_6$ represents a protective group of the amine group or a glycyl or D-alanyl radical of which the amine group is substituted by a protective group of the amine group can be obtained by reacting an aminoacid of the general formula (VIII), or an aliphatic alcohol containing 1 to 4 carbon atoms or benzyl alcohol, with an aminoacid or a dipeptide of the general formula:

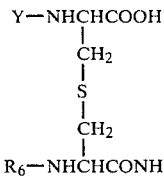
   (XVI)

in which $R_6$ is defined as above and Y represents a protective group of the amine group, the reaction being carried out under the usual conditions, and then replacing the protective group Y by a hydrogen atom and, if desired, replacing the ester group (carried by the glycyl or D-alanyl residue) by a hydroxyl radical, without affecting the rest of the molecule. In particular, it is important to choose Y so that its replacement by a hydrogen atom is carried out without affecting the protective group represented or carried by $R_6$.

(f) The lanthionine derivative of the general formula (III) in which $R_4$ represents a carbamoyl radical, $R_2$ represents an alkoxycarbonyl radical containing 2 to 5 carbon atoms, a benzyloxycarbonyl radical or an optionally esterified N-carbonylglycyl or N-carbonyl-D-alanyl residue, and $R_6$ represents a glycyl or D-alanyl radical of which the amine group is substituted by a protective group of the amine group can be obtained by reacting an aminoacid of the general formula (X) with a product of the general formula:

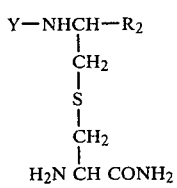
   (XVII)

in which $R_2$ is defined as above and Y represents a protective group of the amine group, the reaction being carried out under the usual conditions, and then replacing Y by a hydrogen atom, without affecting the rest of the molecule.

(g) The lanthionine derivative of the general formula (III) in which $R_2$ represents a carbamoyl radical, $R_4$ represents an alkoxycarbonyl radical containing 2 to 5 carbon atoms, a benzyloxycarbonyl radical or an N-carbonylglycyl or N-carbonyl-D-alanyl radical optionally esterified by an alkyl radical containing 1 to 4 carbon atoms or a benzyl radical, and $R_6$ represents a protective group of the amine group or a glycyl or D-alanyl residue of which the amine group is substituted by a protective group of the amine group can be obtained by reacting an aminoacid of the general formula (VIII), or an aliphatic alcohol containing 1 to 4 carbon atoms or benzyl alcohol, with an aminoacid or a dipeptide of the general formula:

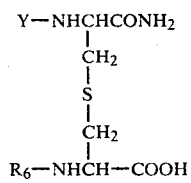
(XVIII)

in which $R_6$ is defined as above and Y represents a protective group of the amine group, the reaction being carried out under the usual conditions, and then replacing the protective group Y by a hydrogen atom and, if appropriate, replacing the ester group carried by the glycyl or D-alanyl residue by a hydroxyl radical, without affecting the rest of the molecule. In particular, it is important to choose Y so that its replacement by a hydrogen atom is carried out without affecting the protective group represented or carried by $R_6$.

If the aminoacid of the general formula (VIII) is reacted with the aminoacid of the general formula (XVI) or (XVIII), the reaction is carried out under conditions which make it possible to create a peptide linkage without affecting the rest of the molecule. If an alcohol (an aliphatic alcohol or benzyl alcohol) is reacted, the reaction is carried out under mild esterification conditions so as not to affect the protective groups Y and $R_6$, and more particularly in accordance with the method of V. BOCCHI, Synthesis, page 961 (1979).

(h) The lanthionine derivative of the general formula (III) in which $R_2$ represents a carbamoyl radical, $R_4$ represents an alkoxycarbonyl or benzyloxycarbonyl radical or an optionally esterified N-carbonylglycyl or N-carbonyl-D-alanyl residue, and $R_6$ represents a glycyl or D-alanyl residue of which the amine group is substituted by a protective group of the amine group can be obtained by reacting an aminoacid of the general formula (X) with an aminoacid or a dipeptide of the general formula:

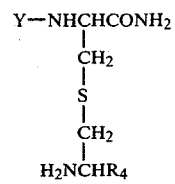
(XIX)

in which $R_4$ is defined as above and Y represents a protective group of the amine group, the reaction being carried out under the usual conditions, and then replacing the group Y by a hydrogen atom without affecting $R_{11}$.

The products of the general formulae (XVII) and (XIX) can be obtained in accordance with the usual methods used in peptide chemistry for the introduction of a protective group of the amine group, starting from a lanthionine derivative of the general formula (III) in which one of the radicals $R_2$ and $R_4$ represents a carbamoyl radical and the other represents an alkoxycarbonyl radical containing 2 to 5 carbon atoms, a benzyloxycarbonyl radical or an optionally esterified N-carbonylglycyl or N-carbonyl-D-alanyl residue, and $R_6$ represents a protective group of the amine group, this being followed by the replacement of the protective group $R_6$ by a hydrogen atom, without affecting the rest of the molecule. In particular, the protective groups of the amine groups of the monoamide of lanthionine are different and are chosen so that the replacement of $R_6$ does not result in the replacement of Y.

(i) The lanthionine derivative of the general formula (III) in which $R_2$ and $R_4$ each represent a carbamoyl radical and $R_6$ represents a protective group of the amine group can be obtained by reacting ammonia with the mixed anhydride, prepared in situ by reacting an alkyl halogenoformate with a lanthionine derivative of the general formula:

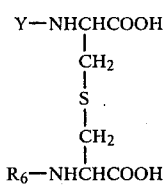
(XX)

in which Y represents a protective group which is different from $R_6$, and then removing the protective group Y without affecting the rest of the molecule.

(j) The lanthionine derivative of the general formula (III) in which $R_2$ and $R_4$ each represent a carbamoyl radical and $R_6$ represents a glycyl or D-alanyl radical of which the amine group is substituted by a protective group can be obtained by reacting an aminoacid of the general formula (X) with the lanthionine derivative of the general formula:

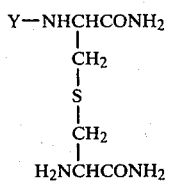
(XXI)

in which Y represents a protective group of the amine group, and then removing the group Y without affecting the protective group carried by $R_6$.

(k) The lanthionine derivative of the general formula (III) in which $R_2$ and $R_4$ each represent an alkoxycarbonyl radical containing 2 to 5 carbon atoms or a benzyloxycarbonyl radical and $R_6$ represents a protective group of the amine group can be obtained by esterifying a lanthionine derivative of the general formula:

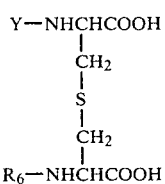 (XXII)

in which Y represents a protective group which is different from $R_6$ defined as above, and then removing Y without affecting the rest of the molecule.

(l) The lanthionine derivative of the general formula (III) in which $R_2$ and $R_4$ each represent an alkoxycarbonyl radical containing 2 to 5 carbon atoms or a benzyloxycarbonyl radical and $R_6$ represents a glycyl or D-alanyl radical of which the amine group is substituted by a protective group of the amine group can be obtained by reacting an aminoacid of the general formula (X) with a lanthionine derivative of the general formula:

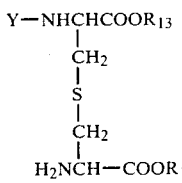 (XXIII)

in which $R_{13}$ represents an alkyl radical containing 1 to 4 carbon atoms or a benzyl radical and Y represents a protective group of the amine group, and then removing Y without affecting the rest of the molecule.

The L-lanthionine derivatives which can be used for the preparation of the products according to the present invention can also be prepared from the diethyl ester of dibenzyloxycarbonyl-L-lanthionine, the preparation of which is described by D. HARPP et al., J. Org. Chem., 36, 73 (1971).

The lanthionine derivatives of the general formula (III) in which one of the symbols $R_2$ or $R_4$ represents a carboxyl or carbamoyl radical, an alkoxycarbonyl radical containing 2 to 5 carbon atoms, a benzyloxycarbonyl radical or an optionally esterified N-carbonylglycyl or N-carbonyl-D-alanyl radical, and the other represents a carboxyl radical, an alkoxycarbonyl radical containing 2 to 5 carbon atoms or a benzyloxycarbonyl radical, and $R_6$ represents a protective group of the amine group or a glycyl or D-alanyl residue of which the amine group is substituted by a protective group can be obtained by reacting a cysteine derivative of the general formula:

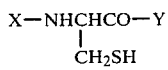 (XXIV)

in which X represents a hydrogen atom, a protective group of the amine group or a glycyl or D-alanyl residue of which the amine group is substituted by a protective group, and Y represents a hydroxyl or amino radical, an alkoxy radical containing 1 to 4 carbon atoms, a benzyloxy radical or an optionally esterified N-glycyl or N-D-alanyl radical, with a product of the general formula:

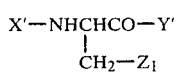 (XXV)

in which X' represents a hydrogen atom or a protective group of the amine group, Y' has the same definition as the symbol Y above and can be different from Y, and $Z_1$ represents a halogen atom other than fluorine, or a reactive ester residue such as a toluenesulphonyl or methanesulphonyl radical, or with a product of the general formula:

 (XXVI)

in which X' and Y' have the definitions given above, and then, if appropriate, removing one of the protective groups X or X' from the amine group of the lanthionine derivative thus obtained.

In general, the product of the general formula (XXIV) is condensed with a product of the general formula (XXV) or (XXVI) in an aqueous-organic medium such as a water/tetrahydrofuran mixture, in the presence of a base (an inorganic base such as sodium hydroxide or potassium hydroxide, or an organic base such as a quaternary ammonium hydroxide), at a temperature of the order of 0° C. The condensation can also be carried out in liquid ammonia.

The condensation of the cysteine derivative of the general formula (XXIV) with the product of the general formula (XXV) can be accompanied by racemisation at the asymmetric carbon atom of the product of the general formula (XXV).

More particularly, the racemisation does not take place if, in the general formulae (XXIV) and (XXV), $Z_1$ represents a halogen atom, Y' represents a hydroxyl radical, Y represents a hydroxyl or amino radical, X represents a hydrogen atom or a benzyloxycarbonyl, t-butoxycarbonyl, t-butoxycarbonylglycyl or t-butoxycarbonyl-D-alanyl radical and X' represents a hydrogen atom or a benzyloxycarbonyl radical. To avoid or limit the racemisation, it is advantageous to carry out the reaction in liquid ammonia.

The thialysine derivatives, i.e. the products of the general formula (III) in which one of the symbols $R_2$ or $R_4$ represents a hydrogen atom, X represents a sulphur atom and m and n are equal to 1, can be obtained from thialysine, the preparation of which is described by D. HOPE et al., J. Chem. Soc. (C), 1,098 (1966), in accordance with the methods given above for the preparation of the lanthionine derivatives.

The cystathionine derivatives, i.e. the products of the general formula (III) in which X represents a sulphur atom, m is equal to 1 and n is equal to 2, the symbols $R_2$ and $R_4$ being different from a hydrogen atom, can be obtained from the cystathionine derivatives, the preparation of which is described in particular by K. JOST et al., Coll. Czech. Chem. Comm., 32, 2,485 (1967), and by Z. PROCHAZKA et al., Coll. Czech. Chem. Comm., 45, 1,982 (1980), in accordance with the methods given above for the preparation of the lanthionine derivatives.

The 2,7-diaminosuberic acid derivatives, i.e. the products of the general formula (III) in which X represents a methylene radical and one of the symbols m and n is equal to 1 and the other is equal to 2, the symbols $R_2$ and $R_4$ being different from a hydrogen atom, can be obtained from the 2,7-diaminosuberic acid derivatives, the preparation of which is described in J. Org. Chem., 45, 3,078 (1980), in accordance with the methods given above for the preparation of the lanthionine derivatives.

The homolanthionine derivatives can be prepared from homolanthionine (S. WEISS and J. STEKOL, J. Amer. Chem. Soc. 73, 2497 (1951)) in accordance with the methods given for the preparation of lanthionine derivatives.

The aminoacid of the general formula (IV) can be obtained by reacting an acid of the general formula (VI), or an activated derivative of this acid, with L-alanine of which the acid group is optionally protected in the form of an ester, and then, if desired, replacing the ester group by the carboxyl group, the reaction being carried out under the conditions indicated above for the reaction of the acid of the general formula (VI) with the peptide of the general formula (VII).

The peptide of the general formula (V) can be obtained by reacting a D-glutamic acid derivative of the general formula (XIII) of which the amine group is protected and in which $R_5$ represents an amino radical, an alkoxy radical containing 1 to 4 carbon atoms or a benzyloxy radical, under the usual conditions, with a product of the general formula (III) in which $R_2$, $R_4$, $R_6$, X, m and n are defined as above, and then, if desired, replacing the radical $R_5$, if it represents an alkoxy radical containing 1 to 4 carbon atoms or a benzyloxy radical, by a hydroxyl radical, and replacing the alkoxycarbonyl radicals containing 2 to 5 carbon atoms or benzyloxycarbonyl radicals, represented or carried by $R_2$ and/or $R_4$, by carboxyl radicals, without affecting the rest of the molecule. However, if $R_5$ forms an ester group with the carbonyl group to which it is bonded, and $R_2$ and/or $R_4$ represent or contain an ester group, it may be necessary for the ester groups represented or carried by $R_5$, $R_2$ and/or $R_4$ to be different and chosen so that the replacement of one of the radicals $R_2$ or $R_4$ by a carboxyl radical is carried out without affecting the radical $R_5$ and the other radical $R_2$ or $R_4$.

The peptide of the general formula (VII) can be obtained by reacting an activated derivative of L-alanine, of the general formula:

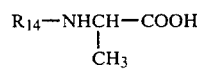 (XXVII)

in which $R_{14}$ represents a protective group of the amine group, under the usual conditions, with a peptide of the general formula (V) in which $R_1$, $R_2$, $R_4$, $R_6$, X, m and n are defined as above, and then replacing the radical $R_{14}$ by a hydrogen atom and, if desired, replacing the radical $R_1$, if it represents an alkoxy radical containing 1 to 4 carbon atoms or a benzyloxy radical, by a hydroxyl radical, and replacing the alkoxycarbonyl radicals containing 2 to 5 carbon atoms or benzyloxycarbonyl radicals by carboxyl radicals, without affecting the rest of the molecule.

If $R_1$, $R_2$ and $R_4$ form or contain an ester group, it is possible for these groups to be different and chosen so that the replacement of one of the radicals $R_2$ or $R_4$ by a carboxyl radical is carried out without affecting the radical $R_1$ and the other radical $R_2$ or $R_4$.

The peptide of the general formula (IX) in which R, $R_5$, $R_6$, $R_9$, $R_{10}$, X, m and n are defined as above can be obtained by reacting a dipeptide of the general formula (II) in which R and $R_5$ are defined as above, under the usual conditions, with a product of the general formula (III) in which $R_6$ is defined as above and $R_2$ and $R_4$ have the definitions given for $R_9$ and $R_{10}$, and then, if necessary, replacing the radicals $R_2$ and/or $R_4$, if they represent an alkoxycarbonyl radical containing 2 to 5 carbon atoms or a benzyloxycarbonyl radical, by a carboxyl radical, without affecting the rest of the molecule.

In particular, if $R_5$ forms an ester group with the carbonyl group to which it is bonded, and $R_2$ and/or $R_4$ represent an ester group, it may be necessary for the radicals $R_5$, $R_2$ and $R_4$ to be different and chosen so that the replacement of the radicals $R_2$ and/or $R_4$ by a carboxyl radical is carried out without affecting the radical $R_5$ and, if appropriate, one of the radicals $R_2$ or $R_4$.

The peptide of the general formula (XI) in which $R_1$ represents a hydroxyl or amino radical, an alkoxy radical containing 1 to 4 carbon atoms or a benzyloxy radical and the symbols $R_2$ and $R_4$ are defined as above can be obtained by reacting a dipeptide of the general formula (II) in which R and $R_5$ are defined as above, under the usual conditions, with an aminoacid of the general formula (III) in which $R_2$ and $R_4$ are defined as above and $R_6$ represents a protective group of the amine group, and then replacing this protective group by a hydrogen atom without affecting the rest of the molecule.

According to the invention, the products of the general formula (I) can also be obtained by the reaction of a product of the general formula:

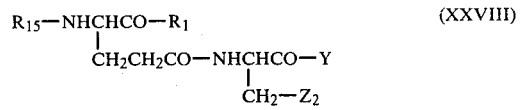 (XXVIII)

in which $R_1$ is defined as above, $R_{15}$ represents a protective group of the amine group or an L-alanyl residue of which the amine group is substituted by a protective group of the amine group or by a fatty acid residue, Y is defined as above and $Z_2$ represents a group —SH, a halogen atom other than fluorine or a reactive ester residue such as a toluenesulphonyl or methanesulphonyl radical, with a product of the general formula:

 (XXIX)

in which $X_1$ represents a hydrogen atom, a protective group of the amine group or a glycyl or D-alanyl residue of which the amine group is optionally substituted by a protective group of the amine group, $Y_1$ represents a hydroxyl radical, an alkoxy radical containing 1 to 4 carbon atoms, a benzyloxy radical or an optionally esterified N-glycyl or N-D-alanyl radical and $Z'_2$ has the same definition as $Z_2$, it being understood that one of the symbols $Z_2$ or $Z'_2$ represents a radical —SH and that if $Z'_2$ represents a toluenesulphonyl or methanesulphonyl radical, $X_1$ is different from a glycyl or D-alanyl residue, under the conditions described above for the reaction of a product of the general formula (XXIV) with a product of the general formula (XXV), this being followed, if $R_{15}$ represents a protective group of the amine group, by the replacement of this protective group by a hydrogen atom without affecting the rest of the molecule, and by reaction with an L-alanine derivative of which the amine group is substituted by a fatty acid residue or a protective group of the amine group, and, in the latter case, by reaction with the acid of the general formula (VI) after removal of this protective group, and, if $R_{15}$ represents an L-alanyl residue of which the amine group is substituted by a protective group of the amine group, by reaction with an acid of the general formula (VI) after removal of this protective group, and then, if necessary, by the removal of the protective groups represented or carried by $R_1$, Y, $X_1$ and $Y_1$, without affecting the rest of the molecule.

The present invention also relates to a process for the preparation of the products of the general formula (I) by Merrifield's peptide synthesis in the solid phase.

The process essentially consists in fixing, to a suitable support, an aminoacid or a peptide of the general formula:

in which X, m and n are defined as above, one of the symbols $R_2$ or $R_4$ represents a carboxyl, N-carbonylglycyl or N-carbonyl-D-alanyl radical and the other represents a hydrogen atom, a carbamoyl radical, an alkoxycarbonyl radical containing 2 to 5 carbon atoms, a benzyloxycarbonyl radical or an N-carbonylglycyl or N-carbonyl-D-alanyl radical esterified by an alkyl radical containing 1 to 4 carbon atoms or a benzyl radical, $R_{16}$ represents a protective group of the amine group or a glycyl or D-alanyl radical of which the amine group is substituted by a protective group of the amine group, and $R_{17}$ represents a protective group of the amine group, it being understood that the protective groups of the amine group, represented or carried by $R_{17}$ and $R_{16}$, are different, and then, after the unblocking of the amine group protected by $R_{17}$, in condensing:

either D-glutamic acid of which the amine and α-carboxyl groups are suitably protected, i.e. the product of the general formula:

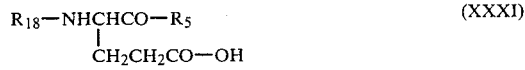

in which $R_{18}$ represents a protective group of the amine group which is different from $R_{16}$, and $R_5$ represents an amino radical, an alkoxy radical containing 1 to 4 carbon atoms or a benzyloxy radical, and then, after the unblocking of the amine group protected by the radical $R_{18}$, without affecting $R_{16}$, either an L-alanine derivative of the general formula (XXVII), and then, after the unblocking of the amine group protected by $R_{14}$, it being understood that $R_{14}$ is different from $R_{16}$, the acid of the general formula (VI).

or an L-alanine derivative of the general formula (IV), or the dipeptide of the general formula:

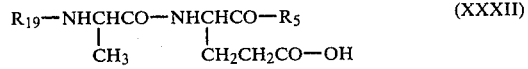

in which $R_5$ is defined as above and $R_{19}$ represents a fatty acid residue or a protective group of the amine group, it being understood that if $R_{19}$ represents a protective group of the amine group, it is different from the protective group $R_{16}$ of the product of the general formula (XXX), and that the acid of the general formula (VI) is then reacted, if appropriate, after the unblocking of the amine group protected by the radical $R_{19}$, and then in separating the product obtained from its support and, if necessary, in removing the protective groups of the amine and carboxyl groups.

According to a variant of the process, it is possible to fix, to a suitable support, the peptide of the general formula:

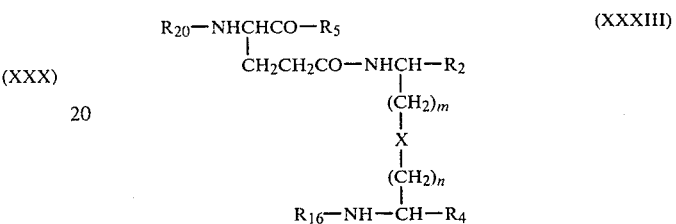

in which $R_5$, $R_{16}$, X, m and n are defined as above, one of the symbols $R_2$ or $R_4$ represents a carboxyl, N-carbonylglycyl or N-carbonyl-D-alanyl radical and the other represents a hydrogen atom, a carbamoyl radical, an alkoxycarbonyl radical containing 2 to 5 carbon atoms, a benzyloxycarbonyl radical or an N-carbonylglycyl or N-carbonyl-D-alanyl radical esterified by an alkyl radical containing 1 to 4 carbon atoms or a benzyl radical, and $R_{20}$ represents a protective group of the amine group, it being understood that the protective groups of the amine group, represented or carried by $R_{16}$ and $R_{20}$, are different, and then, after the unblocking of the amine group protected by $R_{20}$, to condense:

either an L-alanine derivative of the general formula (XXVII), and then, after the unblocking of the amine group protected by $R_{14}$, the fatty acid of the general formula (VI), or an L-alanine derivative of the general formula (IV), and then to separate the product obtained from its support and, if necessary, to remove the protective groups of the amine and carboxyl groups.

According to another variant of the process, it is possible to fix, to a suitable support, the peptide of the general formula:

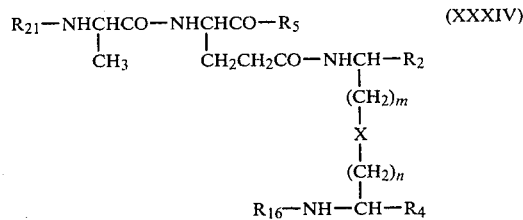

in which $R_5$, $R_{16}$, X, m and n are defined as above, one of the symbols $R_2$ or $R_4$ represents a carboxyl, N-carbonylglycyl or N-carbonyl-D-alanyl radical and the other represents a hydrogen atom, a carbamoyl radical, an alkoxycarbonyl radical containing 2 to 5 carbon atoms, a benzyloxycarbonyl radical or an N-carbonylglycyl or N-carbonyl-D-alanyl radical esterified by an alkyl radical containing 1 to 4 carbon atoms or a benzyl radical, and $R_{21}$ represents a protective group of the amine group which is different from the protective group of the amine group represented or carried by $R_{16}$, and then, after the unblocking of the amine group protected by $R_{21}$, to condense the acid of the general formula (VI) and then to separate the product obtained from its support and, if necessary, to remove the protective groups of the amine and carboxyl groups.

Merrifield's peptide synthesis can also be carried out by fixing, to a suitable support, a product of the general formula (XXXI) or (XXXII), in which formulae $R_5$ represents a hydroxyl radical, the symbols $R_{18}$ and $R_{19}$ are respectively defined as above and the γ-carboxyl radical is protected, and then, after the unblocking of this protective group, followed by activation of the acid group, by reacting the product of the general formula (XXX) of which the amine and carboxyl groups are suitably protected, and then, if necessary, depending on the meanings of $R_{18}$ and $R_{19}$, an acid of the general formula (VI) or the L-alanine derivative of the general formula (XXVII), and, if appropriate, depending on the meaning of $R_{14}$, the acid of the general formula (VI).

If one of the symbols $R_2$ or $R_4$ in the general formula (I) represents an N-carbonylglycyl or N-carbonyl-D-alanyl radical and the other represents a hydrogen atom, a carboxyl or carbamoyl radical, an alkoxycarbonyl radical containing 2 to 5 carbon atoms, a benzyloxycarbonyl radical or an N-carbonylglycyl or N-carbonyl-D-alanyl radical optionally esterified by an alkyl radical containing 1 to 4 carbon atoms or a benzyl radical, it is possible to fix, to a suitable support, glycine or D-alanine of which the amine group is protected, and then, after the unblocking of the amine group, to condense an aminoacid or a peptide of the general formula:

(XXXV)

in which $R_{16}$, X, m and n are defined as above, one of the symbols $R_2$ or $R_4$ represents a carboxyl radical and the other represents a hydrogen atom, a carbamoyl radical, an alkoxycarbonyl radical containing 2 to 5 carbon atoms, a benzyloxycarbonyl radical or an N-carbonylglycyl or N-carbonyl-D-alanyl radical esterified by an alkyl radical containing 1 to 4 carbon atoms or a benzyl radical, and $R_{22}$ represents a protective group of the amine group which is different from $R_{16}$, or a D-aminoacid residue of the general formula:

(XXXVI)

in which $R_5$ is defined as above and $R_{23}$ represents a protective group of the amine group which is different from $R_{16}$, or an L-aminoacid residue of the general formula:

$$R_{24}-NHCH-COOH \atop CH_3 \quad (XXXVII)$$

in which $R_{24}$ represents a protective group of the amine group or a fatty acid residue defined above, it being understood that the protective groups represented by $R_{22}$, $R_{23}$ and $R_{24}$ are different from $R_{16}$ and can be removed without affecting the latter, and then, if $R_{22}$ represents a protective group of the amine group, to remove this protective group and then to condense either a D-glutamic acid derivative of the general formula (XXXVI) in which $R_{23}$ represents a protective group of the amine group, and then, after the removal of $R_{23}$, to condense an L-alanine derivative of the general formula (XXXVII) in which $R_{24}$ is defined as above and, if $R_{24}$ represents a protective group of the amine group, to remove the radical $R_{24}$ and then to condense the acid of the general formula (VI), or a D-glutamic acid derivative of the general formula (XXXVI) in which $R_{23}$ represents an L-aminoacid residue of the general formula (XXXVII) in which $R_{24}$ is defined as above, and, if $R_{24}$ represents a protective group of the amine group, to remove the radical $R_{24}$ and then to condense the fatty acid of the general formula (VI), if $R_{22}$ represents an aminoacid residue of the general formula (XXXVI) in which $R_{23}$ represents a protective group of the amine group, to remove this protective group and then to condense an L-alanine derivative of the general formula (XXXVII) in which $R_{24}$ is defined as above, and, if $R_{24}$ represents a protective group of the amine group, to remove the radical $R_{24}$ and then to condense the fatty acid of the general formula (VI), and if $R_{22}$ represents an aminoacid residue of the general formula (XXXVI) in which $R_{23}$ represents an L-aminoacid residue of the general formula (XXVII) in which $R_{24}$ represents a protective group of the amine group, to remove the radical $R_{24}$ and then to condense the fatty acid of the general formula (VI).

If $R_3$ in the general formula (I) represents a glycyl or D-alanyl residue, this radical can be introduced at any stage of the Merrifield synthesis. It is possible e.g. to fix, to a suitable support, the product of the general formula (XXX) in which $R_{16}$ represents a protective group of the amine group which is different from $R_{17}$, and then to remove $R_{16}$ without affecting $R_{17}$ and to condense a glycine or D-alanine derivative of which the amine group is substituted by a protective group of the amine group which is different from $R_{17}$, and then, after the removal of $R_{17}$, to condense the product of the general formula (XXXI) or (XXXII) under the conditions indicated above, or alternatively it is possible to fix, to a suitable support, the product of the general formula (XXX) in which $R_{16}$ represents a protective group of the amine group, and then to condense a product of the general formula (XXXI) or (XXXII) under the conditions indicated above, and then, after the removal of $R_{16}$, to condense glycine or D-alanine of which the amine group is substituted by a protective group.

Particularly suitable supports are chloromethylated or hydroxymethylated styrene/divinylbenzene copolymers. Chloromethylated styrene/divinylbenzene copolymer (98/2 or 99/1) is preferably used.

The peptides of the general formula (XXX), (XXXI), (XXXII), (XXXIII) or (XXXIV) are fixed to the chloromethylated support in accordance with the usual methods, in particular by reacting the peptide of the general formula (XXX), (XXXI), (XXXII), (XXXIII) or (XXXIV) in solution in an organic solvent such as ethanol, and in the presence of an acid acceptor such as triethylamine. It is particularly advantageous to heat the reaction mixture to a temperature near the b.p. of the reaction mixture.

The protective groups of the amine groups of the peptides of the general formula (XXX), (XXXI), (XXXII), (XXXIII) or (XXXIV) must be chosen so that their removal is carried out without affecting the peptide-support linkage. In particular, the radicals $R_{17}$, $R_{18}$, $R_{19}$, $R_{20}$ and $R_{21}$ must be different from the radical $R_{16}$ and be such that their removal is carried out without affecting the protective group $R_{16}$ and the peptide-support linkage.

In general, the ester groups represented or carried by $R_2$, $R_4$ or $R_5$ are chosen so that, during the scission of the peptide-support linkage, the radicals $R_2$, $R_4$ or $R_5$ can be either preserved or converted to carboxyl or carbamoyl radicals, depending on whether the scission is acid hydrolysis, alcoholysis or ammonolysis.

More particularly, the peptide-support linkage, which is benzylic in nature, is cleaved by treatment with a hydrobromic acid/trifluoroacetic acid mixture, an acid group being regenerated.

If necessary, the new peptides of the general formula (I) can be purified by physical methods (such as crystallisation or chromatography) or chemical methods (such as the formation of a salt, crystallisation of the latter and then decomposition).

The new products according to the invention can be converted by known methods into addition salts with acids, into metal salts or into addition salts with organic bases, depending on the nature of the substituents.

The addition salts with acids can be obtained by reacting the new products with acids in a suitable solvent. In general, the product is solubilised in water by adding the theoretical amount of acid, and the solution obtained is then lyophilised.

The metal salts or the addition salts with organic bases can be obtained by reacting the new compounds with inorganic or organic bases in a suitable solvent. In general, the product is solubilised in water by adding the theoretical amount of base, and the solution obtained is then lyophilised.

Preferably the salts of compounds of general formula I are non-toxic salts, i.e. salts the cations, or in the case of acid addition salts, the anions, of which are relatively innocuous to the animal organism in therapeutic doses of the salts so that the beneficial physiological properties inherent in the compounds of general formula I are not vitiated by side effects ascribable to the cations or anions.

Suitable acid addition salts are, for example, the hydrochlorides, sulphates, nitrates, phosphates, acetates, propionates, succinates, benzoates, fumarates, maleates, theophylline-acetates, salicylates, phenolphthalinates and methylene-bis-β-hydroxynaphthoates.

The new compounds according to the present invention are useful as vaccine adjuvants and immunostimulants; they increase the hypersensitivity reactions and/or the production of circulating antibodies against the antigens with which they are administered, and they stimulate, in a non-specific manner, defence reactions against certain infections (e.g. the infection caused in mice by the intra-cellular bacterium Listeria monocytogenes).

Of very particular value are the products of the general formula (I) in which RCO- represents a fatty acid residue in which R represents an alkyl radical containing 2 to 21 carbon atoms, which is optionally substituted by a hydroxyl radical, $R_1$ represents a hydroxyl or amino radical, the symbols $R_2$ and $R_4$, which are identical or different, represent a hydrogen atom or a carboxyl, carbamoyl, N-carbonylglycyl or N-carbonyl-D-alanyl radical, it being understood that $R_2$ and $R_4$ cannot simultaneously represent a hydrogen atom, $R_3$ represents a hydrogen atom or a glycyl or D-alanyl residue, it being understood that if $R_2$ and $R_4$, which are identical or different, each represent an N-carbonylglycyl or N-carbonyl-D-alanyl radical, $R_3$ represents a hydrogen atom, X represents a sulphur atom and m and n, which are identical or different, each represent an integer equal to 1 or 2, it being understood that the alanine bonded to the glutamic acid is in the L form, the glutamic acid is in the D form, the lanthionine, if m and n are equal to 1, the cystathionine, if m and n are different, and the homolanthionine, if m and n are equal to 2, are in the D,D, L,L, D,D/L,L (racemic) or D,L (meso) form or in the form of L/meso or D/meso mixtures, and the thialysine, if one of the symbols $R_2$ or $R_4$ represents a hydrogen atom, and m and n are equal to 1, is in the L, D or D,L form.

It is to be understood that in this specification and the accompanying claims alkyl radicals and moieties may be straight- or branched- chain.

By the expression "known methods" as used in this specification and the accompanying claims is meant methods heretofore used or described in the literature.

In vitro, the new peptides are active at molar concentrations which are generally between $10^{-3}$ and $10^{-8}$, in particular in the following tests:

stimulating the synthesis of DNA (mitogenic power) in accordance with the technique of G. MARCHAL, Ann. Immunol. (Inst. Pasteur), 125 C, 519 (1974), stimulating the production of antibodies in accordance with the technique of P. H. KLESIUS, Proc. Soc. Exp. Biol. Med. (N.Y.), 135, 155 (1970), and H. VAN DIJK and N. BLOKSMA, J. Immunol. Methods, 14, 325 (1977), increasing the number of phagocytic macrophages in accordance with the technique of J. MICHL et al., J. Exp. Med., 144, 1,465 (1976), and increasing the cytostatic activity of the macrophages of a peritoneal exudate towards the tumoral cells.

In vivo, in mice, at doses of between 1 and 30 mg/kg, they increase the delayed hypersensitivity and the production of antibodies, in particular in accordance with the technique of T. E. MILLER et al., J. Nat. Cancer Inst., 51, 1,669 (1973).

In mice, at doses of between 1 and 100 mg/kg, they stimulate the defence reactions against the infection caused either by Listeria monocytogenes or by Klebsiella pneumoniae, in accordance with the technique of R. M. FAUVE and B. HEVIN, C.R. Acad. Sci. (D), 285, 1,589 (1977).

In mice, they stimulate the ability of the reticuloendothelial system to take up colloidal carbon, in accordance with the technique of B. N. HALPERN et al., Ann. Institut Pasteur, 80, 582 (1951).

The following Examples illustrate the present invention.

The products according to the present invention can form complexes with alkali metals or alkaline earth metals; consequently, the results of elementary analysis of the products can deviate substantially from the theoretical values. However, the structure of the products is confirmed by the C/N or C/S ratio, which is in agreement with theory, by the proportion of aminoacids and by their homogeneity in silica gel thin layer chromatography.

The hydrolysis conditions used for determining the ratio of the aminoacids to one another [concentrated hydrochloric acid/anhydrous acetic acid (1/1 by volume) at 96° C. for 5 hours, in accordance with the method of I. PHOTAKI, J. Chem. Soc., Perkin I, 2,599 (1979)] are conditions which do not racemise the lanthionine, but are not sufficient to produce a complete break in the amide linkage between the fatty acid and the alanine.

EXAMPLE 1

Isobutyl chloroformate (1 cc) is added to a solution, kept at −5° C., of benzyl N-(N-lauroyl-L-alanyl)-α-D-glutamate (3.9 g) in a mixture of tetrahydrofuran (200 cc) and triethylamine (1.1 cc). The mixture is stirred for 40 minutes at −5° C. and a solution, cooled to 0° C., of N-α-benzyloxycarbonyl-L-lanthionine (2.7 g) in 0.1 N sodium hydroxide solution (158 cc) is then added. The reaction mixture is stirred for 20 minutes at 0° C. and then for 16 hours at about 20° C. The tetrahydrofuran is evaporated off by concentration under reduced pressure (20 mm Hg; 2.7 kPa) at 50° C.; the concentrate is acidified to pH 2 by adding 1 N hydrochloric acid (about 30 cc) and extracted 3 times with ethyl acetate (300 cc in total). The combined organic phases are washed with a saturated solution of sodium chloride (50 cc), dried over anhydrous sodium sulphate and concentrated to dryness under reduced pressure (20 mm hg: 2.7 kPa) at 40° C. The residue obtained is triturated in ether (200 cc), filtered off and dried under reduced pressure (20 mm Hg; 2.7 kPa) at 20° C. This yields an amorphous powder (2.25 g) to which a similar product (0.45 g) obtained in another preparation is added. This mixture is chromatographed on neutral silica gel (0.04–0.063 mm) (50 g) contained in a column of diameter 2.3 cm. To do this, the product (2.70 g) is dissolved in boiling ethyl acetate (200 cc), and neutral silica gel (0.04–0.063 mm) (5 g) is added to the solution obtained. The mixture is evaporated to dryness under reduced pressure (20 mm Hg; 2.7 kPa) at 50° C. and the residue thus obtained is charged onto the silica column. Elution is carried out successively with an ethyl acetate/cyclohexane mixture (2/8 by volume) (300 cc), an ethyl acetate/cyclohexane mixture (1/1 by volume) (150 cc), an ethyl acetate/cyclohexane mixture (3/1 by volume) (750 cc), ethyl acetate (1.2 liters), an ethyl acetate/acetic acid mixture (9/1 by volume) (850 cc) and an ethyl acetate/acetic acid mixture (8/2 by volume) (250 cc), 50 cc fractions being collected. Fractions 51 to 70 are combined and concentrated to dryness under reduced pressure (20 mm Hg; 2.7 kPa) at 50° C. The residue is triturated in ether (200 cc), filtered off, washed twice with ether (100 cc in total) and dried under reduced pressure (0.3 mm Hg; 0.04 kPa) at 50° C. This yields $N^2$-[$O^1$-benzyl-N-(N-lauroyl-L-alanyl)-γ-D-glutamyl]-$N^6$-benzyloxycarbonyl-L,L-2,6-diamino-4-thiapimelic acid (1.86 g).

Rf=0.45 [silica gel; ethyl acetate/acetic acid (9/1 by volume)].

A stream of hydrogen bromide is passed into a solution of $N^2$-[$O^1$-benzyl-N-(N-lauroyl-L-alanyl)-γ-D-glutamyl]-$N^6$-benzyloxycarbonyl-L,L-2,6-diamino-4-thiapimelic acid (1.8 g) in trifluoroacetic acid (50 cc) for 5½ hours. The reaction mixture is then purged with nitrogen for 10 minutes, a small amount of insoluble material is removed by filtration and the filtrate is concentrated to dryness under reduced pressure (20 mm Hg; 2.7 kPa) at 50° C. The residue obtained is triturated in ethyl acetate (50 cc), filtered off and washed twice with ether (60 cc in total). This yields a very hygroscopic, amorphous powder (1.06 g) which is dissolved in a 1.9 N anhydrous solution of hydrogen chloride in acetic acid (50 cc). This solution is concentrated to dryness under reduced pressure (20 mm Hg; 2.7 kPa) at 50° C. The residue is dissolved in anhydrous acetic acid (5 cc) and the solution is poured into ether (1 liter). The precipitate formed in this way is filtered off, washed with ether (100 cc), dried under reduced pressure (0.3 mm Hg; 0.04 kPa) at 20° C. and dissolved in water (10 cc). The solution thus obtained gels after ½ hour; it is then diluted with water (500 cc). The precipitate formed in this way is filtered off and dissolved in acetic acid (5 cc) and the solution is poured into ether (800 cc). The new precipitate formed in this way is filtered off, washed 3 times with ether (300 cc in total) and dried under reduced pressure (0.3 mm Hg; 0.04 kPa) at 50° C. This yields $N^2$-[N-(N-lauroyl-L-alanyl)-γ-D-glutamyl]-L,L-2,6-diamino-4-thiapimelic acid (380 mg) containing 2.1% of water.

Rf=0.25 [silica gel; n-butanol/pyridine/acetic acid/water (50/20/6/24 by volume)].

Analysis: Calculated % C 52.87; H 7.85; N, 9.48; S 5.43. Found % C 49.5; H 7.9; N 8.7; S 5.2.

Sulphuric ash: 2.1%.

After hydrolysis in a concentrated hydrochloric acid/anhydrous acetic acid mixture (1/1 by volume) for 5 hours at 96° C., analysis on a BIOTRONIK autoanalyser shows the presence of the following aminoacids:

Lan 1.00 (theory=1)
meso Lan 0 (theory=0)
Glu 1.02 (theory=1)

N-α-Benzyloxycarbonyl-L-lanthionine can be prepared in accordance with the method of I. PHOTAKI et al., J. Chem. Soc. Perkin I, 2,599 (1979).

Benzyl N-lauroyl-L-alanyl-α-D-glutamate can be prepared in accordance with one of the following two methods:

(a) Lauroyl chloride (8 g) dissolved in ether (75 cc) is added, in the course of 37 minutes, to a solution of benzyl L-alanyl-α-D-glutamate hydrochloride (12.75 g) in 1 N sodium hydroxide solution (75 cc), and 1 N sodium hydroxide solution (37.4 cc) is added simultaneously so as to keep the pH of the reaction mixture between 8 and 9. The mixture is stirred for 1 hour 20 minutes. After decantation, the aqueous phase is acidified to pH 2 by adding 1 N hydrochloric acid (60 cc) and extracted 3 times with ethyl acetate (300 cc in total). The combined organic extracts are washed with water (25 cc), dried over anhydrous sodium sulphate and concentrated to dryness under reduced pressure (20 mm Hg; 2.7 kPa) at 45° C. This yields a white solid (7.4 g) which is chromatographed on neutral silica gel (80 g) contained in a column of diameter 2 cm. Elution is carried out successively with an ethyl acetate/methanol mixture (8/2 by volume) (100 cc) and an ethyl acetate/methanol mixture (1/1 by volume) (200 cc), 50 cc fractions being collected. Fraction 1 is concentrated to dryness under reduced pressure (20 mm Hg; 2.7 kPa) at 45° C. This yields benzyl N-lauroyl-L-alanyl-α-D-glutamate (2 g), which melts at 130° C. Fractions 2 to 4 are likewise concentrated to dryness and chromatographed on neutral silica gel (0.063–0.20 mm) (100 g) contained in a column of diameter 2 cm. Elution is carried out with acetone (250 cc), 25 cc fractions being collected. Fractions 1 and 2 are concentrated to dryness under reduced pressure (20 mm Hg; 2.7 kPa) at 45° C. This yields benzyl N-lauroyl-L-alanyl-α-D-glutamate (4.07 g), which melts at 130° C. and has the following characteristics:

Rf=0.9 [silica gel; n-butanol/pyridine/acetic acid/water (50/20/6/24 by volume)].

Analysis: Calculated % C 66.10; H 8.63; N 5.71. Found % C 66.3; H 8.8; N 5.6.

(b) Isobutyl chloroformate (31 cc) is added to a solution, kept at a temperature of the order of 10° C., of lauric acid (47.75 g) in dioxane (3 liters) and triethylamine (33.3 cc). The mixture is stirred for 20 minutes at 10° C. and a solution, cooled to 10° C., of benzyl L-alanyl-α-D-glutamate hydrochloride (88.95 g) in a mixture of dioxane (1 liter), water (476 cc) and 1 N sodium hydroxide solution (476 cc) is then added in the course of 10 minutes. The reaction mixture is stirred for 1 hour at 10° C. and then for 18 hours at a temperature of the order of 20° C.; it is then diluted by adding water (4 liters), acidified to pH 2 by adding 1 N hydrochloric acid (about 475 cc) and kept for 2 hours at 0° C. The precipitate obtained is filtered off, washed successively with water (500 cc) and ether (500 cc) and then dried under reduced pressure (20 mm Hg; 2.7 kPa) at 20° C. The product is suspended in ether (800 cc), the suspension is stirred for 1 hour and the product is filtered off and washed twice with ether (200 cc in total). After drying under reduced pressure (20 mm Hg; 2.7 kPa) at 20° C., benzyl N-lauroyl-L-alanyl-α-D-glutamate (71.79 g) is obtained, which melts at 130° C.

Rf=0.77 [silica gel; ethyl acetate/methanol (4/1 by volume)].

Benzyl L-alanyl-α-D-glutamate hydrochloride can be prepared in the following manner:

Benzyl N-t-butoxycarbonyl-L-alanyl-α-D-glutamate (97.16 g) is dissolved in a 1.7 N anhydrous solution of hydrogen chloride in acetic acid (970 cc). The solution is stirred for 2 hours, anhydrous ether (3.8 liters) is then added rapidly and the mixture is left to stand for 2 hours at 0° C. The oily precipitate which has formed is separated from the supernatant by decantation and dissolved in acetone (500 cc); the solution thus obtained is concentrated to dryness under reduced pressure (20 mm Hg; 2.7 kPa) at 50° C. This yields benzyl L-alanyl-α-D-glutamate hydrochloride (88.9 g).

Benzyl N-t-butoxycarbonyl-L-alanyl-α-D-glutamate can be prepared in accordance with the method of E. BRICAS et al., Biochemistry 9, 823 (1970).

EXAMPLE 2

Isobutyl chloroformate (2.6 cc) is added to a solution, kept at −5° C., of t-butyl N-(N-lauroyl-L-alanyl)-α-D-glutamate (9.12 g) in a mixture of tetrahydrofuran (440 cc) and triethylamine (2.8 cc). The mixture is stirred for 20 minutes at −5° C. and a solution, cooled to 2° C., of $N^6$-benzyloxycarbonyl-2(L),6(D,L)-diamino-4-thiapimelamic acid (6.82 g) in a mixture of 1 N sodium hydroxide solution (20 cc) and water (172 cc) is then added.

The reaction mixture is stirred for 5 minutes at 0° C. and then for 20 hours at about 20° C. The tetrahydrofuran is evaporated off by concentration under reduced pressure (20 mm Hg; 2.7 kPa) at 50° C.; the concentrate is cooled to 0° C. and acidified to pH 2 by adding 1 N hydrochloric acid (about 23 cc). The precipitate formed is filtered off, washed with 0.1 N hydrochloric acid (100 cc) and then twice with water (400 cc in total) and dried in the open air. This yields a slightly green-coloured powder (11.8 g), which is chromatographed on neutral silica gel (0.04–0.063 mm) (250 g) contained in a column of diameter 4 cm. To do this, the powder (11.8 g) is disslved in acetic acid (150 cc), and neutral silica gel (0.04–0.063 mm) (20 g) is added to the solution obtained. The mixture is evaporated to dryness under reduced pressure (20 mm Hg) at 50° C. and the residue thus obtained is charged onto the silica column. Elution is carried out successively with an ethyl acetate/acetic acid mixture (98/2 by volume) (1 liter) and an ethyl acetate/acetic acid mixture (9/1 by volume) (3.2 liters), 100 cc fractions being collected. Fractions 17 to 42 are combined and concentrated to dryness under reduced pressure (20 mm Hg) at 50° C. The residue obtained is triturated in ether (150 cc), filtered off and dried. This yields $N^2$-[$O^1$-t-butyl-N-(N-lauroyl-L-alanyl)-γ-D-glutamyl]-$N^6$-benzyloxycarbonyl-2(L),6(D,L)-diamino-4-thiapimelamic acid (6.3 g).

Rf=0.83 [silica gel; acetic acid/ethyl acetate (3/1 by volume)].

Rf=0.63 [silica gel; n-butanol/pyridine/acetic acid/water(50/20/6/24 by volume)].

Mass spectrometry: M=779 (theory=779).

$N^2$-[$O^1$-t-Butyl-N-(N-lauroyl-L-alanyl)-γ-D-glutamyl]-$N^6$-benzyloxycarbonyl-2(L),6(D,L)-diamino-4-thiapimelamic acid (6.3 g) is dissolved in a mixture, cooled to 0° C., of a 35% strength solution of hydrogen bromide in acetic acid (27.5 cc), diethyl phosphite (9 cc) and diethyl sulphide (14 cc). The reaction mixture is stirred for 1¼ hours and then poured into anhydrous ether (2 liters) cooled to 0° C. The mixture is stirred for 2 hours; the precipitate obtained is filtered off, washed 4 times with ether (1.2 liters in total) and dried under reduced pressure (0.3 mm Hg; 0.04 kPa). This yields a hygroscopic, light beige powder (7.5 g), which is chromatographed on neutral silica gel (0.04–0.063 mm) (300 g) contained in a column of diameter 4 cm. To do this, the powder (7.5 g) is dissolved in a mixture of methanol (100 cc) and ammonia (d=0.92) (4 cc), and neutral silica gel (0.04–0.063 mm) (16 g) is added to the solution thus obtained. The mixture is evaporated to dryness under reduced pressure (20 mm Hg; 2.7 kPa) at 50° C. and the residue thus obtained is charged onto the silica column. Elution is carried out with a metanol/ethyl acetate mixture (8/2 by volume) (1.53 liters), 30 cc fractions being collected. Fractions 35 to 51 are combined and concentrated to dryness under reduced pressure (20 mm Hg; 2.7 kPa) at 50° C. The residue obtained is triturated in ether (100 cc), filtered off and dried at 40° C. under reduced pressure (0.3 mm Hg; 0.04 kPa). This yields $N^2$-[N-(N-lauroyl-L-alanyl)-γ-D-glutamyl]-2(L),6(D,L)-diamino-4-thiapimelamic acid (4.05 g).

Rf=0.41 [silica gel; n-butanol/pyridine/acetic acid/water (50/20/6/24 by volume)].

Mass spectrometry: M=589 (theory=589).

Analysis: Calculated % C 52.95; H 8.03; N 11.88; S 5.44. Found % C 48.6; H 7.4; N 10.9; S 4.9.

t-Butyl N-(N-lauroyl-L-alanyl)-α-D-glutamate can be prepared in the following manner:

α-t-Butyl γ-benzyl N-(N-lauroyl-L-alanyl)-D-glutamate (55 g) is dissolved in t-butanol (4.7 liters). Palladium-on-charcoal (containing 3% of palladium) (55 g) is added and a slow stream of hydrogen is then passed in for 7 hours. After filtration, the reaction medium is concentrated to dryness under reduced pressure (20 mm Hg; 2.7 kPa, then 0.3 mm Hg; 0.04 kPa) at 50° C. This yields a thick oil (47.1 g), which is dissolved in a saturated solution of sodium bicarbonate (500 cc). This solution is extracted twice with ethyl acetate (500 cc in total) and the ethyl acetate phase is washed with a saturated solution of sodium bicarbonate (200 cc). The combined aqueous phases are acidified to pH 3-4 by adding citric acid and extracted 3 times with ethyl acetate (600 cc in total). The latter organic phase is dried over sodium sulphate and concentrated to dryness under reduced pressure (20 mm Hg; 2.7 kPa) at 50° C. This yields t-butyl N-(N-lauroyl-L-alanyl)-α-D-glutamate (36.5 g) in the form of an oil which crystallises at 20° C.

Rf: 0.67 [silica gel; ethyl acetate/acetic acid (9/1 by volume)].

Mass spectrometry: M=456 (theory=456).

α-t-Butyl γ-benzyl N-(N-lauroyl-L-alanyl)-D-glutamate can be prepared in the following manner:

Isobutyl chloroformate (23.2 cc) is added to a solution, kept at about −7° C., of N-lauroyl-L-alanine (48 g) in a mixture of tetrahydrofuran (300 cc) and triethylamine (24.9 cc). The mixture is stirred for 20 minutes at about −7° C. and a solution of α-t-butyl γ-benzyl D-glutamate (80 g) in tetrahydrofuran (330 cc) is then added. The reaction mixture is stirred for 30 minutes at a temperature of the order of 0° C. and then for 16 hours at a temperature of the order of 20° C.; it is then filtered. The filtrate is concentrated to dryness under reduced pressure (20 mm Hg; 2.7 kPa) at 45° C. The residual oil obtained is taken up in ethyl acetate (1.5 liters) and the solution is cooled to about 5° C. and washed successively with an iced saturated solution of citric acid (400 cc), 4 times with a saturated solution of sodium bicarbonate (1.2 liters in total) and with a saturated solution of sodium chloride (300 cc). After drying over sodium sulphate, the organic phase is concentrated to dryness under reduced pressure (20 mm Hg; 2.7 kPa) at 45° C. This yields a pale yellow oil (79 g) which is chromatographed on a column of diameter 8 cm, containing neutral silica (0.063–0.2 mm) (2.4 kg). Elution is carried out successively with a cyclohexane/ethyl acetate mixture (85/15 by volume) (3 liters), a cyclohexane/ethyl acetate mixture (80/20 by volume) (2.4 liters), a cyclohexane/ethyl acetate mixture (75/25 by volume) (15.6 liters), a cyclohexane/ethyl acetate mixture (70/30 by volume) (2.4 liters), a cyclohexane/ethyl acetate mixture (65/35 by volume) (2.4 liters), a cyclohexane/ethyl acetate mixture (60/40 by volume) (3 liters), a cyclohexane/ethyl acetate mixture (50/50 by volume) (4.2 liters) and a cyclohexane/ethyl acetate mixture (40/60 by volume) (4.2 liters), 600 cc fractions being collected. Fractions 34 to 60 are combined and concentrated to dryness under reduced pressure (20 mm Hg; 2.7 kPa) at 40° C. This yields α-t-butyl γ-benzyl N-(N-lauroyl-L-alanyl)-D-glutamate (55 g) in the form of a yellow oil.

Rf=0.55 [silica gel; cyclohexane/ethyl acetate (1/1 by volume)].

α-t-Butyl γ-benzyl D-glutamate can be prepared in the following manner:

Sulphuric acid (d=1.83) (49 cc) is added, in the course of 15 minutes, to a suspension, cooled to about 13° C., of γ-benzyl D-glutamate (64 g) in dioxane (500 cc). A stream of isobutene is passed into the solution obtained, kept at about 13° C., for 40 minutes; the reaction medium is then kept at 20° C. for 16 hours, a stream of isobutene is then passed into it again for 4 hours and the mixture is left to stand for 20 hours. The reaction mixture is then added, in the course of 10 minutes, to a mixture of N sodium hydroxide solution (2.6 liters) and ether (4.15 liters), cooled to about 0° C. The organic phase is separated off and the aqueous phase is extracted with ether (1 liter). The organic phases thus obtained are combined, dried over sodium sulphate and concentrated under reduced pressure (20 mm Hg; 2.7 kPa) at 32° C. This yields α-t-butyl γ-benzyl D-glutamate (80 g) containing about 20% of dioxane and 10% of benzyl alcohol. Concentration under a lower pressure or at a higher temperature reduces the yield. The product thus obtained must be used within a few days following isolation.

N-Lauroyl-L-alanine can be prepared in accordance with the method of E. JUNGERMANN et al., J. Amer. Chem. Soc. 78, 172 (1956).

γ-Benzyl D-glutamate can be prepared in accordance with the method of P. LEFRANCIER and E. BRICAS, Bull. Soc. Chim. France, 1965, 3,668.

$N^6$-benzyloxycarbonyl-2(L),6(D,L)-diamino-4-thiapimelamic acid can be prepared in the following manner:

A solution of potassium hydroxide pellets (24.3 g) in anhydrous ethanol (280 cc) is added to a solution of L-cysteine hydrochloride hydrate (25.35 g) in dimethylformamide (280 cc). N-Benzyloxycarbonyl-O-p-toluenesulphonyl-D,L-serinamide (56.65 g) dissolved in anhydrous ethanol (280 cc) is added to the slurry thus obtained. The reaction mixture is stirred for 5 hours at 20° C. and the insoluble material is then filtered off and washed twice with ethanol (60 cc in total). The combined filtrates are concentrated to dryness under reduced pressure (20 mm Hg; 2.7 kPa) at 60° C. The semicrystalline residue thus obtained is taken up in water (300 cc) warmed to 50° C., the insoluble material is filtered off and the filtrate is cooled to 0° C., acidified to pH 6-7 by adding anhydrous acetic acid (5.5 cc) and kept at 0° C. for 20 hours. The insoluble material is filtered off, washed successively twice with water (200 cc in total), twice with ethanol (120 cc in total) and with isopropyl ether (100 cc) and dried under reduced pressure (20 mm Hg; 2.7 kPa) at 50° C. This yields $N^6$-benzyloxycarbonyl-2(L),6(D,L)-diamino-4-thiapimelamic acid (27 g), which melts with decomposition at about 185° C.

Rf=0.50 [silica gel; n-butanol/pyridine/acetic acid/water (50/20/6/24 by volume)].

Mass spectrometry: M=341 (theory=341).

$[\alpha]_{436}^{20°} = +6°$ (N hydrochloric acid; c=1).

After hydrolysis in a concentrated hydrochloric acid/anhydrous acetic acid mixture (1/1 by volume) for 5 hours at 96° C., analysis on a BIOTRONIK autoanalyser shows the presence of the following aminoacids:

Lan 0.45 (theory=0.5)

meso-Lan 0.55 (theory=0.5)

N-Benzyloxycarbonyl-O-p-toluenesulphonyl-D,L-serinamide can be prepared in accordance with the method of L. BENOITON et al., J. Chem. Soc. page 824 (1964).

EXAMPLE 3

Isobutyl chloroformate (0.53 cc) is added to a solution, kept at −5° C., of N-t-butoxycarbonylglycine (720 mg) in a mixture of tetrahydrofuran (60 cc) and triethylamine (0.57 cc). The mixture is stirred for 20 minutes at −5° C. and a solution, cooled to 0° C., of $N^2$-[N-(N-lauroyl-L-alanyl)-γ-D-glutamyl]-2(L),6(D,L)-diamino-4-thiapimelamic acid (2.55 g) in water (50 cc) is then added. The reaction mixture is stirred for a few minutes at 0° C. and then for 18 hours at about 15° C. The tetrahydrofuran is evaporated off by concentration under reduced pressure (20 mm Hg; 2.7 kPa) at 45° C.; the concentrate is acidified to pH 2 by adding acetic acid (1 cc) and extracted 3 times with ethyl acetate (90 cc) in total. The combined organic phases are washed with water (10 cc), dried over sodium sulphate and concentrated to dryness under reduced pressure (20 mm Hg; 2.7 kPa) at 45° C. The residue obtained is triturated in ether (50 cc) and dried under reduced pressure (20 mm Hg; 2.7 kPa) at 20° C. This yields an orange powder (2.72 g) which is chromatographed on neutral silica gel (0.04-0.063 mm) (115 g) contained in a column of diameter 2.5 cm. To do this, the powder (2.72 g) is dissolved in acetic acid (40 cc), and neutral silica gel (0.04-0.063 mm) (12 g) is added to the solution obtained. The mixture is evaporated to dryness under reduced pressure (20 mm Hg; 2.7 kPa) at 55° C. and the residue thus obtained is charged onto the silica column. Elution is carried out successively with an ethyl acetate/acetic acid mixture (9/1 by volume) (1.68 liters) and an ethyl acetate/acetic acid mixture (8/2 by volume) (1.5 liters), 60 cc fractions being collected. Fractions 14 to 53 are combined and concentrated to dryness under reduced pressure (20 mm Hg; 2.7 kPa) at 50° C. The residue obtained is triturated in ether (50 cc), filtered off and dried under reduced pressure (20 mm Hg; 2.7 kPa) at 20° C. This yields $N^2$-[N-(N-lauroyl-L-alanyl)-$\gamma$-D-glutamyl]-$N^6$-t-butoxycarbonylglycyl-2(L),6(D,L)-diamino-4-thiapimelamic acid (1.8 g).

Rf=0.43 [silica gel; n-butanol/pyridine/acetic acid/water (50/20/6/24 by volume)].

$N^2$-[N-(N-Lauroyl-L-alanyl)-$\gamma$-D-glutamyl]-$N^6$-t-butoxycarbonylglycyl-2(L),6(D,L)-diamino-4-thiapimelamic acid (1.8 g) is dissolved in a 1.7 N anhydrous solution of hydrogen chloride in acetic acid (36 cc). The reaction mixture is stirred for 2 hours and a very small amount of insoluble material is then removed by filtration; ether (15 cc) is added to the filtrate and the mixture is stirred for ¼ hour. The precipitate which has appeared is filtered off, washed 3 times with ether (60 cc in total) and dried under reduced pressure (20 mm Hg; 2.7 kPa) at 20° C. This yields a powder (1.44 g) which is dissolved in water (25 cc). Triethylamine (0.5 cc) and acetic acid (0.5 cc) are added successively. After standing for ¼ hour in a bath at 0° C., the precipitate which has formed is filtered off, washed twice with water (10 cc in total) and dried under reduced pressure (20 mm Hg; 2.7 kPa) at 20° C. This yields a powder (1.18 g) which is chromatographed on neutral silica gel (0.04-0.063 mm) (42 g) contained in a column of diameter 2.5 cm. To do this, the powder (1.18 g) is dissolved in methanol (50 cc) containing concentrated ammonia solution (0.25 cc), and neutral silica gel (0.04-0.063 mm) (5 g) is added to the solution obtained. The mixture is evaporated to dryness under reduced pressure (20 mm Hg; 2.7 kPa) at 50° C. and the residue thus obtained is charged onto the silica column. Elution is carried out with methanol, 30 cc fractions being collected. Fractions 14 to 26 are combined and concentrated to dryness under reduced pressure (20 mm Hg; 2.7 kPa) at 50° C. This yields $N^2$-[N-(N-lauroyl-L-alanyl)-$\gamma$-D-glutamyl]-$N^6$-glycyl-2(L),6(D,L)-diamino-4-thiapimelamic acid (630 mg).

Rf=0.30 [silica gel; n-butanol/pyridine/acetic acid/water (50/20/6/24 by volume)].

Analysis: Calculated % C 52.00; H 7.79; N 12.99; S 4.96. Found % C 49.1; H 7.7; N 12.0; S 4.6.

After hydrolysis in a concentrated hydrochloric acid/anhydrous acetic acid mixture (1/1 by volume) for 5 hours at 96° C., analysis on a BIOTRONIK autoanalyser shows the presence of the following aminoacids:
Glu=0.92 (theory=1)
Gly=1.03 (theory=1)
Lan=0.55 (theory=0.5)
meso-Lan=0.45 (theory=0.5)

EXAMPLE 4

Isobutyl chloroformate (0.3 cc) is added to a solution, kept at −5° C., of t-butyl N-(N-lauroyl-L-alanyl)-$\alpha$-D-glutamate (1.05 g) in a mixture of tetrahydrofuran (45 cc) and triethylamine (0.32 cc). The mixture is stirred for 20 minutes at −5° C. and a solution, cooled to 0° C., of $N^6$-benzyloxycarbonyl-2(D/L mixture),6(L)-diamino-4-thiapimelamoyl-glycine hydrochloride (1 g) in a mixture of 1 N sodium hydroxide solution (4.6 cc), water (23 cc) and tetrahydrofuran (17 cc) is then added. The reaction mixture is stirred for a few minutes at 0° C. and then for 20 hours at about 20° C. and then acidified to pH 3 by adding 1 N hydrochloric acid (2.5 cc). The tetrahydrofuran is evaporated off by concentration under reduced pressure (20 mm Hg) at 50° C. The concentrate is diluted by adding water (25 cc); the precipitate which has appeared is filtered off, washed 3 times with distilled water (15 cc in total) and dried under reduced pressure (20 mm Hg; 2.7 kPa) at 20° C. This yields a powder (1.82 g) which is chromatographed on silica gel (0.04-0.063 mm) (91 g) contained in a column of diameter 2.5 cm. Elution is carried out successively with an ethyl acetate/acetic acid mixture (95/5 by volume) (200 cc), an ethyl acetate/acetic acid mixture (9/1 by volume) (240 cc), an ethyl acetate/acetic acid mixture (8/2 by volume) (240 cc) and an ethyl acetate/acetic acid mixture (1/1 by volume) (200 cc), 40 cc fractions being collected. Fractions 16 to 21 are combined and concentrated to dryness under reduced pressure (20 mm Hg) at 20° C. This yields $N^2$-[$O^1$-t-butyl-N-(N-lauroyl-L-alanyl)-$\gamma$-D-glutamyl]-$N^6$-benzyloxycarbonyl-2(D/L mixture),6(L)-diamino-4-thiapimelamoyl-glycine (510 mg).

Rf=0.76 [silica gel; n-butanol/pyridine/acetic acid/water (50/20/6/24 by volume)].

$N^2$-[$O^1$-t-Butyl-N-(N-lauroyl-L-alanyl)-$\gamma$-D-glutamyl]-$N^6$-benzyloxycarbonyl-2(D/L mixture),6(L)-diamino-4-thiapimelamoyl-glycine (470 mg) is dissolved in a 33% strength solution of hydrogen bromide in acetic acid (5 cc). The reaction mixture is stirred for 40 minutes at 20° C., purged for 10 minutes by bubbling nitrogen through it and concentrated to dryness under reduced pressure (20 mm Hg; 2.7 kPa, then 0.3 mm Hg; 0.04 kPa) at 50° C. The residue obtained is triturated in ether (20 cc), filtered off, washed with ether (5 cc) and dried under reduced pressure (20 mm Hg; 2.7 kPa) at 20° C. This yields an orange powder (530 mg) which is dissolved in water (20 cc). Triethylamine (0.2 cc) and then acetic acid (0.2 cc) are added to this solution. The reaction mixture is cooled at 0° C. for 15 minutes. The precipitate formed in this way is filtered off, washed 5 times with water (10 cc in total) and dried under reduced pressure (0.3 mm Hg; 0.04 kPa) at 20° C. This yields a powder (360 mg) which is chromatographed on silica gel (0.04-0.063 mm) (36 g) contained in a column of diameter 2.5 cm. Elution is carried out with methanol, 5 cc fractions being collected. Fractions 5 to 16 are combined and concentrated to dryness under reduced pressure (0.3 mm Hg; 0.04 kPa) at 50° C. This yields N²-[N-(N-lauroyl-L-alanyl)-γ-D-glutamyl]-2(D/L mixture),6(L)-diamino-4-thiapimelamoyl-glycine (160 mg).

Rf=0.26 [silica gel; n-butanol/pyridine/acetic acic/water (50/20/6/24 by volume)].

Analysis: Calculated % C 52.00; H 7.79; N 12.99; S 4.96. Found % C 47.1; H 7.3; N 11.4; S 4.6.

After hydrolysis in a concentrated hydrochloric acid/anhydrous acetic acid mixture (1/1 by volume) for 5 hours at 96° C., analysis on a BIOTRONIK autoanalyser shows the presence of the following aminoacids:

| Glu | = 1.00 | (theory = 1) |
| Gly | = 1.02 | (theory = 1) |
| Lan | = 0.60 | } (theory = 1) |
| meso-Lan | = 0.37 | |

An additional fraction (90 mg) of N²-[N-(N-lauroyl-L-alanyl)-γ-D-glutamyl]-2(D/L mixture),6(L)-diamino-4-thiapimelamoyl-glycine can be obtained in the following manner: fractions 3 and 4 are combined and concentrated to dryness under reduced pressure (20 mm Hg; 2.7 kPa) at 50° C. and the residue is chromatographed on silica gel (0.04–0.063 mm) (22 g) contained in a column of diameter 2.5 cm. Elution is carried out with methanol, 5 cc fractions being collected. Fractions 7 to 18 are combined and concentrated to dryness under reduced pressure (20 mm Hg; 2.7 kPa) at 50° C. and the residue is dried under reduced pressure (0.3 mm Hg; 0.04 kPa) at 50° C.

N⁶-Benzyloxycarbonyl-2(D/L mixture),6(L)-diamino-4-thiapimelamoyl-glycine can be prepared in the following manner:

t-Butyl N²-t-butoxycarbonyl-N⁶-benzyloxycarbonyl-2(D/L mixture),6(L)-diamino-4-thiapimelamoyl-glycinate (2 g) is dissolved in a 1.65 N anhydrous solution of hydrogen chloride in acetic acid (20 cc). The solution is stirred for 2 hours at 20° C. Ether (50 cc) is then added to the reaction mixture. This gives a white precipitate which is filtered off, washed twice with ether (20 cc in total) and dried under reduced pressure (0.3 mm Hg; 0.04 kPa) at 20° C. This yields N⁶-benzyloxycarbonyl-2(D/L mixture),6(L)-diamino-4-thiapimelamoyl-glycine hydrochloride (1.13 g).

Rf=0.38 [silica gel; n-butanol/pyridine/acetic acid/water (50/20/6/24 by volume)].

After hydrolysis in a concentrated hydrochloric acid/anhydrous acetic acid mixture (1/1 by volume) for 5 hours at 96° C., analysis on a BIOTRONIK autoanalyser shows the presence of the following aminoacids:

| Lan | = 0.59 | } (theory = 1) |
| meso-Lan | = 0.34 | |
| Gly | = 1.00 | (theory = 1) | t-Butyl N²-t-butoxycarbonyl-N⁶-benzyloxycarbonyl-2(D/L mixture),6(L)-diamino-4-thiapimelamoyl-glycinate can be prepared in the following manner:

A solution of potassium hydroxide pellets (253 mg) in anhydrous ethanol (9 cc) is added to a solution of N-benzyloxycarbonyl-L-cysteinamide (1.14 g) in dimethylformamide (9 cc). The solution thus obtained is added to a suspension of t-butyl N-t-butoxycarbonyl-O-p-toluenesulphonyl-L-seryl-glycinate (1.98 g) in ethanol (9 cc). The reaction mixture is stirred for 4 hours at 20° C. This gives a pale yellow solution which is concentrated to dryness under reduced pressure (20 mm Hg; 2.7 kPa) at 60° C. The residue obtained is triturated in water (50 cc), kept at 5° C. for 48 hours, filtered off, washed with water (10 cc) and dried under reduced pressure (0.3 mm Hg; 0.04 kPa) at 20° C. This yields t-butyl N²-t-butoxycarbonyl-N⁶-benzyloxycarbonyl-2(D/L mixture,6(L)-diamino-4-thiapimelamoyl-glycinate (2.1 g) in the form of a white powder.

Rf=0.72 [silica gel; ethyl acetate].

Mass spectrometry: M=554 (theory=554).

After hydrolysis in a concentrated hydrochloric acid/anhydrous acetic acid mixture (1/1 by volume) for 5 hours at 96° C., analysis on a BIOTRONIK autoanalyser shows the presence of the following aminoacids:

| Lan | = 0.59 | } (theory = 1) |
| meso-Lan | = 0.34 | |
| Gly | = 1.00 | (theory = 1) | t-Butyl N-t-butoxycarbonyl-O-p-toluenesulphonyl-L-seryl-glycinate can be prepared in the following manner:

p-Toluenesulphonyl chloride (3.09 g) is added in small portions, in the course of 3 minutes, to a solution, cooled to −6° C., of t-butyl N-t-butoxycarbonyl-L-seryl-glycinate (2.58 g) in pyridine (9 cc). The reaction mixture is kept for 2 hours at −6° C. and then poured onto crushed ice (60 g) and the mixture is kept for 20 hours at 4° C. The precipitate thus obtained is filtered off, washed 5 times with water (100 cc in total), dried under reduced pressure (20 mm Hg) at 20° C. and re-crystallised from ethanol (100 cc). This yields t-butyl N-t-butoxycarbonyl-O-p-toluenesulphonyl-L-seryl-glycinate (2.54 g) which melts at 180°–182° C.

Rf=0.91 [silica gel; ethyl acetate].

t-Butyl N-t-butoxycarbonyl-L-seryl-glycinate can be prepared in the following manner:

Dicyclohexylcarbodiimide (6.81 g) is added to a solution, cooled to 5° C., of N-t-butoxycarbonyl-L-serine (6.16 g) and t-butyl glycinate (3.93 g) in methylene chloride (100 cc). The reaction mixture is stirred for 30 minutes at 5° C. and then for 18 hours at about 20° C. The precipitate of dicyclohexylurea formed is filtered off and washed twice with methylene chloride (40 cc in total). The combined organic phases are washed successively 3 times with a saturated solution of sodium bicarbonate (90 cc in total) and twice with water (60 cc in total), dried over sodium sulphate and concentrated to dryness under reduced pressure (20 mm Hg; 2.7 kPa) at 20° C. This yields an oil (10.22 g) which is chromatographed on neutral silica gel (0.04–0.063 mm) (100 g) contained in a column of diameter 3.4 cm. Elution is carried out successively with a cyclohexane/ethyl acetate mixture (1/1 by volume) (500 cc) and a cyclohexane/ethyl acetate mixture (⅓ by volume) (600 cc), 100 cc fractions being collected. Fractions 5 to 8 are combined and concentrated to dryness under reduced pressure (20 mm Hg; 2.7 kPa) at 50° C. This yields t-butyl N-t-butoxycarbonyl-L-seryl-glycinate (2.64 g) in the form of an oil which crystallises slowly.

Rf=0.68 [silica gel; ethyl acetate].

EXAMPLE 5

Isobutyl chloroformate (1.3 cc) is added to a solution, kept at −10° C., of t-butyl N-(N-lauroyl-N-alanyl)-α-

D-glutamate (4.56 g) in a mixture of tetrahydrofuran (230 cc) and triethylamine (1.4 cc). The mixture is stirred for 25 minutes at −10° C. and a solution, cooled to 0° C., of $N^2$-benzyloxycarbonyl-2(L),6(D,L)-diamino-4-thiapimelamic acid hydrochloride (3.78 g) in 0.1 N sodium hydroxide solution (100 cc) is then added.

The reaction mixture is stirred for 5 minutes at 0° C. and then for 18 hours at about 20° C. The tetrahydrofuran is evaporated off by concentration under reduced pressure (20 mm Hg; 2.7 kPa) at 50° C.; the concentrate is acidified to pH 2 by adding 1 N hydrochloric acid (about 15 cc). The oil formed in the reaction mixture is separated off by decantation and triturated in ether (200 cc). This yields an amorphous solid which is filtered off and washed 3 times with ether (600 cc in total). The product obtained is stirred very vigorously in boiling ethyl acetate (100 cc), and then, after cooling to 20° C., ether (100 cc) is added, the suspension is cooled at 0° C. for ¼ hour and the insoluble material is filtered off. After washing with ether (100 cc) and drying under reduced pressure (20 mm Hg; 2.7 kPa) at 20° C., $N^2$-benzyloxycarbonyl-$N^6$-[$O^1$-t-butyl-(N-lauroyl-L-alanyl)-γ-D-glutamyl]-2(L),6(D,L)-diamino-4-thiapimelamic acid (5.15 g) is obtained.

Rf=0.69 [silica gel; ethyl acetate/acetic acid (3/1 by volume)].

Mass spectrometry: M=779 (theory=779).

$N^2$-Benzyloxycarbonyl-$N^6$-[$O^1$-t-butyl-(N-lauroyl-L-alanyl)-γ-D-glutamyl]-2(L),6(D,L)-diamino-4-thiapimelamic acid (5 g) is dissolved in a 28% strength solution of hydrogen bromide in acetic acid (30 cc). The reaction mixture is stirred for 3 hours and filtered in order to remove a small amount of insoluble material, and the filtrate is concentrated to dryness under reduced pressure (20 mm Hg; 2.7 kPa, then 0.3 mm Hg; 0.04 kPa) at 50° C. The residue thus obtained is triturated in ether (400 cc), filtered off and taken up in water (1.5 liters), whilst stirring vigorously; it solubilises instantaneously in water and then precipitates after a few minutes. It is filtered off, washed successively with water (50 cc), ether (50 cc), ethyl acetate (50 cc) and ether (50 cc) and dried under reduced pressure (0.3 mm Hg; 0.04 kPa) at 50° C. This yields $N^6$-[N-(N-lauroyl-L-alanyl)-γ-D-glutamyl]-2(L),6(D,L)-diamino-4-thiapimelamic acid (3.2 g), which melts with decomposition at about 176° C.

Rf=0.32 [silica gel; n-butanol/pyridine/acetic acid/water (50/20/6/24 by volume)].

Analysis: Calculated % C 52.95; H 8.03; N 11.87; S 5.44. Found C 49.7; H 7.7; N 11.0; S 5.1.

Sulphuric ash: 3.9%.

After hydrolysis in a concentrated hydrochloric acid/anhydrous acetic acid mixture (1/1 by volume) for 5 hours at 96° C., analysis on a BIOTRONIK autoanalyser shows the presence of the following aminoacids:
Lan=0.55 (theory=0.5)
meso-Lan=0.50 (theory=0.5)
Glu=1.00 (theory=1)

$N^2$-Benzyloxycarbonyl-2(L),6(D,L)-diamino-4-thiapimelamic acid hydrochloride can be prepared in the following manner:

A 1.65 N anhydrous solution of hydrogen chloride in acetic acid (500 cc) is added to a solution of $N^2$-benzyloxycarbonyl-$N^6$-t-butoxycarbonyl-2(L),6(D,L)-diamino-4-thiapimelamic acid (37 g) in anhydrous acetic acid (100 cc). The mixture is stirred for 2 hours at a temperature of the order of 20° C. The reaction mixture is then concentrated to dryness under reduced pressure (20 mm Hg; 2.7 kPa, then 0.3 mm Hg; 0.04 kPa) at 50° C. The residue obtained is triturated 4 times in ether (2 liters in total), filtered off, washed 3 times with ether (600 cc in total) and dried under reduced pressure (0.3 mm Hg; 0.04 kPa) at 20° C. This yields $N^2$-benzyloxycarbonyl-2(L),6(D,L)-diamino-4-thiapimelamic acid hydrochloride (19.1 g).

Rf=0.48 [silica gel; n-butanol/pyridine/acetic acid/water (50/20/6/24 by volume)].

$[\alpha]_D^{21°}=-22.8°$ (1 N hydrochloric acid; c=1).

After hydrolysis in a concentrated hydrochloric acid/anhydrous acetic acid mixture (1/1 by volume) for 5 hours at 96° C., analysis on a BIOTRONIK autoanalyser shows the presence of the following aminoacids:
Lan=0.5 (theory=0.5)
meso-Lan=0.5 (theory=0.5)

$N^2$-Benzyloxycarbonyl-$N^6$-t-butoxycarbonyl-2(L),6(D,L)-diamino-4-thiapimelamic acid can be prepared in the following manner:

A solution of potassium hydroxide pellets (16.8 g) in anhydrous ethanol (190 cc) is added to a solution of N-benzyloxycarbonyl-L-cysteine (25.5 g) in dimethylformamide (190 cc). N-t-Butoxycarbonyl-O-p-toluenesulphonyl-D,L-serinamide (35.8 g) dissolved in dimethylformamide (190 cc) is added to the solution thus obtained. The reaction mixture is stirred for 18 hours at 20° C.; it is then concentrated to dryness under reduced pressure (20 mm Hg; 2.7 kPa, then 0.3 mm Hg; 0.04 kPa) at 60° C. The residue thus obtained is taken up in water (250 cc) and the solution is extracted 3 times with ethyl acetate (600 cc in total) and acidified to pH 3 with citric acid (about 40 g). The aqueous phase thus obtained is extracted 3 times with ethyl acetate (600 cc in total). The combined organic phases are washed with a saturated solution of sodium chloride (100 cc), dried over sodium sulphate and concentrated to dryness under reduced pressure (20 mm Hg; 2.7 kPa) at 50° C. This yields $N^2$-benzyloxycarbonyl-$N^6$-t-butoxycarbonyl-2(L),6(D,L)-diamino-4-thiapimelamic acid (37 g) in the form of an orange oil.

Rf=0.49 [silica gel; ethyl acetate/acetic acid (9/1 by volume)].

Rf=0.52 [silica gel; n-butanol/pyridine/acetic acid/water (50/20/6/24 by volume)].

N-Benzyloxycarbonyl-L-cysteine can be prepared in accordance with the method of W. FOYE et al., J. Am. Pharm. Ass. 46, 273 (1957).

N-t-Butoxycarbonyl-O-p-toluenesulphonyl-D,L-serinamide can be prepared in the following manner:

p-Toluenesulphonyl chloride (67.5 g) is added in small portions, in the course of 20 minutes, to a solution, cooled to between −20° C. and −10° C., of N-t-butoxycarbonyl-D,L-serinamide (67 g) in pyridine (280 cc). The reaction mixture is kept for 1½ hours at a temperature between −10° C. and −5° C. and then left to stand at 20° C. for 2½ hours. It is then poured onto a water/ice mixture (550 g). The white precipitate thus obtained is filtered off, washed 4 times with water (1.2 liters in total), dried in air, washed twice with ether (400 cc in total) and dried under reduced pressure (20 mm Hg; 2.7 kPa) at 50° C. This yields N-t-butoxycarbonyl-O-p-toluenesulphonyl-D,L-serinamide (73.3 g), which melts at 161° C.

Rf=0.82 [silica gel; ethyl acetate/acetic acid (9/1 by volume)].

N-t-Butoxycarbonyl-D,L-serinamide can be prepared in the following manner:

A stream of ammonia is passed for 7 hours into a solution of methyl N-t-butoxycarbonyl-D,L-serinate (217 g) in methanol (2.17 liters), cooled to 0° C.; the reaction mixture is then left to stand for 15 hours at 20° C., and then, after it has been cooled to about 0° C., a stream of ammonia is passed in again for 6 hours and the mixture is left to stand at 20° C. for 18 hours. The reaction mixture is concentrated under reduced pressure (20 mm Hg; 2.7 kPa) at 50° C. The residue thus obtained is taken up in ether (1.5 liters). The crystals obtained are filtered off, washed 3 times with ether (1.5 liters in total) and dried in air. This yields N-t-butoxycarbonyl-D,L-serinamide (158 g), which melts at 115°–116° C.

Methyl N-t-butoxycarbonyl-D,L-serinate can be prepared in accordance with the method of N. BOGGS et al., J. Org. Chem., 44, 2,262 (1979).

EXAMPLE 6

Isobutyl chloroformate (0.28 cc) is added to a solution, kept at −10° C., of N-t-butoxycarbonylglycine (382 mg) in a mixture of tetrahydrofuran (32 cc) and triethylamine (0.3 cc). The mixture is stirred for 20 minutes at −10° C. and a solution, cooled to 0° C., of $N^6$-[N-(N-lauroyl-L-alanyl)-$\gamma$-D-glutamyl]-2(L),6(D,L)-diamino-4-thiapimelamic acid (1.28 g) in a mixture of 1 N sodium hydroxide solution (4.34 cc) and water (32 cc) is then added. The reaction mixture is stirred for 5 minutes at 0° C. and then for 70 hours at about 20° C. The tetrahydrofuran is evaporated off by concentration under reduced pressure (20 mm Hg; 2.7 kPa) at 50° C. and the concentrate is acidified to pH 2 by adding 1 N hydrochloric acid (about 5 cc) and extracted 3 times with ethyl acetate (90 cc in total). The combined organic phases are dried over sodium sulphate and concentrated to dryness under reduced pressure (20 mm Hg; 2.7 kPa) at 50° C. This yields a white powder (1.7 g) which is chromatographed on neutral silica gel (0.04–0.063 mm) (50 g) contained in a column of diameter 2.4 cm. Elution is carried out successively with ethyl acetate (120 cc), an ethyl acetate/acetic acid mixture (95/5 by volume) (560 cc), an ethyl acetate/acetic acid mixture (90/10 by volume) (1.12 liters) and an ethyl acetate/acetic acid mixture (80/20 by volume) (480 cc), 40 cc fractions being collected. Fractions 25 to 57 are combined and concentrated to dryness under reduced pressure (20 mm Hg; 2.7 kPa) at 50° C. The residue obtained is triturated 3 times in ether (90 cc in total) and dried under reduced pressure (20 mm Hg; 2.7 kPa) at 50° C. This yields $N^2$-(t-butoxycarbonylglycyl)-$N^6$-[N-(N-lauroyl-L-alanyl)-$\gamma$-D-glutamyl]-2(L),6(D,L)-diamino-4-thiapimelamic acid (490 mg).

Rf=0.48 [silica gel; n-butanol/pyridine/acetic acid/water (50/20/6/24 by volume)].

Rf=0.24 [silica gel; ethyl acetate/acetic acid (3/1 by volume)].

$N^2$-(t-Butoxycarbonylglycyl)-$N^6$-[N-(N-lauroyl-L-alanyl)-$\gamma$-D-glutamyl]-2(L),6(D,L)-diamino-4-thiapimelamic acid (490 mg) is dissolved in a 1.65 N anhydrous solution of hydrogen chloride in acetic acid (10 cc). The solution is stirred for 2¼ hours at a temperature of the order of 20° C. The reaction mixture is then filtered in order to remove a small amount of insoluble material, and the filtrate is concentrated to dryness under reduced pressure (20 mm Hg; 2.7 kPa) at 50° C. The residue thus obtained is triturated in ethyl acetate (50 cc), filtered off and washed 3 times with ether (150 cc in total). This yields a white powder (0.42 g) which is chromatographed on neutral silica gel (0.04–0.063 mm) (24 g) contained in a column of diameter 1.6 cm. Elution is carried out with acetic acid, 10 cc fractions being collected. Fractions 24 to 45 are combined and concentrated to dryness under reduced pressure (20 mm Hg; 2.7 kPa) at 45° C. The residue obtained is triturated in ethyl acetate (50 cc), filtered off, washed 3 times with ether (90 cc in total) and dried under reduced pressure (0.3 mm Hg; 0.04 kPa) at 50° C. This yields $N^2$-glycyl-$N^6$-[N-(N-lauroyl-L-alanyl)-$\gamma$-D-glutamyl]-2(L),6(D,L)-diamino-4-thiapimelamic acid hydrochloride (200 mg).

Rf=0.29 [silica gel; n-butanol/pyridine/acetic acid/water (50/20/6/24 by volume)].

Analysis: Calculated % C 49.22; H 7.62; Cl 5.19; N 12.30; S 4.69. Found % C 45.6; H 7.5; Cl 4.6; N 11.5; S 4.6.

Mass spectrometry: M=646 (theory for the base=646).

After hydrolysis in a concentrated hydrochloric acid/anhydrous acetic acid mixture (1/1 by volume) for 5 hours at 96° C., analysis on a BIOTRONIK autoanalyser shows the presence of the following aminoacids:

Lan=0.59 (theory=0.5)
meso-Lan=0.43 (theory=0.5)
Glu=0.97 (theory=1)
Gly=1.00 (theory=1)

EXAMPLE 7

Isobutyl chloroformate (0.65 cc) is added to a solution, kept at −10° C., of t-butyl N-(N-lauroyl-L-alanyl)-$\alpha$-D-glutamate (2.28 g) in a mixture of tetrahydrofuran (125 cc) and triethylamine (0.7 cc). The mixture is stirred for 40 minutes at −10° C. and a solution, cooled to 0° C., of $N^2$-benzyloxycarbonyl-L-lanthioninediamide hydrochloride (1.9 g) in a mixture of 1 N sodium hydroxide solution (5 cc) and water (50 cc) is then added. The reaction mixture is stirred for 20 minutes at about 0° C. and then for 70 hours at about 20° C. The precipitate which has appeared in the reaction mixture is filtered off, washed successively with water (25 cc), ethanol (25 cc) and isopropyl ether (50 cc) and dried under reduced pressure (20 mm Hg; 2.7 kPa) at 20° C. This yields $N^2$-[$O^1$-t-butyl-N-(N-lauroyl-L-alanyl)-$\gamma$-D-glutamyl]-$N^6$-benzyloxycarbonyl-L-lanthioninediamide (2.9 g).

Rf=0.41 [silica gel; ethyl acetate/acetic acid (9/1 by volume)].

$N^2$-[$O^1$-t-butyl-N-(N-lauroyl-L-alanyl)-$\gamma$-D-glutamyl]-$N^6$-benzyloxycarbonyl-L-lanthioninediamide (4.4 g) is dissolved in a 35% strength solution of hydrogen bromide in acetic acid (44 cc). The reaction mixture is stirred for 4 hours at 20° C. and then purged for ½ hour with nitrogen and concentrated to dryness under reduced pressure (20 mm Hg; 2.7 kPa) at 50° C. The residue thus obtained is triturated in isopropyl ether (50 cc) and filtered off. This operation is repeated twice and the solid is then stirred in acetone (50 cc) for one hour, filtered off, washed twice with acetone (10 cc in total) and dried under reduced pressure (20 mm Hg; 2.7 kPa) at 20° C. This yields $N^2$-[N-(N-lauroyl-L-alanyl)-$\gamma$-D-glutamyl]-L-lanthioninediamide hydrobromide (3.24 g) in the form of a cream-coloured powder.

Rf=0.47 [silica gel; n-butanol/pyridine/acetic acid/water (50/20/6/24 by volume)].

Analysis: Calculated % C 46.63; H 7.38; Br 11.93; N 12.55; S 4.79. Found % C 42.0; H 7.0; Br 10.1; N 11.1; S 4.4.

After hydrolysis in a concentrated hydrochloric acid/anhydrous acetic acid mixture (1/1 by volume) for 5 hours at 96° C., analysis on a BIOTRONIK autoanalyser shows the presence of the following aminoacids:

Glu=0.87 (theory=1)
Lan=0.88 (theory=1)
meso-Lan=0.12 (theory=0)

$N^2$-benzyloxycarbonyl-L-lanthioninediamide hydrochloride can be prepared in the following manner:

$N^2$-Benzyloxycarbonyl-$N^6$-t-butoxycarbonyl-L-lanthioninediamide (9.56 g) is dissolved in a 1.7 N anhydrous solution of hydrogen chloride in acetic acid (190 cc). The reaction mixture is stirred for 1 hour at 20° C., purged for ½ hour with a stream of nitrogen and poured into isopropyl ether (950 cc). After stirring for 1½ hours, the white precipitate which has appeared is filtered off, washed twice with isopropyl ether (200 cc in total) and dried under reduced pressure (20 mm Hg; 2.7 kPa) at 20° C. This yields $N^2$-benzyloxycarbonyl-L-lanthioninediamide hydrochloride (7.95 g).

$N^2$-Benzyloxycarbonyl-$N^6$-butoxycarbonyl-L-lanthioninediamide can be prepared in the following manner:

Isobutyl chloroformate (14.4 cc) is added to a solution, kept at −10° C., of $N^2$-benzyloxycarbonyl-$N^6$-t-butoxycarbonyl-L-lanthionine (27.7 g) in tetrahydrofuran (480 cc) and triethylamine (13.5 cc). The solution is stirred for 20 minutes at −10° C. and a stream of ammonia is then passed into the reaction mixture for about 3 hours at about −10° C. The reaction mixture is concentrated to dryness under reduced pressure (20 mm Hg; 2.7 kPa) at 45° C. The pasty residue is taken up in a mixture of a 7% strength aqueous solution of potassium carbonate (500 cc) and ethyl acetate (250 cc). The insoluble material is filtered off, the organic phase is separated off by decantation and the aqueous phase is extracted with ethyl acetate (50 cc). The combined organic phases are washed 3 times with water (150 cc in total), dried over sodium sulphate and concentrated to dryness under reduced pressure (20 mm Hg; 2.7 kPa) at 45° C. The residue obtained is stirred for ½ hour in isopropyl ether (50 cc), filtered off, washed twice with isopropyl ether (50 cc in total) and dried under reduced pressure (20 mm Hg; 2.7 kPa) at 20° C. This yields $N^2$-benzyloxycarbonyl-$N^6$-t-butoxycarbonyl-L-lanthioninediamide (9.1 g), which melts at 120° C.

Rf=0.61 [silica gel; ethyl acetate/acetic acid (9/1 by volume)].

$N^2$-Benzyloxycarbonyl-$N^6$-t-butoxycarbonyl-L-lanthionine can be prepared in the following manner:

A solution of di-t-butyl carbonate (11.6 g) in dioxane (100 cc) is added to a suspension of $N^2$-benzyloxycarbonyl-L-lanthionine (16.5 g) and sodium carbonate (10.2 g) in a mixture of water (100 cc) and dioxane (300 cc). The reaction mixture is stirred for 69 hours at a temperature of the order of 20° C. The insoluble material is filtered off and the dioxane in the filtrate is removed by concentration under reduced pressure (20 mm Hg; 2.7 kPa) at 45° C. A saturated solution of citric acid (150 cc) and ethyl acetate (150 cc) are added to the residual aqueous solution. The organic phase is separated off by decantation and the aqueous phase is then extracted twice with ethyl acetate (150 cc in total). The organic phases are combined, washed with water (100 cc), dried over sodium sulphate and concentrated to dryness under reduced pressure (20 mm Hg; 2.7 kPa) at 45° C. This yields $N^2$-benzyloxycarbonyl-$N^6$-t-butoxycarbonyl-L-lanthionine (27.7 g) in the form of a yellow oil.

EXAMPLE 8

Isobutyl chloroformate (0.4 cc) is added to a solution, kept at −8° C., of t-butyl N-(N-lauroyl-L-alanyl)-α-D-glutamate (1.41 g) in a mixture of tetrahydrofuran (67 cc) and triethylamine (0.43 cc). The mixture is stirred for 25 minutes at −7° C. and a solution, cooled to 0° C., of $N^7$-benzyloxycarbonyl-L,L-2,7-diamino-4-thiasuberamic acid (1.1 g) in a mixture of 1 N sodium hydroxide solution (3.1 cc) and water (27 cc) is then added. The reaction mixture is stirred for 10 minutes at −7° C. and then for 20 hours at about 20° C. It is then concentrated to dryness under reduced pressure (20 mm Hg; 2.7 kPa) at 45° C. The residue obtained is dissolved in water (30 cc) and the solution is acidified to pH 2 by adding 1 N hydrochloric acid (3.8 cc). The precipitate formed is filtered off, washed twice with water (100 cc in total) and dried under reduced pressure (20 mm Hg; 2.7 kPa, then 0.3 mm Hg; 0.04 kPa) at 20° C. This yields a powder (2.9 g) which is chromatographed on neutral silica gel (0.04–0.063mm) (90 g) contained in a column of diameter 2.5 cm. To do this, the powder (2.9 g) is dissolved in a mixture of acetic acid (30 cc) and ethyl acetate (15 cc), and neutral silica gel (0.04–0.063 mm) (9 g) is added to the solution obtained. The mixture is evaporated to dryness under reduced pressure (20 mm Hg; 2.7 kPa) at 50° C. and the residue thus obtained is charged onto the silica column. Elution is carried out with an ethyl acetate/acetic acid mixture (95/5 by volume) (2.9 liters), 50 cc fractions being collected. Fractions 17 to 55 are combined and concentrated to dryness under reduced pressure (20 mm Hg; 2.7 kPa) at 50° C. The residue obtained is triturated in ether (100 cc), filtered off, washed twice with ether (10 cc in total) and dried under reduced pressure (20 mm Hg; 2.7 kPa) at 20° C. This yields $N^2$-[$O^1$-t-butyl-N-(N-lauroyl-L-alanyl)-γ-D-glutam-yl]-$N^7$-benzyloxycarbonyl-L,L-2,7-diamino-4-thiasuberamic acid (1.2 g).

Rf=0.59 [silica gel; ethyl acetate/acetic acid (4/1 by volume)].

$N^2$-[$O^1$-t-Butyl-N-(N-lauroyl-L-alanyl)-γ-D-glutamyl]-$N^7$-benzyloxycarbonyl-L,L-2,7-diamino-4-thiasuberamic acid (1.2 g) is dissolved in a 33% strength solution of hydrogen bromide in acetic acid (12 cc). The reaction mixture is stirred for 2 hours at 20° C. and concentrated to dryness under reduced pressure (20 mm Hg; 2.7 kPa) at 50° C., the residue is taken up in ethyl acetate (20 cc), the solution is concentrated to dryness again under reduced pressure (20 mm Hg; 2.7 kPa) at 50° C. and the residue is triturated in a mixture of ether (100 cc) and ethyl acetate (10 cc), filtered off and washed 4 times with ether (80 cc in total). After drying under reduced pressure (20 mm Hg; 2.7 kPa) at 20° C., a brown powder (950 mg) is obtained which is chromatographed on neutral silica gel (0.04–0.063 mm) (40 g) contained in a column of diameter 2 cm. To do this, the powder (950 mg) is dissolved in a mixture of methanol (30 cc) and concentrated ammonia solution (d=0.92) (0.4 cc), and neutral silica gel (0.04–0.063 mm) (3 g) is added to the solution obtained. The mixture is evaporated to dryness under reduced pressure (20 mm Hg; 2.7 kPa) at 50° C. and the residue thus obtained is charged onto the silica column. Elution is carried out successively with an n-butanol/acetic acid mixture (4/1 by volume) (260 cc) and methanol (320 cc), 20 cc fractions being collected. Fractions 14 to 29 are combined and concentrated to dryness under reduced pressure (20 mm Hg; 2.7 kPa) at 55° C. The residue obtained is triturated in ether (100 cc), filtered off, washed 3 times with ether (60 cc in total) and dried under reduced pressure (0.3 mm Hg; 0.04 kPa) at 50° C. This yields $N^2$-[N-(N-lauroyl-L-alanyl)-γ-D-glutamyl]-L,L-2,7-diamino-4-thiasuberamic acid (450 mg).

Rf=0.33 [silica gel; n-butanol/pyridine/acetic acid/water (50/20/6/24 by volume)].

Mass spectrometry: M=603 (theory=603).

Analysis: Calculated % C 53.71; H 8.18; N 11.60; S 5.31. Found % C 49.5; H 7.6; N 10.3; S 4.93.

$N^7$-Benzyloxycarbonyl-2(L),7(L)-diamino-4-thiasuberamic acid can be prepared in the following manner:

Sodium is added to a solution, cooled to −40° C., of L-cystine (720 mg) in ammonia solution (90 cc), until a persistent blue solution is obtained (about 360 mg of sodium). Ammonium chloride (a few mg) is then added in order to decolorise the reaction medium, followed by methyl N-benzyloxycarbonyl-L-α-amino-γ-bromobutyrate (2 g). The reaction mixture is stirred for ¼ hour at −35° C., methanol (25 cc), cooled to about −35° C., is then added thereto and the mixture is left to stand for 18 hours at 20° C. It is concentrated to dryness under reduced pressure (20 mm Hg) at 45° C. The residue obtained is dissolved in water (50 cc). This solution is acidified to pH 5-6 by adding 1 N acetic acid (6.5 cc). The precipitate formed is filtered off, washed 3 times with water (60 cc in total) and dried under reduced pressure (0.3 mm Hg) at 20° C. This yields $N^7$-benzyloxycarbonyl-2(L),7(L)-diamino-4-thiasuberamic acid (600 mg), which melts at 240°–244° C.

Rf=0.40 [silica gel; n-butanol/pyridine/acetic acid/water (50/20/6/24 by volume)].

Mass spectrometry: M=355 (theory=355).

A second crop of $N^7$-benzyloxycarbonyl-2(L),7(L)-diamino-4-thiasuberamic acid (600 mg) can be obtained in the following manner: the filtrate obtained above is concentrated to 5 cc under reduced pressure (20 mm Hg; 2.7 kPa) at 50° C. The precipitate which has appeared in the concentrate is filtered off, washed twice with water (4 cc in total) and dried under reduced pressure (0.3 mm Hg; 0.04 kPa) at 20° C.

Methyl N-benzyloxycarbonyl-L-α-amino-γ-bromobutyrate can be prepared in accordance with the method of Z. PROCHAZKA et al., Coll. Czech. Chem. Commun. 45, 1,982 (1980).

EXAMPLE 9

Isobutyl chloroformate (2.64 cc) is added to a solution, kept at −5° C., of N-(N-lauroyl-L-alanyl)-D-isoglutamine (8 g) in a mixture of tetrahydrofuran (200 cc), dimethylformamide (400 cc) and triethylamine (2.8 cc). The mixture is stirred for 20 minutes at −5° C. and a solution, cooled to 5° C., of $N^2$-benzyloxycarbonyl-2(L),6(D,L)-diamino-4-thiapimelamic acid hydrochloride (7.56 g) in a mixture of N sodium hydroxide solution (20 cc) and water (80 cc) is then added. The reaction mixture is stirred for a few minutes at about 0° C. and then for 18 hours at about 20° C. The tetrahydrofuran is then removed by concentration under reduced pressure (20 mm Hg; 2.7 kPa) at 50° C. A small amount of insoluble material is removed from the concentrate by filtration and the filtrate is diluted with water (2 liters) and 1 N hydrochloric acid (45 cc). The precipitate formed is filtered off, washed twice with water (400 cc in total) and dried in the open air. This yields a cream-coloured powder (16.1 g) which is chromatographed on neutral silica gel (0.04–0.063 mm) (450 g) contained in a column of diameter 5 cm. To do this, the powder (16.1 g) is dissolved in ethyl acetate (100 cc) warmed to 50° C., and neutral silica gel (0.04–0.063 mm) (30 g) is added to the solution obtained. The mixture is evaporated to dryness under reduced pressure (20 mm Hg; 2.7 kPa) at 50° C. and the residue thus obtained is charged onto the silica column. Elution is carried out successively with an ethyl acetate/acetic acid mixture (1/1 by volume) (1.5 liters), an ethyl acetate/acetic acid mixture (4/6 by volume) (750 cc) and an ethyl acetate/acetic acid mixture (3/7 by volume) (750 cc), 50 cc fractions being collected. Fractions 20 to 60 are combined and concentrated to dryness under reduced pressure (20 mm Hg; 2.7 kPa) at 50° C. The residue obtained is triturated in ethyl acetate (500 cc), filtered off and washed with ether. This yields $N^6$-[N-(N-lauroyl-L-alanyl)-D-isoglutaminyl]-$N^2$-benzyloxycarbonyl-2(L),6(D,L)-diamino-4-thiapimelamic acid (7.1 g).

Rf=0.24 [silica gel; ethyl acetate/acetic acid (7/3 by volume)].

$N^6$-[N-(N-Lauroyl-L-alanyl)-D-isoglutaminyl]-$N^2$-benzyloxycarbonyl-2(L),6(D,L)-diamino-4-thiapimelamic acid (7 g) is dissolved in a mixture of a 33% strength solution of hydrogen bromide in acetic acid (50 cc) and acetic acid (50 cc). The reaction mixture is stirred for 1 hour at 20° C. and concentrated to dryness under reduced pressure (20 mm Hg; 2.7 kPa) at 45° C. The residue obtained is triturated in ethyl acetate (100 cc), filtered off and washed twice with ethyl acetate (100 cc in total) and 3 times with ether (150 cc in total). After drying under reduced pressure (0.3 mm Hg; 0.04 kPa) at 20° C., a pink powder (8.14 g) is obtained which is dissolved in water (500 cc). After stirring for ½ hour, the precipitate which has appeared is filtered off, washed successively twice with water (100 cc in total) and 5 times with ether (250 cc in total) and dried under reduced pressure (0.3 mm Hg; 0.04 kPa) at 20° C. This yields $N^6$-[N-(N-lauroyl-L-alanyl)-D-isoglutaminyl]-2(L),6(D,L)-diamino-4-thiapimelamic acid (5.47 g).

Rf=0.39 [silica gel; n-butanol/pyridine/acetic acid/water (50/20/6/24 by volume)].

Mass spectrometry: M=588 (theory=588).

Analysis: Calculated % C 53.04; H 8.22; N 14.27; S 5.45. Found % C 50.0; H 8.1; N 13.1; S 5.0.

N-Lauroyl-L-alanyl-D-isoglutamine can be prepared in the following manner:

Benzyl N-lauroyl-L-alanyl-D-isoglutaminate (6.6 g) is dissolved in acetic acid (330 cc). Palladium-on-charcoal (containing 3% of palladium) (6.6 g) is added and a slow stream of hydrogen is then passed in for 2 hours. After filtration of the reaction mixture, the filtrate is poured into water (3 liters). After standing for 2 hours at 0° C., the precipitate which has appeared is filtered off, washed twice with water (80 cc in total) and then dried. This yields a product (5.16 g) to which a product (0.5 g) obtained under analogous conditions is added. This mixture is dissolved in boiling methanol (90 cc), and water (45 cc) is added to the solution obtained. After standing for 2 hours at a temperature of the order of 20° C., the crystals which have appeared are filtered off, washed twice with water (60 cc in total) and dried under reduced pressure (20 mm Hg; 2.7 kPa). This yields N-lauroyl-L-alanyl-D-isoglutamine (5.1 g), which melts at 163° C.

Rf=0.18 [silica gel; ethyl acetate/methanol (4/1 by volume)].

Analysis: Calculated % C 60.12; H 9.33; N 10.52. Found % C 60.2; H 9.5; N 10.9.

Benzyl N-lauroyl-L-alanyl-D-isoglutaminate can be prepared in the following manner:

Isobutyl chloroformate (2.54 cc) is added to a solution, kept at 0° C., of lauric acid (3.9 g) in anhydrous toluene (156 cc) and triethylamine (2.7 cc). The mixture is stirred for 20 minutes at 0° C. and a solution, cooled to 0° C., of benzyl L-alanyl-D-isoglutaminate hydrochloride (6.7 g) in water (52 cc) and triethylamine (2.7 cc) is then added. The reaction mixture is stirred for 65 hours at a temperature of the order of 20° C. This yields a reaction mixture of gelatinous appearance, to which ethyl acetate (150 cc) is added. The precipitate is filtered off, washed with water (30 cc) and then dried. This yields benzyl N-lauroyl-L-alanyl-D-isoglutaminate (7.6 g) in the form of a white powder. The aqueous phase of the previous filtrate is extracted twice with ethyl acetate (100 cc in total), this ethyl acetate phase is combined with the organic phase of the filtrate and the whole is washed with 0.1 N hydrochloric acid (125 cc) and water (120 cc), dried over magnesium sulphate and then concentrated to dryness under reduced pressure (20 mm Hg) at 50° C. A further amount of benzyl N-lauroyl-L-alanyl-D-isoglutaminate (1.5 g) is obtained. The product (7.6 g and 1.5 g) is recrystallised from methanol (120 cc). This yields benzyl N-lauroyl-L-alanyl-D-isoglutaminate (6.6 g), which melts at 169° C.

Rf=0.13 [silica gel; ethyl acetate].

Benzyl L-alanyl-D-isoglutaminate hydrochloride can be prepared in accordance with the process of S. KUSUMOTO, Bull. Chem. Soc. Japan 49, 533 (1976).

EXAMPLE 10

By following the procedure of Example 2, but using t-butyl N-(N-lauroyl-L-alanyl)-α-D-glutamate and $N^6$-benzyloxycarbonyl-L,L-2,6-diamino-4-thiapimelamic acid as the starting materials, $N^2$-[N-(N-lauroyl-L-alanyl)-γ-D-glutamyl]-L,L-2,6-diamino-4-thiapimelamic acid is obtained, which, by following the conditions of Example 3, provides $N^2$-[N-(N-lauroyl-L-alanyl)-γ-D-glutamyl]-$N^6$-glycyl-L,L-2,6-diamino-4-thiapimelamic acid.

$N^6$-Benzyloxycarbonyl-L,L-2,6-diamino-4-thiapimelamic acid can be prepared in the following manner:

Methyl $N^6$-benzyloxycarbonyl-L,L-2,6-diamino-4-thiapimelamate hydrochloride (250 mg) is added to a solution of ethanol (3 cc) and 4 N sodium hydroxide solution (0.33 cc). The reaction mixture is stirred for 1¼ hours; N hydrochloric acid (0.65 cc) water (3 cc) are then added in order to bring the pH to neutrality. After standing for 2 hours at 20° C., the precipitate which has appeared is filtered off, washed successively with ethanol (2 cc) and acetone (2 cc) and dried under reduced pressure (20 mm Hg; 2.7 kPa) at 20° C. This yields $N^6$-benzyloxycarbonyl-L,L-2,6-diamino-4-thiapimelamic acid (60 mg).

Rf=0.53 [silica gel; n-butanol/pyridine/acetic acid/water (50/20/6/24 by volume)].

Mass spectrometry: M=341 (theory=341).

Methyl $N^6$-benzyloxycarbonyl-L,L-2,6-diamino-4-thiapimelamate can be prepared in the following manner:

Concentrated hydrochloric acid (d=1.19) (0.25 cc) is added to a solution of methyl $N^2$-trityl-$N^6$-benzyloxycarbonyl-L,L-2,6-diamino-4-thiapimelamate (1.4 g) in acetone (6 cc) and the mixture is stirred for 2 minutes. Isopropyl ether (12 cc) is then added. The oil which has separated out is separated off by decantation, dissolved in acetone (5 cc) and separated out by adding isopropyl ether (20 cc). This oil is separated off by decantation and redissolved in methanol (5 cc). Ethyl acetate is added to this solution until a persistent turbidity is obtained. The precipitate formed in this way is filtered off, washed twice with ethyl acetate (10 cc in total) and dried under reduced pressure (20 mm Hg; 2.7 kPa) at 20° C. This yields methyl $N^6$-benzyloxycarbonyl-L,L-2,6-diamino-4-thiapimelamate hydrochloride (400 mg).

Rf=0.70 [silica gel; n-butanol/pyridine/acetic acid/water (50/20/6/24 by volume)].

Mass spectrometry: M=355 (theory=355).

Methyl $N^2$-trityl-$N^6$-benzyloxycarbonyl-L,L-2,6-diamino-4-thiapimelamate can be prepared in the following manner:

Isobutyl chloroformate (0.56 cc) is added to a solution, kept at −6° C., of $O^1$-methyl-$N^2$-trityl-$N^6$-benzyloxycarbonyl-L,L-2,6-diamino-4-thiapimelic acid (2.6 g) in a mixture of chloroform (26 cc) and triethylamine (0.6 cc). The mixture is stirred for 20 minutes at about −6° C. and a solution, cooled to 0° C., of ammoniacal chloroform (1.4 N) (31 cc) is then added. The reaction mixture is stirred for 1 hour at about 0° C. and then for 25 hours at about 20° C. and then washed with water (50 cc) and dried over sodium sulphate. After concentration to dryness under reduced pressure (20 mm Hg; 2.7 kPa) at 40° C., methyl $N^2$-trityl-$N^6$-benzyloxycarbonyl-L,L-2,6-diamino-4-thiapimelamate (2.9 g) is obtained in the form of a yellow oil.

Rf=0.82 [silica gel; n-butanol/pyridine/acetic acid/water (50/20/6/24 by volume)].

$O^1$-Methyl-$N^2$-trityl-$N^6$-benzyloxycarbonyl-L,L-2,6-diamino-4-thiapimelic acid can be prepared in accordance with the method of I. PHOTAKI et al., J. C. S. PERKIN I, 2,599 (1979).

EXAMPLE 11

Isobutyl chloroformate (0.91 cc) is added to a solution, kept at −7° C., of benzyl N-(N-lauroyl-L-alanyl)-α-D-glutamate (3.43 g) in a mixture of tetrahydrofuran (140 cc) and triethylamine (0.98 cc). The mixture is stirred for 20 minutes at −7° C. and a solution, cooled to 2° C., of $N^2$-benzyloxycarbonyl-L,L-2,6-diamino-4-thiapimelamic acid hydrochloride (2.64 g) in a mixture of N sodium hydroxide solution (14 cc) and water (53 cc) is then added.

The reaction mixture is stirred for 2 minutes at −5° C. and then for 20 hours at about 20° C. The reaction mixture is acidified by adding 4 N hydrochloric acid (5 cc). The tetrahydrofuran is evaporated off by concentration under reduced pressure (20 mm Hg; 2.7 kPa) at 50° C. The concentrate is extracted 5 times with ethyl acetate (300 cc in total). The combined organic phases are washed with water (20 cc) and a saturated solution of sodium chloride (20 cc) and concentrated to dryness under reduced pressure (20 mm Hg; 2.7 kPa) at 50° C. This yields a white powder (5.58 g) which is chromatographed on neutral silica gel (0.04–0.063 mm) (100 g) contained in a column of diameter 2.5 cm. To do this, the powder (5.58 g) is dissolved in acetic acid (50 cc), and neutral silica gel (0.04–0.063 mm) (15 g) is added to the solution obtained. The mixture is evaporated to dryness under reduced pressure (20 mm Hg) at 50° C. and the residue thus obtained is charged onto the silica column. Elution is carried out successively with ethyl acetate (360 cc), an ethyl acetate/acetic acid mixture (98/2 by volume) (360 cc), an ethyl acetate/acetic acid mixture (95/5 by volume) (360 cc) and an ethyl acetate/acetic acid mixture (90/10 by volume) (880 cc), 40 cc fractions being collected. Fractions 27 to 49 are combined and concentrated to dryness under reduced pressure (20 mm Hg; 2.7 kPa) at 50° C. The oily residue obtained is triturated in a mixture of ether (45 cc) and petroleum ether (15 cc), filtered off and dried. This yields $N^6$-[$O^1$-benzyl-N-(N-lauroyl-L-alanyl)-$\gamma$-D-glutamyl]-$N^2$-benzyloxycarbonyl-L,L-2,6-diamino-4-thiapimelamic acid (2.52 g).

Rf=0.50 [silica gel; ethyl acetate/acetic acid (9/1 by volume)].

$N^6$-[$O^1$-Benzyl-N-(N-lauroyl-L-alanyl)-$\gamma$-D-glutamyl]-$N^2$-benzyloxycarbonyl-L,L-2,6-diamino-4-thiapimelamic acid (2.5 g) is dissolved in a mixture of methanol (7 cc) and 1 N sodium hydroxide solution (6.75 cc).

The reaction mixture is stirred for 80 minutes. A small amount of insoluble material is removed by filtration. Water (10 cc) is added to the filtrate and the mixture is acidified by adding 1 N hydrochloric acid (8 cc). An oily precipitate forms. The whole is extracted 4 times with ethyl acetate (80 cc in total). The combined organic phases are washed with water (3 cc), dried over sodium sulphate and concentrated to dryness under reduced pressure (20 mm Hg; 2.7 kPa) at 50° C. This yields an oil which is triturated in ether (50 cc), and the solid is filtered off and dried under reduced pressure (20 mm Hg; 2.7 kPa) at 20° C. This yields $N^6$-[N-(N-lauroyl-L-alanyl)-$\gamma$-D-glutamyl]-$N^2$-benzyloxycarbonyl-L,L-2,6-diamino-4-thiapimelamic acid (2.18 g).

Rf=0.47 [silica gel; n-butanol/pyridine/acetic acid/water (50/20/6/24 by volume)].

Mass spectrum: M=723 (theory=723).

$N^6$-[N-(N-Lauroyl-L-alanyl)-$\gamma$-D-glutamyl]-$N^2$-benzyloxycarbonyl-L,L-2,6-diamino-4-thiapimelamic acid (2.13 g) is dissolved in a mixture of a 33% strength solution of hydrogen bromide in acetic acid (8.5 cc) and acetic acid (8.5 cc). The reaction mixture is stirred for 2 hours and concentrated to dryness under reduced pressure (20 mm Hg; 2.7 kPa) at 50° C. The residue thus obtained is triturated in ether (100 cc), filtered off and taken up in water (600 cc), whilst stirring vigorously; it solubilises instantaneously in water and then precipitates after a few minutes. After 1 hour, it is filtered off, washed 5 times with water (250 cc in total) and dried under reduced pressure (0.3 mg Hg; 0.04 kPa) at 60° C. This yields $N^6$-[N-(N-lauroyl-L-alanyl)-$\gamma$-D-glutamyl]-L,L-2,6-diamino-4-thiapimelamic acid (1.33 g).

Rf=0.30 [silica gel; n-butanol/pyridine/acetic acid/water (50/20/6/24 by volume)].

Rf=0.43 [silica gel; acetic acid].

Analysis: Calculated % C 52.95; H 8.03; N 11.88; S 5.44. Found % C 51.1; H 8.0; N 11.1; S 4.8.

Mass spectrum: M=589 (theory=589).

$N^2$-Benzyloxycarbonyl-L,L-2,6-diamino-4-thiapimelamic acid can be prepared in accordance with one of the following methods:

(a) $N^2$-Benzyloxycarbonyl-$N^6$-t-butoxycarbonyl-L,L-2,6-diamino-4-thiapimelamic acid (5.48 g) is dissolved in a 1.7 N anhydrous solution of hydrogen chloride in acetic acid (50 cc). The solution is stirred for 1 hour, anhydrous ether (500 cc) is then added and the mixture is stirred for ¾ hour. The precipitate which has formed is filtered off, washed twice with ether (60 cc in total) and dried under reduced pressure (0.3 mm Hg; 0.04 kPa) at 20° C. This yields $N^2$-benzyloxycarbonyl-L,L-2,6-diamino-4-thiapimelamic acid hydrochloride (2.98 g).

Rf=0.47 [silica gel; n-butanol/pyridine/acetic acid/water (50/20/6/24 by volume)].

After hydrolysis, derivative formation and chromatography on an optically active capillary column:
L-lanthionine 95.7% (theory=1)
D-lanthionine <0.5% (theory=0)
meso-lanthionine 4.3% (theory=0)
are obtained.

$N^2$-Benzyloxycarbonyl-$N^6$-t-butoxycarbonyl-L,L-2,6-diamino-4-thiapimelamic acid can be prepared in the following manner:

Sodium is added in small portions to a solution, kept at about −75° C., of di-t-butoxycarbonyl-L-cystinamide (4 g) in ammonia solution (200 cc), until a persistent blue coloration is obtained for a few minutes. Ammonium chloride is then added until the reaction medium has been decolorised, followed by L-$\alpha$-benzyloxycarbonyl-amino-$\beta$-chloropropionic acid (4.7 g). The reaction mixture is left to stand for 18 hours at about 20° C. The cream-coloured solid thus obtained is taken up in water (80 cc); the aqueous solution is acidified to pH 2 by adding a saturated solution of citric acid, and extracted 5 times with ethyl acetate (150 cc in total). The combined organic phases are washed with water (20 cc), dried over sodium sulphate and concentrated to dryness under reduced pressure (20 mm Hg; 2.7 kPa) at 50° C. This yields a yellow oil (7.5 g) which is chromatographed on neutral silica gel (0.04–0.63 mm) (125 g). Elution is carried out with ethyl acetate, 40 cc fractions being collected. Fractions 7 to 16 are combined and concentrated to dryness under reduced pressure (20 mm Hg; 2.7 kPa) at 50° C. The oil obtained is dissolved in ethyl acetate (50 cc) and the solution is extracted 4 times with a decinormal solution of sodium hydroxide (200 cc in total). The combined aqueous phases are acidified to pH 2 by adding a saturated solution of citric acid, and extracted 4 times with ethyl acetate (100 cc in total). The combined organic phases are dried over sodium sulphate and concentrated to dryness under reduced pressure (20 mm Hg; 2.7 kPa) at 50° C. This yields $N^2$-benzyloxycarbonyl-$N^6$-t-butoxycarbonyl-L,L-2,6-diamino-4-thiapimelamic acid (2.5 g).

Rf=0.62 [silica gel; ethyl acetate/acetic acid (9/1 by volume)].

di-t-Butoxycarbonyl-L-cystinamide can be prepared in the following manner:

Isobutyl chloroformate (16.6 cc) is added to a solution, kept at −5° C., of di-t-butoxycarbonyl-L-cystine (25 g) in a mixture of tetrahydrofuran (500 cc) and triethylamine (15.9 cc). The mixture is stirred for 20 minutes at −5° C. and a 1.4 N ammoniacal solution of chloroform (125 cc) is then added in the course of ¼ hour. Then, whilst keeping the temperature at about −5° C., the reaction mixture is saturated for ½ hour with a stream of anhydrous ammonia gas and then stirred for 20 hours at about 20° C. Tetrahydrofuran (100 cc) is added and the insoluble material is filtered off, washed 6 times with water (2.25 liters in total) and then with ethyl acetate (1 liter) and dried in the open air. This yields di-t-butoxycarbonyl-L-cystinamide (16.98 g).

Rf=0.85 [silica gel; n-butanol/pyridine/acetic acid/water (50/20/6/24 by volume)].

Rf=0.77 [silica gel; methanol].

(b) $O^1$-Methyl-$N^6$-benzyloxycarbonyl-L,L-2,6-diamino-4-thiapimelic acid hydrochloride (950 mg) is added to 2.3 N ammoniacal ethanol (11 cc) and the solution obtained is kept for 70 hours at about 20° C. A small amount of insoluble material is then removed by filtration and the filtrate is concentrated to dryness under reduced pressure (20 mm Hg; 2.7 kPa) at 50° C. The residue obtained is triturated in acetone (20 cc), filtered off and dried under reduced pressure (20 mm Hg; 2.7 kPa) at 20° C. This yields $N^2$-benzyloxycarbonyl-L,L-2,6-diamino-4-thiapimelamic acid (0.18 g).

Rf=0.62 [silica gel; n-butanol/pyridine/acetic acid/water (50/20/6/24 by volume)].

Mass spectrometry: M=341 (theory=341).

$O^1$-Methyl-$N^6$-benzyloxycarbonyl-L,L-2,6-diamino-4-thiapimelic acid can be prepared in the following manner:

Concentrated hydrochloric acid (d=1.19) (0.52 cc) is added to a solution of $O^1$-methyl-$N^2$-trityl-$N^6$-benzyloxycarbonyl-L,L-2,6-diamino-4-thiapimelic acid (3 g) in acetone (13 cc) and the mixture is stirred for 2 minutes. The reaction mixture is then poured into ether (25 cc). The oil which has separated out is separated off by decantation and triturated in a mixture of acetone (5 cc) and ether (25 cc). The white solid formed is filtered off, dissolved in methanol (5 cc) and reprecipitated by adding ethyl acetate (50 cc) and ether (25 cc). After filtration, washing with ether (20 cc) and drying under reduced pressure (20 mm Hg; 2.7 kPa) at 20° C., $O^1$-methyl-$N^6$-benzyloxycarbonyl-L,L-2,6-diamino-4-thiapimelic acid hydrochloride (1 g) is obtained.

Rf=0.64 [silica gel; n-butanol/pyridine/acetic acid/water (50/20/6/24 by volume)].

EXAMPLE 12

By following the procedure of Example 3, but using N-t-butoxycarbonylglycine and $N^6$-[N-(N-lauroyl-L-alanyl)-γ-D-glutamyl]-L,L-2,6-diamino-4-thiapimelamic acid as the starting materials, $N^6$-[N-(N-lauroyl-L-alanyl)-γ-D-glutamyl]-$N^2$-glycyl-L,L-2,6-diamino-4-thiapimelamic acid is obtained.

EXAMPLE 13

Isobutyl chloroformate (1.95 cc) is added to a solution, kept at −7° C., of t-butyl N-(N-lauroyl-L-alanyl)-α-D-glutamate (6.84 g) in a mixture of tetrahydrofuran (330 cc) and triethylamine (2.1 cc). The mixture is stirred for 20 minutes at −7° C. and a solution, cooled to 10° C., of $N^6$-benzyloxycarbonyl-2(D),6(L)-diamino-4-thiapimelamic acid (5.11 g) in a mixture of 1 N sodium hydroxide solution (15 cc) and water (130 cc) is then added.

The reaction mixture is stirred for 5 minutes at 0° C. and then for 24 hours at about 20° C. The tetrahydrofuran is evaporated off by concentration under reduced pressure (20 mm Hg; 2.7 kPa) at 50° C.; the concentrate is cooled to 0° C. and acidified to pH 2 by adding 1 N hydrochloric acid. The precipitate formed is filtered off, washed with 0.1 N hydrochloric acid (50 cc) and then twice with water (200 cc in total) and dried in air. This yields $N^2$-[$O^1$-t-butyl-N-(N-lauroyl-L-alanyl)-γ-D-glutamyl]-$N^6$-benzyloxycarbonyl-2(D),6(L)-diamino-4-thiapimelamic acid (10 g).

Rf=0.65 [silica gel; n-butanol/pyridine/acetic acid/water (50/20/6/24 by volume)].

Rf=0.72 [silica gel; ethyl acetate/acetic acid (3/1 by volume)].

$N^2$-[$O^1$-t-butyl-N-(N-lauroyl-L-alanyl)-γ-D-glutamyl]-$N^6$-benzyloxycarbonyl-2(D),6(L)-diamino-4-thiapimelamic acid (5 g) is dissolved in a 35% strength solution of hydrogen bromide in acetic acid (22 cc). The reaction mixture is agitated for ½ hour with an ultrasonic agitator and then poured into anhydrous ether (1 liter) cooled to 0° C. The mixture is stirred for 1 hour; the precipitate obtained is filtered off, washed 4 times with ether (400 cc in total) and dissolved in methanol (100 cc). Ammonia solution (d=0.92) (5 cc) is added to the solution obtained. The mixture is concentrated to dryness under reduced pressure (20 mm Hg; 2.7 kPa) at 50° C. This yields a white powder (4.36 g) which is chromatographed on neutral silica gel (0.04–0.063 mm) (200 g) contained in a column of diameter 3.5 cm. Elution is carried out with a mixture of methanol and ammonia solution (d=0.92) (999.5/0.5 by volume), 30 cc fractions being collected. Fractions 25 to 39 are combined and concentrated to dryness under reduced pressure (20 mm Hg) at 50° C. This yields a white powder (2.8 g) which is chromatographed on neutral silica gel (0.04–0.063 mm) (100 g) contained in a column of diameter 3 cm. To do this, the powder (2.8 g) is dissolved in methanol (50 cc) containing ammonia solution (d=0.92) (0.5 cc per liter), and neutral silica gel (0.04–0.063 mm) (3 g) is added to the solution thus obtained. The mixture is evaporated to dryness under reduced pressure (20 mm Hg; 2.7 kPa) at 50° C. and the residue thus obtained is charged onto the silica column. Elution is carried out with a mixture of methanol and ammonia solution (d=0.92) (999.5/0.5 by volume), 15 cc fractions being collected. Fractions 13 to 23 are combined and concentrated to dryness under reduced pressure (20 mm Hg; 2.7 kPa) at 50° C. This yields $N^2$-[N-(N-lauroyl-L-alanyl)-γ-D-glutamyl]-2(D),6(L)-diamino-4-thiapimelamic acid (0.71 g).

Rf=0.35 [silica gel; n-butanol/pyridine/acetic acid/water (50/20/6/24 by volume)].

Analysis: Calculated % C 52.95; H 8.03; N 11.87; S 5.44. Found % C 50.2; H 7.8; N 11.6; S 5.3.

Sulphuric ash=7.3%.

Mass spectrum: M=589 (theory=589).

$N^6$-Benzyloxycarbonyl-2(D),6(L)-diamino-4-thiapimelamic acid can be prepared in the following manner:

A 5.6 N methanolic solution of sodium methoxide (12.6 cc) is added to a solution, kept at about −70° C., of N-benzyloxycarbonyl-L-cysteinamide (17.93 g) in ammonia solution (570 cc), and D-α-amino-β-chloropropionic acid hydrochloride (11.3 g) is then added in small portions in the space of 10 minutes. The reaction mixture is stirred for 10 minutes at about −60° C. and then left to stand for 20 hours at about 20° C. The residue thus obtained is taken up in water (200 cc); insoluble material is removed from the aqueous phase by filtration and the filtrate is extracted twice with ethyl acetate (400 cc in total), acidified to pH 2 by adding 10 N hydrochloric acid, extracted twice with ethyl acetate (400 cc in total), concentrated to a volume of 170 cc under reduced pressure (20 mm Hg; 2.7 kPa) at 50° C., brought to pH 5–6 by adding triethylamine and cooled at 0° C. for 2 hours. The insoluble material which has appeared in the aqueous phase is filtered off, washed 3 times with water (150 cc in total) and dried successively in air and under reduced pressure (0.3 mm Hg; 0.04 kPa) at 50° C. This yields $N^6$-benzyloxycarbonyl-2(D),6(L)-diamino-4-thiapimelamic acid (8.88 g).

Rf=0.48 [silica gel; n-butanol/pyridine/acetic acid/water (50/20/6/24 by volume)].

$[\alpha]_D^{20}$ = −20° (1 N sodium hydroxide solution; c=1).

Mass spectrometry: M=341 (theory=341)

After hydrolysis, derivative formation and chromatography on an optically active capillary column:
  meso-Lan 100% (theory=1)
  L-Lan <0.5% (theory=0)
  D-Lan <0.5% (theory=0)
are obtained.

EXAMPLE 14

Isobutyl chloroformate (1.92 cc) is added to a solution, kept at −10° C., of t-butyl N-(N-lauroyl-L-alanyl)-α-D-glutamate (6.66 g) in a mixture of tetrahydrofuran (320 cc) and triethylamine (2 cc). The mixture is stirred for 20 minutes at −10° C. and a solution, cooled to 10° C., of $N^6$-benzyloxycarbonyl-L,L-2,6-diamino-4-thiapimelamic acid (5 g) in a mixture of 1 N sodium hydroxide solution (14.6 cc) and water (120 cc) is then added.

The reaction mixture is stirred for 5 minutes at 0° C. and then for 20 hours at about 20° C. The tetrahydrofuran is evaporated off by concentration under reduced pressure (20 mm Hg; 2.7 kPa) at 50° C.; the concentrate is diluted with water (200 cc) and acidified to pH 2 by adding 1 N hydrochloric acid (about 25 cc). Ethyl acetate (500 cc) is added to the suspension thus obtained. After stirring the mixture, the insoluble material is filtered off and dried under reduced pressure (0.3 mm Hg; 0.04 kPa) at 20° C. This yields a powder (2.55 g) with which a powder (4.45 g), obtained in the following manner, is combined: the organic phase is separated from the filtrate, dried over sodium sulphate and concentrated to dryness under reduced pressure (20 mm Hg; 2.7 kPa) at 50° C. The residue obtained is taken up in ethyl acetate (200 cc). The pale yellow solution thus obtained is cooled at 0° C. for 1 hour. The precipitate formed is filtered off, washed twice with ether (200 cc in total) and dried under reduced pressure (0.3 mm Hg; 0.04 kPa) at 20° C. The powder (7 g) thus obtained is chromatographed on neutral silica gel (0.04–0.063 mm) (140 g) contained in a column of diameter 3.2 cm. To do this, the powder (7 g) is dissolved in acetic acid (50 cc), and neutral silica gel (0.04–0.063 mm) (14 g) is added to the solution obtained. The mixture is evaporated to dryness under reduced pressure (20 mm Hg; 2.7 kPa) at 50° C. and the residue thus obtained is charged onto the silica column. Elution is carried out successively with an ethyl acetate/acetic acid mixture (9/1 by volume) (2.15 liters) and an ethyl acetate/acetic acid mixture (1/1 by volumne) (0.3 liter), 50 cc fractions being collected. Fractions 10 to 49 are combined and concentrated to dryness under reduced pressure (20 mm Hg; 2.7 kPa) at 50° C.

The oily residue obtained is taken up in ethyl acetate (100 cc). The solution obtained is cooled at 0° C. for 1 hour. The precipitate formed is filtered off, washed twice with ether (100 cc in total) and dried under reduced pressure (0.3 mm Hg; 0.04 kPa) at 20° C. This yields $N^2$-[$O^1$-t-butyl-N-(N-lauroyl-L-alanyl)-γ-D-glutamyl]-$N^6$-benzyloxycarbonyl-L,L-2,6-diamino-4-thiapimelamic acid (3.4 g).

Rf=0.63 [silica gel; ethyl acetate/acetic acid (3/1 by volume)].

$N^2$-[$O^1$-t-Butyl-N-(N-lauroyl-L-alanyl)-γ-D-glutamyl]-$N^6$-benzyloxycarbonyl-L,L-2,6-diamino-4-thiapimelamic acid (3.4 g) is dissolved in a mixture of a 35% strength solution of hydrogen bromide in acetic acid (17 cc) and acetic acid (10 cc). The reaction medium is stirred for 2 hours and concentrated to dryness under reduced pressure (20 mm Hg; 2.7 kPa) at 55° C.

The oily residue obtained is triturated in ethyl acetate (30 cc), filtered off, washed twice with ether (60 cc in total) and dried under reduced pressure (20 mm Hg; 2.7 kPa) at 20° C. This yields a beige powder (4 g) which is chromatographed on neutral silica gel (0.04–0.063 mm) (90 g) contained in a column of diameter 3 cm. To do this, the powder (4 g) is dissolved in methanol (50 cc) to which ammonia solution (d=0.92) (7 cc) and neutral silica gel (0.04–0.063 mm) (8 g) are added. The mixture is evaporated to dryness under reduced pressure (20 mm Hg; 2.7 kPa) at 50° C. and the residue thus obtained is charged onto the silica column. Elution is carried out with a mixture of methanol and ammonia solution (d=0.92) (999.5/0.5 by volume), 10 cc fractions being collected. Fractions 13 to 24 are combined and concentrated to dryness under reduced pressure (20 mm Hg; 2.7 kPa) at 50° C. The pasty residue is triturated in ether (100 cc), filtered off and dried under reduced pressure (20 mm Hg; 2.7 kPa) at 20° C. This yields a powder (2.4 g) which is chromatographed on neutral silica gel (0.04–0.063 mm) (90 g) contained in a column of diameter 3 cm. To do this, the powder (2.4 g) is dissolved in methanol (30 cc) to which neutral silica gel (0.04–0.063 mm) (4 g) is added. The mixture is evaporated to dryness under reduced pressure (20 mm Hg; 2.7 kPa) at 50° C. and the residue thus obtained is charged onto the silica column. Elution is carried out with a mixture of methanol and ammonia solution (d=0.92) (999.5–0.5 by volume), 5 cc fractions being collected. Fractions 22 to 30 are combined and concentrated to dryness under reduced pressure (20 mm Hg; 2.7 kPa) at 50° C. The residue obtained is triturated in ether (50 cc), filtered off and dried under reduced pressure (20 mm Hg; 2.7 kPa) at 50° C. This yields a powder (1.54 g). This powder (1 g) is suspended in water (50 cc). The powder is dissolved by bringing the pH of the mixture to 1.8 by adding 0.1 N hydrochloric acid (40 cc). The pH is then brought to 3.6 by adding 0.1 N sodium hydroxide solution (20 cc). The precipitate which has appeared is filtered off, washed with water (30 cc) and dried in air and then under reduced pressure (0.3 mm Hg; 0.04 kPa) at 50° C. This yields $N^2$-[N-(N-lauroyl-L-alanyl)-γ-D-glutamyl]-L,L-2,6-diamino-4-thiapimelamic acid (0.66 g).

Rf=0.36 [silica gel; n-butanol/pyridine/acetic acid/water (50/20/6/24 by volume)].

Analysis: Calculated % C 52.95; H 8.03; N 11.87; S 5.44. Found % C 52.0; H 8.2; N 11.5; S 5.4.

Mass spectrum: M=589 (theory=589).

$N^6$-Benzyloxycarbonyl-L,L-2,6-diamino-4-thiapimelamic acid can be prepared in the following manner:

A 5.8 N solution of sodium methoxide in methanol (1.72 cc) is added to a solution, kept at about −75° C., of N-benzyloxycarbonyl-L-cysteinamide (2.54 g) in ammonia solution (80 cc). L-α-Amino-β-chloropropionic acid hydrochloride (1.6 g) is then added. The reaction medium is left to stand for 18 hours at about 20° C. The solid residue obtained is taken up in water (50 cc), insoluble material is removed from the aqueous phase by filtration and the filtrate is extracted 3 times with ethyl acetate (60 cc in total), acidified to pH 3-4 by adding citric acid and cooled to 0° C. After standing for 2 hours at 0° C., the precipitate which has appeared is filtered off, washed with water (10 cc), 3 times with ethyl acetate (30 cc in total) and 3 times with ether (30 cc in total) and dried under reduced pressure (20 mm Hg; 2.7 kPa) at 20° C. This yields N⁶-benzyloxycarbonyl-L,L-2,6-diamino-4-thiapimelamic acid (0.83 g).

Rf=0.54 [silica gel; n-butanol/pyridine/acetic acid/water (50/20/6/24 by volume)].

After hydrolysis, derivative formation and chromatography on an optically active capillary column:
L-Lan: 99.2% (theory: 1)
meso-Lan: 0.8% (theory: 0)
D-Lan: <0.5% (theory: 0)
are obtained.

EXAMPLE 15

Isobutyl chloroformate (0.53 cc) is added to a solution, kept at −5° C., of t-butyl N-(N-lauroyl-L-alanyl)-α-D-glutamate (1.88 g) in a mixture of tetrahydrofuran (100 cc) and triethylamine (0.58 cc). The mixture is stirred for 20 minutes at −5° C. and a solution, cooled to 2° C., of N⁶-t-butoxycarbonylglycyl-L,L-2,6-diamino-4-thiapimelamic acid (1.5 g) in a mixture of 1 N sodium hydroxide solution (4.1 cc) and water (35 cc) is then added.

The reaction mixture is stirred for 5 minutes at 10° C. and then for 20 hours at about 20° C. The tetrahydrofuran is evaporated off by concentration under reduced pressure (20 mm Hg; 2.7 kPa) at 50° C.; the concentrate is cooled to 0° C. and acidified to pH 2 by adding 1 N hydrochloric acid (about 7 cc).

The reaction mixture is extracted 3 times with ethyl acetate (200 cc in total). The combined organic phases are dried over sodium sulphate and concentrated to dryness under reduced pressure (20 mm Hg; 2.7 kPa) at 50° C. This yields an oil which, when triturated in ether (100 cc), gives a powder (2.1 g) which is chromatographed on neutral silica gel (0.04–0.063 mm) (60 g) contained in a column of diameter 2.2 cm. To do this, the powder (2.1 g) is dissolved in acetic acid (20 cc), and neutral silica gel (0.04–0.063 mm) (4 g) is added to the solution obtained. The mixture is evaporated to dryness under reduced pressure (20 mm Hg) at 50° C. and the residue thus obtained is charged onto the silica column. Elution is carried out with an ethyl acetate/acetic acid mixture (9/1 by volume), 20 cc fractions being collected. Fractions 13 to 42 are combined and concentrated to dryness under reduced pressure (20 mm Hg; 2.7 kPa) at 50° C. The residue obtained is triturated in ether (200 cc), filtered off and dried. This yields N²-[O¹-t-butyl-N-(N-lauroyl-L-alanyl)-γ-D-glutamyl]-N⁶-t-butoxycarbonylglycyl-L,L-2,6-diamino-4-thiapimelamic acid (1.3 g).

Rf=0.49 [silica gel; ethyl acetate/acetic acid (8/2 by volume)].

N²-[O¹-t-Butyl-N-(N-lauroyl-L-alanyl)-γ-D-glutamyl]-N⁶-t-butoxycarbonylglycyl-L,L-2,6-diamino-4-thiapimelamic acid (1.3 g) is dissolved in a 1.7 N anhydrous solution of hydrogen chloride in acetic acid (30 cc). The reaction mixture is stirred for 1 hour, a very small amount of insoluble material is removed therefrom by filtration and the filtrate is concentrated to dryness under reduced pressure (20 mm Hg; 2.7 kPa) at 50° C. The residue thus obtained is triturated in ethyl acetate (50 cc), filtered off, washed successively with ethyl acetate (30 cc) and twice with ether (60 cc in total) and dried. This yields a powder (0.9 g) which is chromatographed on neutral silica gel (0.04–0.063 mm) (30 g) contained in a column of diameter 2.1 cm. Elution is carried out with acetic acid, 10 cc fractions being collected. Fractions 13 to 20 are combined and concentrated to dryness under reduced pressure (20 mm Hg; 2.7 kPa) at 50° C. The residue obtained is triturated in ethyl acetate (50 cc), filtered off, washed with ether (30 cc) and dried. This yields a powder (0.79 g) which is dissolved in water (40 cc). The aqueous phase is brought to pH 3.5 by adding 0.1 N sodium hydroxide solution (6 cc). The precipitate which has appeared is filtered off, washed with water (20 cc) and dried under reduced pressure (20 mm Hg; 2.7 kPa) at 50° C. This yields N²-[N-(N-lauroyl-L-alanyl)-γ-D-glutamyl]-N⁶-glycyl-L,L-2,6-diamino-4-thiapimelamic acid (0.59 g).

Rf=0.34 [silica gel; n-butanol/pyridine/acetic acid/water (50/20/6/24 by volume)].

Analysis: Calculated % C 51.99; H 7.99; N, 12.99; S 4.96. Found % C 49.9; H 8.0; N 12.8; S 4.9.

Sulphuric ash: 0.9%.

N⁶-t-Butoxycarbonylglycyl-2(L),6(L)-diamino-4-thiapimelamic acid can be prepared in the following manner:

Sodium is added in small portions to a solution, kept at about −75° C., of di-t-butoxycarbonylglycyl-L-cystinamide (4.6 g) in ammonia solution (400 cc), until a persistent blue coloration is obtained for a few minutes. Ammonium chloride is then added until the reaction mixture has been decolorised, followed by L-α-amino-β-chloropropionic acid hydrochloride (2.66 g). The reaction mixture is stirred for 2 hours at about −75° C. and then left to stand for 18 hours at about 20° C. The white paste thus obtained is triturated in ethanol (100 cc) and the mixture is filtered. The filtrate is concentrated to dryness under reduced pressure (20 mm Hg; 2.7 kPa) at 50° C. The oily residue is triturated in acetic acid (50 cc) and the mixture is filtered. The filtrate is concentrated to dryness under reduced pressure (20 mm Hg; 2.7 kPa) at 50° C. This operation is repeated twice with methanol (60 cc in total). This yields an oily residue (10.5 g) which is chromatographed on neutral silica gel (0.04–0.063 mm) (250 g) contained in a column of diameter 3.5 cm. To do this, the residue (10.5 g) is dissolved in methanol (50 cc), and neutral silica gel (0.04–0.063 mm) (20 g) is added to the solution obtained. The mixture is evaporated to dryness under reduced pressure (20 mm Hg; 2.7 kPa) at 50° C. and the residue thus obtained is charged onto the silica column. Elution is carried out successively with an ethyl acetate/methanol mixture (1/1 by volume) (1.15 liters) and an ethyl acetate/methanol mixture (2/8 by volume) (850 cc), 50 cc fractions being collected. Fractions 26 to 33 are combined and concentrated to dryness under reduced pressure (20 mm Hg; 2.7 kPa) at 50° C. The residue obtained is triturated in ethyl acetate (50 cc), filtered off, washed with ethyl acetate (20 cc) and dried under reduced pressure (0.3 mm Hg; 0.04 kPa) at 50° C. This yields N⁶-t-butoxycarbonylglycyl-2(L),6(L)-diamino-4-thiapimelamic acid (2 g).

Rf=0.41 [silica gel; n-butanol/pyridine/acetic acid/water (50/20/6/24 by volume)].

[α]$_D^{20}$= −9° (1 N sodium hydroxide solution; c=1).

After hydrolysis, derivative formation and chromatography on an optically active capillary column:
L-Lan: 95.5% (theory=1)
D-Lan: <0.5% (theory=0)
meso-Lan: 4.5% (theory=0)
are obtained.

di-t-Butoxycarbonylglycyl-L-cystinamide can be prepared in the following manner:

Isobutyl chloroformate (13 cc) is added to a solution, kept at −5° C., of t-butoxycarbonylglycine (17.6 g) in a mixture of tetrahydrofuran (1.7 liters) and triethylamine (14 cc). The mixture is stirred for 20 minutes at about −5° C. and a solution, cooled to about 5° C., of L-cystinamide hydrobromide (20 g) in a mixture of 1 N sodium hydroxide solution (100 cc) and water (1 liter) is then added. The reaction mixture is stirred for a few minutes at about 0° C. and then for 18 hours at about 20° C. The tetrahydrofuran is then removed by concentration under reduced pressure (20 mm Hg; 2.7 kPa) at 50° C. The concentrate is acidified to pH 3 by adding citric acid and extracted 3 times with ethyl acetate (1.5 liters in total). The ethyl acetate phase is dried over sodium sulphate and concentrated to dryness under reduced pressure (20 mm Hg; 2.7 kPa) at 50° C. The residue obtained is taken up in ether (700 cc), filtered off and washed twice with ether (200 cc in total). This yields a powder (19 g). This powder (15 g) is chromatographed on neutral silica gel (0.04–0.063 mm) (600 g) contained in a column of diameter 4.8 cm. To do this, the product (15 g) is dissolved in methanol (100 cc), and neutral silica gel (0.04–0.063 mm) (15 g) is added to the solution obtained. The mixture is evaporated to dryness under reduced pressure (20 mm Hg; 2.7 kPa) at 50° C. and the residue thus obtained is charged onto the silica column. Elution is carried out successively with an ethyl acetate/acetic acid mixture (97/3 by volume) (2.1 liters), an ethyl acetate/acetic acid mixture (96/4 by volume) (1.9 liters), an ethyl acetate/acetic acid mixture (95/5 by volume) (850 cc), an ethyl acetate/acetic acid mixture (94/6 by volume) (1.7 liters), an ethyl acetate/acetic acid mixture (9/1 by volume) (850 cc), an ethyl acetate/acetic acid mixture (8/2 by volume) (900 cc) and an ethyl acetate/acetic acid mixture (1/1 by volume) (950 cc), 50 cc fractions being collected. Fractions 150 to 182 are combined and concentrated to dryness under reduced pressure (20 mm Hg; 2.7 kPa) at 50° C. The oily residue obtained is triturated in ether (400 cc), filtered off, washed twice with ether (200 cc in total) and dried under reduced pressure (0.3 mm Hg; 0.04 kPa) at 50° C. This yields di-t-butoxycarbonylglycyl-L-cystinamide (7.5 g).

Rf=0.38 [silica gel; ethyl acetate/acetic acid (9/1 by volume)].

EXAMPLE 16

Isobutyl chloroformate (1.15 cc) is added to a solution, kept at −6° C., of N-(N-lauroyl-L-alanyl)-D-isoglutamine (3.51 g) in a mixture of dimethylformamide (260 cc) and triethylamine (1.23 cc). The mixture is stirred for 20 minutes at −6° C. and a solution, cooled to 5° C., of $N^6$-benzyloxycarbonyl-2(L),6(D,L)-diamino-4-thiapimelamic acid (3 g) in a mixture of 1 N sodium hydroxide solution (8.8 cc) and water (70 cc) is then added.

The reaction mixture is stirred for 10 minutes at 5° C. and then for 24 hours at about 20° C. A small amount of insoluble material is removed therefrom by filtration and the filtrate is diluted with water (700 cc) and acidified to pH 2 by adding 4 N hydrochloric acid (about 6 cc). The precipitate which has appeared is filtered off, washed successively with 0.1 N hydrochloric acid (100 cc) and 3 times with water (600 cc in total) and dried in air. This yields a white powder (5.6 g) which is chromatographed on neutral silica gel (0.04–0.063 mm) (168 g) contained in a column of diameter 3.5 cm. To do this, the powder (5.6 g) is dissolved in acetic acid (30 cc), and neutral silica gel (0.04–0.063 mm) (12 g) is added to the solution obtained. The mixture is evaporated to dryness under reduced pressure (20 mm Hg; 2.7 kPa) at 50° C. and the residue thus obtained is charged onto the silica column. Elution is carried out successively with an ethyl acetate/acetic acid mixture (7/3 by volume), 100 cc fractions being collected. Fractions 13 to 38 are combined and concentrated to dryness under reduced pressure (20 mm Hg; 2.7 kPa) at 50° C. The residue obtained is triturated in ether (100 cc), filtered off and dried. This yields $N^2$-[N-(N-lauroyl-L-alanyl)-D-isoglutaminyl]-$N^6$-benzyloxycarbonyl-2(L),6(D,L)-diamino-4-thiapimelamic acid (3.3 g).

$N^2$-[N-(N-Lauroyl-L-alanyl)-D-isoglutaminyl]-$N^6$-benzyloxycarbonyl-2(L),6(D,L)-diamino-4-thiapimelamic acid (2.25 g) is dissolved in a 35% strength solution of hydrogen bromide in acetic acid (16 cc). The reaction mixture is agitated for 35 minutes with an ultrasonic agitator and then poured into ether (1.5 liters). The mixture is stirred for 2 hours. The precipitate obtained is filtered off, washed 3 times with ether (150 cc in total) and dissolved in water (350 cc). The aqueous phase is neutralised to pH 7 by adding 0.1 N ammonia solution. After standing for 16 hours at 20° C., the precipitate which has appeared is filtered off, washed successively twice with water (100 cc in total) and with ether (100 cc), acetone (50 cc), ethyl acetate (50 cc), methanol (50 cc) and ether (50 cc) and dried under reduced pressure (0.3 mm Hg; 0.04 kPa) at 20° C. This yields a powder (0.8 g) with which a powder (0.3 g) obtained in a similar experiment is combined, and the whole is chromatographed on neutral silica gel (0.04–0.063 mm) (55 g) contained in a column of diameter 2.5 cm. To do this, the powder (1.1 g) is dissolved in acetic acid (20 cc), and neutral silica gel (0.04–0.063 mm) (3 g) is added to the solution obtained. The mixture is evaporated to dryness under reduced pressure (20 mm Hg; 2.7 kPa) at 50° C. and the residue thus obtained is charged onto the silica column. Elution is carried out with a mixture of methanol, ethyl acetate and ammonia solution (d=0.92) (65/35/0.25 by volume), 50 cc fractions being collected. Fractions 7 to 13 are combined and concentrated to dryness under reduced pressure (20 mm Hg; 2.7 kPa) at 50° C. The residue obtained is triturated in ether (30 cc), filtered off, washed successively with water (5 cc), 3 times with methanol (15 cc in total) and 3 times with ether (30 cc in total) and dried under reduced pressure (0.3 mm Hg; 0.04 kPa) at 50° C. This yields $N^2$-[N-(N-lauroyl-L-alanyl)-D-isoglutaminyl]-2(L),6(D,L)-diamino-4-thiapimelamic acid (0.41 g).

Rf=0.60 [silica gel; pyridine/ethyl acetate/acetic acid/water/methanol (30/40/6/10/10 by volume)].

Analysis: Calculated % C 53.04; H 8.21; N 14.27; S 5.44. Found % C 51.1; H 7.9; N 13.6; S 5.4.

Mass spectrum: M=588 (theory=588)

EXAMPLE 17

Isobutyl chloroformate (0.55 cc) is added to a solution, kept at −8° C., of N-t-butoxycarbonylglycine (73.2 mg) in a mixture of tetrahydrofuran (120 cc) and triethylamine (0.58 cc). The mixture is stirred for 20 minutes at −8° C. and a solution, cooled to 4° C., of $N^2$-[N-(N-lauroyl-L-alanyl)-D-isoglutaminyl]-2(L),6(D,L)-diamino-4-thiapimelamic acid (2.46 g) in a mixture of 1 N sodium hydroxide solution (4.18 cc) and water (120 cc) is then added. The reaction mixture is stirred for 5 minutes at 0° C. and then for 20 hours at about 20° C. The tetrahydrofuran is evaporated off by concentration under reduced pressure (20 mm Hg; 2.7 kPa) at 50° C. The concentrate is acidified to pH 2 by adding 4 N hydrochloric acid. The precipitate which has appeared is filtered off, washed successively 4 times with water (200 cc in total) and 3 times with ethyl acetate (150 cc in total) and dried under reduced pressure (20 mm Hg; 2.7 kPa) at 20° C. This yields a white powder (2.25 g) which is chromatographed on neutral silica gel (0.04–0.063 mm) (112 g) contained in a column of diameter 3.2 cm. Elution is carried out successively with an ethyl acetate/acetic acid mixture (20/80 by volume) (1 liter) and acetic acid (1 liter), 25 cc fractions being collected. Fractions 41 to 80 are combined and concentrated to dryness under reduced pressure (20 mm Hg; 2.7 kPa) at 50° C. The residue obtained is triturated in ether (100 cc) and dried under reduced pressure (20 mm Hg; 2.7 kPa) at 50° C. This yields $N^2$-[N-(N-lauroyl-L-alanyl)-D-isoglutaminyl]-$N^6$-(t-butoxycarbonylglycyl)-2(L),6(D,L)-diamino-4-thiapimelamic acid (1.04 g).

Rf=0.57 [silica gel; n-butanol/pyridine/acetic acid/water (50/20/6/24 by volume)].

Rf=0.69 [silica gel; ethyl acetate/acetic acid (2/8 by volume)].

$N^2$-[N-(N-lauroyl-L-alanyl)-D-isoglutaminyl]-$N^6$-(t-butoxycarbonylglycyl)-2(L),6(D,L)-diamino-4-thiapimelamic acid (0.88 g) is dissolved in a 1.6 N anhydrous solution of hydrogen chloride in acetic acid (12 cc). The solution is stirred for 35 minutes. The reaction medium is poured into ether (120 cc) and the mixture is stirred for 1 hour. The precipitate formed is filtered off, washed 3 times with ether (60 cc in total) and dried under reduced pressure (20 mm Hg; 2.7 kPa) at 20° C. The powder thus obtained is dissolved in water (70 cc). The pH of this solution is brought to 5–6 by adding 0.1 N ammonia solution. After standing for ½ hour, the precipitate formed is filtered off, washed successively 3 times with water (60 cc in total), 3 times with ether (60 cc in total), twice with ethyl acetate (40 cc in total) and twice with ether (40 cc in total) and dried under reduced pressure (20 mm Hg; 2.7 kPa) at 20° C. This yields a white powder (0.55 g) which is chromatographed on neutral silica gel (0.04–0.063 mm) (25 g) contained in a column of diameter 1.6 cm. Elution is carried out with acetic acid, 10 cc fractions being collected. Fractions 58 to 72 are combined and concentrated to dryness under reduced pressure (20 mm Hg; 2.7 kPa) at 50° C. The residue obtained is triturated in ether (50 cc), filtered off, washed 3 times with ether (60 cc in total) and dried under reduced pressure (0.3 mm Hg; 0.04 kPa) at 50° C. This yields $N^2$-[N-(N-lauroyl-L-alanyl)-D-isoglutaminyl]-$N^6$-glycyl-2(L),6(D,L)-diamino-4-thiapimelamic acid (300 mg).

Rf=0.33 [silica gel; n-butanol/pyridine/acetic acid/water (50/20/6/24 by volume)].

Analysis: Calculated % C 52.07; H 7.96; N 15.18; S 4.96. Found % C 50.5; H 8.0; N 14.1; S 4.9.

EXAMPLE 18

Isobutyl chloroformate (1 cc) is added to a solution, kept at −8° C., of benzyl O-acetyl-D-lactoyl-L-alanyl-α-D-glutamate (3.38 g) in a mixture of tetrahydrofuran (160 cc) and triethylamine (1.12 cc). The mixture is stirred for 20 minutes at −8° C. and a solution, cooled to 2° C., of $N^2$-benzyloxycarbonyl-L,L-2,6-diamino-4-thiapimelamic acid (3.02 g) in a mixture of N sodium hydroxide solution (16 cc) and water (60 cc) is then added.

The reaction mixture is stirred for 5 minutes at −8° C. and then for 20 hours at about 20° C. The tetrahydrofuran is evaporated off by concentration under reduced pressure (20 mm Hg; 2.7 kPa) at 50° C.; the concentrate is cooled to 0° C., acidified to pH 2 by adding 4 N hydrochloric acid (about 6 cc) and extracted 5 times with ethyl acetate (300 cc in total). The combined organic phases are washed successively with water (40 cc) and a saturated solution of sodium chloride (20 cc), dried over sodium sulphate and concentrated to dryness under reduced pressure (20 mm Hg; 2.7 kPa) at 50° C. This yields an oil (5.68 g) which is chromatographed on neutral silica gel (0.04–0.063 mm) (100 g) contained in a column of diameter 3 cm. Elution is carried out successively with ethyl acetate (400 cc), an ethyl acetate/acetic acid mixture (98/2 by volume) (360 cc), an ethyl acetate/acetic acid mixture (95/5 by volume) (320 cc) and an ethyl acetate/acetic acid mixture (9/1 by volume) (280 cc), 40 cc fractions being collected. Fractions 23 to 34 are combined and concentrated to dryness under reduced pressure (20 mm Hg; 2.7 kPa) at 50° C. This yields $N^6$-[$O^1$-benzyl-N-(O-acetyl-D-lactoyl-L-alanyl)-γ-D-glutamyl]-$N^2$-benzyloxycarbonyl-L,L-2,6-diamino-4-thiapimelamic acid (5.06 g) in the form of an oil.

Rf=0.67 [silica gel; n-butanol/pyridine/acetic acid/water (50/20/6/24 by volume)].

Rf=0.23 [silica gel; ethyl acetate/acetic acid (9/1 by volume)].

$N^6$-[$O^1$-Benzyl-N-(O-acetyl-D-lactoyl-L-alanyl)-γ-D-glutamyl]-$N^2$-benzyloxycarbonyl-L,L-2,6-diamino-4-thiapimelamic acid (3.16 g) is dissolved in a mixture of a 35% strength solution of hydrogen bromide in acetic acid (13 cc) and acetic acid (11 cc). The reaction medium is stirred for 2 hours, ether (500 cc) is then added thereto and the mixture is left to stand overnight. The precipitate which has appeared is filtered off, washed 3 times with ether (150 cc in total) and dried under reduced pressure (20 mm Hg; 2.7 kPa) at 20° C. This yields $N^6$-[$O^1$-benzyl-N-(O-acetyl-D-lactoyl-L-alanyl)-γ-D-glutamyl]-L,L-2,6-diamino-4-thiapimelamic acid (2.22 g) in the form of a hygroscopic powder.

Rf=0.83 [silica gel; isopropanol/water (6/4 by volume)].

$N^6$-[$O^1$-Benzyl-N-(O-acetyl-D-lactoyl-L-alanyl)-γ-D-glutamyl]-L,L-2,6-diamino-4-thiapimelamic acid (2.20 g) is dissolved in a mixture of methanol (14 cc) and 1 N sodium hydroxide solution (14 cc). The reaction mixture is stirred for 2 hours. It is neutralised to pH 7 by adding 1 N hydrochloric acid and concentrated under reduced pressure (20 mm Hg; 2.7 kPa) at 50° C., the concentrate is taken up in water (3 cc) and the solution is acidified with 4 N hydrochloric acid (3.5 cc). The solution thus obtained is chromatographed on a Sephadex G-10 column of height 2 meters and diameter 2.2 cm. Elution is carried out with water, 5 cc fractions being collected. Fractions 57 to 69 are combined, lyophilised and dried under reduced pressure (0.3 mm Hg; 0.04 kPa) at 60° C. This yields $N^6$-[N-(N-D-lactoyl-L-alanyl)-γ-D-glutamyl]-L,L-2,6-diamino-4-thiapimelamic acid (900 mg).

Rf=0.75 [silica gel; isopropanol/water (6/4 by volume)].

Analysis: Calculated % C 42.58; H 6.10; N 14.60; S 6.69. Found % C 39.7; H 6.4; N 13.2; S 6.4.

Benzyl O-acetyl-D-lactoyl-L-alanyl-α-D-glutamate can be prepared in the following manner:

Isobutyl chloroformate (5.5 cc) is added to a solution, kept at −6° C., of O-acetyl-D-lactic acid (5.61 g) in a mixture of tetrahydrofuran (425 cc) and triethylamine (6 cc). The mixture is stirred for 20 minutes at −6° C.

and a solution, cooled to 3° C., of benzyl L-alanyl-α-D-glutamate hydrochloride (14.66 g) in a mixture of 1 N sodium hydroxide solution (85 cc) and water (42 cc) is then added.

The reaction mixture is stirred for a few minutes at 0° C. and then for 18 hours at about 20° C. The mixture is acidified to pH 2 by adding 1 N hydrochloric acid (about 50 cc). The tetrahydrofuran is evaporated off by concentration under reduced pressure (20 mm Hg; 2.7 kPa) at 50° C. Ethyl acetate (100 cc) and 1 N hydrochloric acid (35 cc) are added to the concentrate. The organic phase is separated off and the aqueous phase is extracted 3 times with ethyl acetate (150 cc in total). All the organic phases are combined, washed with a saturated solution of sodium chloride (50 cc), dried over sodium sulphate and concentrated to dryness under reduced pressure (20 mm Hg; 2.7 kPa) at 50° C. This yields an oil which is chromatographed on neutral silica gel (0.03–0.2 mm) (550 g) contained in a column of diameter 5 cm. Elution is carried out successively with an ethyl acetate/methanol mixture (98/2 by volume) (500 cc), an ethyl acetate/methanol mixture (95/5 by volume) (700 cc), an ethyl acetate/methanol mixture (9/1 by volume) (400 cc) and an ethyl acetate/methanol mixture (8/2 by volume) (600 cc), 100 cc fractions being collected. Fractions 13 to 22 are combined and concentrated to dryness under reduced pressure (20 mm Hg; 2.7 kPa) at 50° C. This yields benzyl O-acetyl-D-lactoyl-L-alanyl-α-D-glutamate (8.78 g) in the form of an oil.

Rf=0.63 [silica gel; acetic acid/ethyl acetate (9/1 by volume)].

EXAMPLE 19

Isobutyl chloroformate (0.91 cc) is added to a solution, kept at −8° C., of benzyl N-(N-octanoyl-L-alanyl)-α-D-glutamate (3.04 g) in a mixture of tetrahydrofuran (140 cc) and triethylamine (0.98 cc). The mixture is stirred for 20 minutes at −8° C. and a solution, cooled to 2° C., of $N^2$-benzyloxycarbonyl-L,L-2,6-diamino-4-thiapimelamic acid (2.64 g) in a mixture of 1 N sodium hydroxide solution (14 cc) and water (53 cc) is then added.

The reaction mixture is stirred for 5 minutes at 0° C. and then for 4 hours at about 20° C. The tetrahydrofuran is evaporated off by concentration under reduced pressure (20 mm Hg; 2.7 kPa) at 50° C.; the concentrate is cooled to 0° C., acidified to pH 2 by adding 4 N hydrochloric acid (about 5 cc) and extracted 5 times with ethyl acetate (300 cc in total). The combined organic phases are washed successively with water (25 cc) and a saturated solution of sodium chloride (25 cc), dried over sodium sulphate and concentrated to dryness under reduced pressure (20 mm Hg; 2.7 kPa) at 50° C. This yields a light beige powder (5.18 g) which is chromatographed on neutral silica gel (0.04–0.063 mm) (100 g) contained in a column of diameter 3 cm. Elution is carried out successively with ethyl acetate (160 cc), an ethyl acetate/acetic acid mixture (97/3 by volume) (360 cc), an ethyl acetate/acetic acid mixture (95/5 by volume) (720 cc) and an ethyl acetate/acetic acid mixture (9/1 by volume) (680 cc), 40 cc fractions being collected. Fractions 15 to 48 are combined and concentrated to dryness under reduced pressure (20 mm Hg; 2.7 kPa) at 50° C. The residue obtained is triturated in ether (100 cc), filtered off and dried. This yields $N^6$-[$O^1$-benzyl-N-(N-octanoyl-L-alanyl)-γ-D-glutamyl]-$N^2$-benzyloxycarbonyl-L,L-2,6-diamino-4-thiapimelamic acid (3.33 g).

Rf=0.37 [silica gel; ethyl acetate/acetic acid (9/1 by volume)].

Mass spectrometry: M=757 (theory=757).

$N^6$-[$O^1$-Benzyl-N-(N-octanoyl-L-alanyl)-γ-D-glutamyl]-$N^2$-benzyloxycarbonyl-L,L-2,6-diamino-4-thiapimelamic acid (3.3 g) is dissolved in a mixture of methanol (33 cc) and 1 N sodium hydroxide solution (9.7 cc). The reaction medium is stirred for 60 minutes. Part of the methanol is evaporated off by concentration under reduced pressure (20 mm Hg; 2.7 kPa) at 50° C. The concentrate is diluted with water (30 cc) and acidified to pH 1 by adding 1 N hydrochloric acid. The mixture is left to stand for 18 hours. An oil separates out on the walls; it is separated off by decantation, washed twice with water (40 cc in total) and dried under reduced pressure (20 mm Hg; 2.7 kPa) at 20° C. This yields an oil (2.86 g) which is chromatographed on neutral silica gel (0.04–0.063 mm) (77 g) contained in a column of diameter 3 cm. To do this, the oil (2.86 g) is dissolved in acetic acid (30 cc), and neutral silica gel (0.04–0.063 mm) (8 g) is added to the solution obtained. The mixture is evaporated to dryness under reduced pressure (20 mm Hg; 2.7 kPa) at 50° C. and the residue thus obtained is charged onto the silica column. Elution is carried out successively with an ethyl acetate/acetic acid mixture (9/1 by volume) (80 cc), an ethyl acetate/acetic acid mixture (8/2 by volume) (80 cc) and an ethyl acetate/acetic acid mixture (1/1 by volume) (280 cc), 40 cc fractions being collected. Fractions 5 to 11 are combined and concentrated to dryness under reduced pressure (20 mm Hg; 2.7 kPa) at 50° C. The residue is triturated in ethyl acetate (40 cc), filtered off and dried. This yields a powder (1.94 g) which is chromatographed on neutral silica gel (0.04–0.063 mm) (80 g) contained in a column of diameter 3.5 cm. To do this, the powder (1.94 g) is dissolved in acetic acid (30 cc), and neutral silica gel (0.04–0.063 mm) (6 g) is added to the solution obtained. The mixture is evaporated to dryness under reduced pressure (20 mm Hg; 2.7 kPa) at 50° C. and the residue thus obtained is charged onto the silica column. Elution is carried out successively with an ethyl acetate/acetic acid mixture (8/2 by volume) (600 cc) and an ethyl acetate/acetic acid mixture (7/3 by volume) (400 cc), 40 cc fractions being collected. Fractions 7 to 25 are combined and concentrated to dryness under reduced pressure (20 mm Hg; 2.7 kPa) at 50° C. The residue obtained is triturated in ether (30 cc), filtered off and dried. This yields $N^6$-[N-(N-octanoyl-L-alanyl)-γ-D-glutamyl]-$N^2$-benzyloxycarbonyl-L,L-2,6-diamino-4-thiapimelamic acid (1.44 g).

Rf=0.52 [silica gel; n-butanol/pyridine/acetic acid/water (50/20/6/24 by volume)].

$N^6$-[N-(N-Octanoyl-L-alanyl)-γ-D-glutamyl]-$N^2$-benzyloxycarbonyl-L,L-2,6-diamino-4-thiapimelamic acid (1.4 g) is dissolved in a mixture of a 33% strength solution of hydrogen bromide in acetic acid (5.6 cc) and acetic acid (5 cc). The reaction mixture is stirred for 2 hours at 28° C. and concentrated to dryness under reduced pressure (20 mm Hg; 2.7 kPa) at 50° C. The residue obtained is triturated in ether (60 cc). An oil separates out on the walls and it is separated off by decantation, triturated again in ether (50 cc), separated off again by decantation and dissolved in water (200 cc). This aqueous phase is concentrated to dryness under reduced pressure (20 mm Hg; 2.7 kPa) at 55° C. This yields an oil which is chromatographed on neutral silica gel (0.04–0.063 mm) (80 g) contained in a column of diameter 3 cm. Elution is carried out with a mixture of methanol, ethyl acetate and ammonia solution (d=0.92) (75/25/0.5 by volume), 20 cc fractions being collected. Fractions 15 to 21 are combined and concentrated to dryness under reduced pressure (20 mm Hg; 2.7 kPa) at 50° C. This yields a white powder (460 mg). This white powder (360 mg) is dissolved in water (5 cc) and chromatographed on a Sephadex G-10 column of height 2 meters and diameter 2.2 cm. Elution is carried out with water, 5 cc fractions being collected. Fractions 68 to 84 are combined, lyophilised and dried under reduced pressure (0.3 mm Hg; 0.04 kPa) at 60° C. This yields $N^6$-[N-(N-octanoyl-L-alanyl)-γ-D-glutamyl]-L,L-2,6-diamino-4-thiapimelamic acid (300 mg).

Rf=0.25 [silica gel; n-butanol/pyridine/acetic acid/water (50/20/6/24 by volume)].

Analysis: Calculated % C 49.52; H 7.37; N 13.12; S 6.01. Found % C 45.3; H 7.4; N 11.7; S 5.7.

Sulphuric ash: 1%.

Benzyl N-octanoyl-L-alanyl-α-D-glutamate can be prepared in the following manner:

Isobutyl chloroformate (3.6 cc) is added to a solution, kept at −1° C., of octanoic acid (3.95 g) in tetrahydrofuran (140 cc) and triethylamine (3.8 cc). The mixture is stirred for 20 minutes at −1° C. and a solution, cooled to 0° C., of benzyl L-alanyl-α-D-glutamate hydrochloride (9.45 g) in a mixture of 1 N sodium hydroxide solution (54.8 cc) and water (30 cc) is then added. The reaction mixture is stirred for 1 hour at −1° C. and then for 20 hours at about 20° C. It is then acidified to pH 1 by adding 1 N hydrochloric acid. The tetrahydrofuran is evaporated off under reduced pressure (20 mm Hg; 2.7 kPa) at 45° C. and the concentrate is then extracted with ethyl acetate (100 cc). The organic phase thus obtained is washed twice with 1 N hydrochloric acid (50 cc in total) and with a saturated solution of sodium chloride (25 cc) and concentrated to dryness under reduced pressure (20 mm Hg; 2.7 kPa) at 45° C. This yields a pale yellow oil (10 g) which is chromatographed on a column of diameter 2.5 cm, containing neutral silica gel (0.063–0.20 mm) (200 g). Elution is carried out with ethyl acetate, 100 cc fractions being collected. Fractions 7 to 9 are combined and concentrated to dryness under reduced pressure (20 mm Hg; 2.7 kPa) at 45° C. The residue obtained is triturated in an ether/petroleum ether mixture (b.p.=35°–60° C.) (¼ by volume) (100 cc), filtered off and dried. This yields benzyl N-octanoyl-L-alanyl-α-D-glutamate (3.27 g) in the form of a white powder.

Rf=0.56 [silica gel; ethyl acetate/methanol (8/2 by volume)].

EXAMPLE 20

Isobutyl chloroformate (1 cc) is added to a solution, kept at 10° C., of benzyl N-(N-docosanoyl-L-alanyl)-α-D-glutamate (5.047 g) in a mixture of tetrahydrofuran (160 cc) and triethylamine (1.12 cc). The mixture is stirred for 20 minutes at 10° C. and a solution, cooled to 2° C., of $N^2$-benzyloxycarbonyl-L,L-2,6-diamino-4-thiapimelamic acid (3.023 g) in a mixture of 1 N sodium hydroxide solution (16 cc) and water (60 cc) is then added.

The reaction mixture is stirred for 16 hours at about 20° C. The reaction mixture is acidified to pH 1 by adding 4 N hydrochloric acid (6 cc) and extracted 5 times with ethyl acetate (300 cc in total). The combined organic phases are washed successively with water (30 cc) and a saturated solution of sodium chloride (30 cc), dried over sodium sulphate and concentrated to dryness under reduced pressure (20 mm Hg; 2.7 kPa) at 50° C. This yields a solid (7.7 g) which is chromatographed on neutral silica gel (0.04–0.063 mm) (150 g) contained in a column of diameter 3.5 cm. To do this, the powder (7.7 g) is dissolved in acetic acid (60 cc), and neutral silica gel (0.04–0.063 mm) (20 g) is added to the solution obtained. The mixture is evaporated to dryness under reduced pressure (20 mm Hg; 2.7 kPa) at 50° C. and the residue thus obtained is charged onto the silica column. Elution is carried out successively with ethyl acetate (240 cc), an ethyl acetate/acetic acid mixture (98/2 by volume) (320 cc), an ethyl acetate/acetic acid mixture (95/5 by volume) (640 cc), an ethyl acetate/acetic acid mixture (9/1 by volume) (360 cc), an ethyl acetate/acetic acid mixture (8/2 by volume) (440 cc) and acetic acid (400 cc), 40 cc fractions being collected. Fractions 11 to 60 are combined and concentrated to dryness under reduced pressure (20 mm Hg; 2.7 kPa) at 50° C. This yields impure $N^6$-[$O^1$-benzyl-N-(N-docosanoyl-L-alanyl)-γ-D-glutamyl]-$N^2$-benzyloxycarbonyl-L,L-2,6-diamino-4-thiapimelamic acid (4.51 g).

Rf (main spot)=0.72 [silica gel; ethyl acetate/acetic acid (9/1 by volume)].

$N^6$-[$O^1$-Benzyl-N-(N-docosanoyl-L-alanyl)-γ-D-glutamyl]-$N^2$-benzyloxycarbonyl-L,L-2,6-diamino-4-thiapimelamic acid (4.4 g) is dissolved in a mixture of methanol (220 cc) and 1 N sodium hydroxide solution (10.1 cc). The reaction mixture is stirred for 2 days and poured into a mixture of water (670 cc) and 1 N hydrochloric acid (13 cc); the precipitate obtained is filtered off, washed 5 times with water (125 cc in total) and dried under reduced pressure (20 mm Hg; 2.7 kPa) at 20° C. This yields a cream-coloured powder (2.1 g) which is dissolved in a mixture of a 33% strength solution of hydrogen bromide in acetic acid (8 cc) and acetic acid (8 cc). The reaction mixture is stirred for 3 hours at 20° C. The insoluble material formed is filtered off, washed successively 5 times with acetic acid (12.5 cc in total), with ether (5 cc) and with petroleum ether (b.p.=35°–60° C.) (5 cc) and dried under reduced pressure (20 mm Hg; 2.7 kPa) at 20° C. This yields a cream-coloured powder (1.66 g). The filtrates are combined and concentrated to dryness under reduced pressure (20 mm Hg; 2.7 kPa) at 20° C., the residue is taken up 3 times in ether (150 cc in total), the combined solutions are concentrated to dryness under reduced pressure (20 mm Hg; 2.7 kPa) at 30° C. and the residue is taken up in a mixture of ether (25 cc) and petroleum ether (b.p.=35°–60° C.) (25 cc). The solid is filtered off, then washed twice with petroleum ether (b.p.=35°–60° C.) (20 cc in total) and dried under reduced pressure (20 mm Hg; 2.7 kPa) at 20° C. The whole of the powder obtained (1.66 g+0.55 g) is poured into vigorously stirred water (500 cc). After stirring for 1 hour, the precipitate is filtered off, washed 3 times with water (150 cc in total) and dried under reduced pressure (20 mm Hg; 2.7 kPa) at 20° C. This yields a cream-coloured powder (1.52 g) which is chromatographed on neutral silica gel (0.04–0.063 mm) (45 g) contained in a column of diameter 2 cm. To do this, the powder (1.52 g) is dissolved in acetic acid (60 cc) warmed to 60° C., and neutral silica gel (0.04–0.063 mm) (5 g) is added to the solution obtained. The mixture is evaporated to dryness under reduced pressure (20 mm Hg; 2.7 kPa) at 50° C. and the residue thus obtained is charged onto the silica column. Elution is carried out with acetic acid, 30 cc fractions being collected. Fractions 11 to 27 are combined and concentrated to dryness under reduced pressure (20 mm Hg; 2.7 kPa) at 50° C. This yields a pink powder (720 mg) which is chromatographed on neutral silica gel (0.04–0.063 mm) (36 g) contained in a column of diameter 2 cm. To do this, the powder (720 mg) is dissolved in acetic acid (30 cc), and neutral silica gel (0.04–0.063 mm) (3 g) is added to the solution obtained. The mixture is evaporated to dryness under reduced pressure (20 mm Hg; 2.7 kPa) at 50° C. and the residue thus obtained is charged onto the silica column. Elution is carried out with an ethyl acetate/acetic acid mixture (2/8 by volume), 40 cc fractions being collected. Fractions 12 to 29 are combined and concentrated to dryness under reduced pressure (20 mm Hg; 2.7 kPa) at 50° C. The residue obtained is triturated in a mixture of ether (25 cc) and petroleum ether (b.p.=35°–60° C.) (25 cc), filtered off and dried under reduced pressure (0.3 mm Hg; 0.04 kPa) at 20° C. This yields $N^6$-[N-(N-docosanoyl-L-alanyl)-$\gamma$-D-glutamyl]-L,L-2,6-diamino-4-thipimelamic acid (220 mg).

Rf=0.32 [silica gel; n-butanol/pyridine/acetic acid/water (50/20/6/24 by volume)].

Rf=0.60 [silica gel; acetic acid].

Mass spectrum: M=729 (theory=729).

Benzyl N-docosanoyl-L-alanyl-$\alpha$-D-glutamate can be prepared in the following manner:

Isobutyl chloroformate (1.95 cc) is added to a solution, kept at 25° C., of docosanoic acid (5.19 g) in a mixture of tetrahydrofuran (150 cc) and triethylamine (2.1 cc). The mixture is stirred for 20 minutes at 25° C. and a solution of benzyl L-alanyl-$\alpha$-D-glutamate hydrochloride (5.69 g) in a mixture of 1 N sodium hydroxide solution (33 cc) and water (17 cc) is then added. The reaction mixture is stirred for 30 minutes at about 30° C. and then for 18 hours at about 20° C. Water (100 cc) is then added and the mixture is acidified to pH 1. This yields a precipitate which is filtered off, washed 3 times with water (75 cc in total) and dried under reduced pressure (0.3 mm Hg; 0.04 kPa) at 20° C. This yields a white powder (6.53 g). Some of this powder (6 g) is dissolved in tetrahydrofuran (50 cc) containing neutral silica gel (0.04–0.063 mm) (20 g). The mixture is concentrated to dryness under reduced pressure (20 mm Hg; 2.7 kPa) at 50° C. and the whole is charged onto a column of diameter 3.5 cm, containing neutral silica gel (0.04–0.063 mm) (180 g). Elution is carried out successively with a cyclohexane/ethyl acetate mixture (1/1 by volume) (1,300 cc), ethyl acetate (600 cc), an ethyl acetate/tetrahydrofuran mixture (95/5 by volume (500 cc), an ethyl acetate/tetrahydrofuran mixture (9/1 by volume) (900 cc), an ethyl acetate/tetrahydrofuran mixture (8/2 by volume) (800 cc), an ethyl acetate/tetrahydrofuran mixture (6/4 by volume) (1,000 cc), an ethyl acetate/tetrahydrofuran mixture (4/6 by volume) (900 cc), an ethyl acetate/tetrahydrofuran mixture (2/8 by volume) (500 cc) and tetrahydrofuran (600 cc), 100 cc fractions being collected.

Fractions 17 to 68 are combined and concentrated to dryness under reduced pressure (20 mm Hg; 2.7 kPa) at 50° C. This yields benzyl N-docosanoyl-L-alanyl-$\alpha$-D-glutamate (3.31 g).

Rf=0.54 [silica gel; ethyl acetate/tetrahydrofuran (8/2 by volume)].

The present invention also relates to pharmaceutical compositions which comprise, as active ingredient, a peptide of general formula I or a non-toxic salt thereof, in association with a pharmaceutically acceptable carrier or diluent. These compositions can be used either as vaccine adjuvants or as non-specific stimulants of antiinfectious and antitumoral immunity.

Used as vaccine adjuvants, the products according to the invention are administered at the same time and by the same method as the antigen (viral, bacterial, parasitic or other antigen) against which it is desired to increase the cell immunity reactions (delayed-type hypersensitivity) or the production of circulating or local antibodies in the immunised subject (man or domestic animal).

The products are administered in relatively low doses (of the order of a mg) as a mixture with the antigen and by the same method (intramuscular, subcutaneous, intravenous, intranasal or oral method). If necessary, the product and the antigen can be emulsified in an appropriate oily excipient or incorporated into liposomes.

As non-specific immunostimulants, the products are administered at doses of between 0.1 and 50 mg/kg by the parenteral method (intravenous, subcutaneous or intramuscular method) or by the intranasal, oral, rectal or, if appropriate, intratumoral method.

Tablets, pills, powders or granules can be used as solid compositions for oral administration. In these compositions, the active product is mixed with one or more diluents such as sucrose, lactose or starch. These compositions can also comprise substances other than diluents, e.g. a lubricant such as magnesium stearate.

Solutions, suspensions, syrups, elixirs containing inert diluents, such as water or paraffin oil, and pharmaceutically acceptable emulsions can be used as liquid compositions for oral administration. These compositions can comprise substances other than diluents, e.g. wetting, sweetening or flavouring products.

The compositions for parenteral administration can be suspensions, emulsions or aqueous sterile solutions. Polyethylene glycol, propylene glycol, vegetable oils, in particular olive oil, and injectable organic esters, e.g. ethyl oleate, can be employed as the vehicle in the former cases. These compositions can also contain adjuvants, in particular wetting, emulsifying or dispersing agents.

Sterilisation can be carried out in several ways, e.g. using a bacteriological filter, by incorporating sterilising agents into the composition or by heating. The compositions can also be prepared in the form of solid compositions sterilised e.g. by irradiation, which can be dissolved in sterile water or dispersed in any other injectable sterile medium, if appropriate at the time of use.

The compositions for intranasal administration can be suspensions, emulsions or aqueous sterile solutions, which can be associated, if appropriate, with a compatible propellant.

The compositions for rectal administration are suppositories which can contain excipients, such as cacao butter or a semi-synthetic glyceride, in addition to the active product.

The following Examples illustrate compositions according to the invention:

EXAMPLE A

A solution which can be administered intravenously and has the following composition is prepared in accordance with the usual technique:

| | |
|---|---|
| $N^2$-[N-(N-lauroyl-L-alanyl)-$\gamma$-D-glutamyl]-L,L-2,6-diamino-4-thiapimelic acid | 0.5 g |

-continued

| injectable solution | 5 cc |

EXAMPLE B

A solution which can be administered intravenously and has the followiang composition is prepared in accordance with the usual technique:

| $N^2$—[N—(N—lauroyl-L—alanyl)-γ-D-glutamyl]-$N^6$—glycyl-2(L),6(D,L)—diamino-4-thiapimelamic acid | 0.5 g |
| injectable solution | 5 cc |

EXAMPLE C

A solution which can be administered intravenously and has the following composition is prepared in accordance with the usual technique:

| $N^2$—[N—(N—lauroyl-L—alanyl)-γ-D-glutamyl]-L,L—2,6-diamino-4-thiapimelamic acid | 0.5 g |
| injectable solution | 5 cc |

EXAMPLE D

A solution which can be administered intravenously and has the following composition is prepared in accordance with the usual technique:

| $N^2$—[N—(N—lauroyl-L—alanyl)-γ-D-glutamyl]-$N^6$—glycyl-L,L—2,6-diamino-4-thiapimelamic acid | 0.5 g |
| injectable solution | 5 cc |

We claim:
1. A tri-, tetra- or penta-peptide of the general formula:

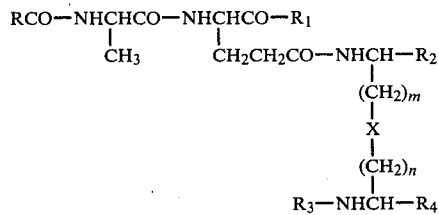

in which RCO— represents a fatty acid residue in which R represents an alkyl radical containing 1 to 44 carbon atoms (which is optionally substituted by a hydroxyl, phenyl or cyclohexyl radical), an alkenyl radical containing 2 to 29 carbon atoms, which can contain more than one double bond, or a mycolic acid residue such as encountered in the structure of the bacterial wall of mycobacteria, Nocardia or Corynebacteria, $R_1$ represents a hydroxyl or amino radical, an alkoxy radical containing 1 to 4 carbon atoms or a benzyloxy radical, the symbols $R_2$ and $R_4$, which are identical or different, represent a hydrogen atom, a carboxyl or carbamoyl radical, an alkoxycarbonyl radical of which the alkyl part contains 1 to 4 carbon atoms, a benzyloxycarbonyl radical or an N-carbonylglycyl or N-carbonyl-D-alanyl radical optionally esterified by an alkyl radical containing 1 to 4 carbon atoms or a benzyl radical, it being understood that $R_2$ and $R_4$ cannot simultaneously represent a hydrogen atom, $R_3$ represents a hydrogen atom or a glycyl or D-alanyl residue, it being understood that if $R_2$ and $R_4$, which are identical or different, each represent an N-carbonylglycyl or N-carbonyl-D-alanyl radical, $R_3$ represents a hydrogen atom, X represents a sulphur atom or a methylene radical, and m and n, which are identical or different, each represent an integer equal to 1 or 2, it being understood that if X represents a methylene radical, m and n cannot simultaneously be equal to 1, and it being understood that the alanine bonded to the glutamic acid is in the L form, the glutamic acid is in the D form, the lanthionine, if X represents a sulphur atom and m and n are equal to 1, the cystathionine, if X represents a sulphur atom and m and n are different, the homolanthionine, if X represents a sulphur atom and m and n are equal to 2, and the 2,7-diaminosuberic acid, if X represents a methylene radical and one of the symbols m or n is equal to 1 and the other is equal to 2, are in the D,D, L,L, D,D/L,L (racemic) or D,L (meso) form or in the form of L/meso or D/meso mixtures, and the thialysine, if one of the symbols $R_2$ or $R_4$ represents a hydrogen atom, X represents a sulphur atom and m and n are equal to 1, is in the L, D or D,L form, or a non-toxic salt thereof.

2. A peptide according to claim 1 in which RCO— represents a fatty acid residue in which R represents an alkyl radical containing 2 to 21 carbon atoms, which is optionally substituted by a hydroxyl radical, $R_1$ represents a hydroxyl or amino radical, the symbols $R_2$ and $R_4$, which are identical or different, represent a hydrogen atom or a carboxyl, carbamoyl, N-carbonylglycyl or N-carbonyl-D-alanyl radical, it being understood that $R_2$ and $R_4$ cannot simultaneously represent a hydrogen atom, $R_3$ represents a hydrogen atom or a glycyl or D-alanyl residue, it being understood that if $R_2$ and $R_4$, which are identical or different, each represent an N-carbonylglycyl or N-carbonyl-D-alanyl radical, $R_3$ represents a hydrogen atom, X represents a sulphur atom and m and n, which are identical or different, each represent an integer equal to 1 or 2, it being understood that the alanine bonded to the glutamic acid is in the L form, the glutamic acid is in the D form, the lanthionine, if m and n are equal to 1, the cystathionine, if m and n are different, and the homolanthionine, if m and n are equal to 2, are in the D,D, L,L, D,D/L,L (racemic) or D,L (meso) form or in the form of L/meso or D/meso mixtures, and the thialysine, if one of the symbols $R_2$ or $R_4$ represents a hydrogen atom, and m and n are equal to 1, is in the L, D or D,L form, or a non-toxic salt thereof.

3. A compound according to claim 1 which is $N^2$-[N-(N-lauroyl-L-alanyl-γ-D-glutamyl]-L,L-2,6-diamino-4-thiapimelic acid or a non-toxic salt thereof.

4. A compound according to claim 1 which is $N^2$-[N-(N-lauroyl-L-alanyl)-γ-D-glutamyl]-$N^6$-glycyl-2(L),6(D,L)-diamino-4-thiapimelamic acid or a non-toxic salt thereof.

5. A compound according to claim 1 which is $N^2$-[N-(N-lauroyl-L-alanyl)-γ-D-glutamyl]-L,L-2,6-diamino-4-thiapimelamic acid or a non-toxic salt thereof.

6. A compound according to claim 1 which is $N^2$-[N-(N-lauroyl-L-alanyl)-γ-D-glutamyl]-$N^6$-glycyl-L,L-2,6-diamino-4-thiapimelamic acid or a non-toxic salt thereof.

7. A compound according to claim 1 which is $N^2$-[N-(N-lauroyl-L-alanyl)-γ-D-glutamyl]-2(L),6(D,L)-diamino-4-thiapimelamic acid, $N^2$-[N-(N-lauroyl-L- alanyl)-γ-D-glutamyl]-2(D/L mixture),6(L)-diamino-4-thiapimelamoylglycine, N⁶-[N-(N-lauroyl-L-alanyl)-γ-D-glutamyl]-2(L),6(D,L)-diamino-4-thiapimelamic acid, N²-glycyl-N⁶-[N-(N-lauroyl-L-alanyl)-γ-D-glutamyl]-2(L),6(D,L)-diamino-4-thiapimelamic acid, N²-[N-(N-lauroyl-L-alanyl)-γ-D-glutamyl]-L-lanthioninediamide hydrobromide, N²-[N-(N-lauroyl-L-alanyl)-γ-D-glutamyl]-L,L,-2,7-diamino-4-thiasuberamic acid, N⁶-[N-(N-lauroyl-L-alanyl)-D-isoglutaminyl]-2(L),6(D,L)-diamino-4-thiapimelamic acid or N⁶-[N-(N-lauroyl-L-alanyl)-γ-D-glutamyl]-N²-glycyl-L,L-2,6-diamino-4-thiapimelamic acid or a non-toxic salt thereof.

8. A compound according to claim 1 which is N⁶-[N-(N-lauroyl-L-alanyl)-γ-D-glutamyl]-L,L-2,6-diamino-4-thiapimelamic acid, N²-[N-(N-lauroyl-L-alanyl)-γ-D-glutamyl]]-2(D),6(L)-diamino-4-thiapimelamic acid, N²-[N-(N-lauroyl-L-alanyl)-D-isoglutaminyl]-2(L),6(D,L)-diamino-4-thiapimelamic acid, N²-[N-(N-lauroyl-L-alanyl)-D-isoglutaminyl]-N⁶-glycyl-2(L),6(D,L)-diamino-4-thiapimelamic acid, N⁶-[N-(N-D-lactoyl-L-alanyl)-γ-D-glutamyl]-L,L-2,6-diamino-4-thiapimelamic acid, N⁶-[N-(N-octanoyl-L-alanyl)-γ-D-glutamyl]-L,L-2,6-diamino-4-thiapimelamic acid or N⁶-[N-(N-docosanoyl-L-alanyl)-γ-D-glutamyl]-L,L-2,6-diamino-4-thiapimelamic acid or a non-toxic salt thereof.

9. A pharmaceutical composition for use as a vaccine adjuvant or immunostimulant which comprises, as active ingredient an effective amount of a peptide according to claim 1 or a non-toxic salt thereof in association with a pharmaceutically acceptable carrier or diluent.

10. Method of stimulating the immune reactions in man or a domestic animal which comprises administering thereto an effective amount of a peptide according to claim 1 or a non-toxic salt thereof.

* * * * *